(12) United States Patent
Shi et al.

(10) Patent No.: US 8,846,601 B2
(45) Date of Patent: Sep. 30, 2014

(54) MELANOCORTIN RECEPTOR-SPECIFIC PEPTIDES

(75) Inventors: Yi-qun Shi, East Brunswick, NJ (US); Shubh D. Sharma, Cranbury, NJ (US); John H. Dodd, Flemington, NJ (US); Wei Yang, Edison, NJ (US); Xin Chen, Furlong, PA (US)

(73) Assignee: Palatin Technologies, Inc., Cranbury, NJ (US)

( * ) Notice: Subject to any disclaimer, the term of this patent is extended or adjusted under 35 U.S.C. 154(b) by 218 days.

(21) Appl. No.: 13/311,824

(22) Filed: Dec. 6, 2011

(65) Prior Publication Data

US 2012/0178701 A1 Jul. 12, 2012

Related U.S. Application Data

(63) Continuation-in-part of application No. PCT/US2010/037589, filed on Jun. 7, 2010.

(60) Provisional application No. 61/184,929, filed on Jun. 8, 2009.

(51) Int. Cl.
*A61K 38/00* (2006.01)
*C07K 14/685* (2006.01)
*C07K 7/56* (2006.01)
*C07K 5/117* (2006.01)

(52) U.S. Cl.
CPC ............... *C07K 14/685* (2013.01); *A61K 38/00* (2013.01); *C07K 7/56* (2013.01); *C07K 5/1024* (2013.01)
USPC ............................ 514/1.1; 514/20.6; 530/317

(58) Field of Classification Search
None
See application file for complete search history.

(56) References Cited

U.S. PATENT DOCUMENTS

| | | | |
|---|---|---|---|
| 5,731,408 A | 3/1998 | Hadley et al. | |
| 6,054,556 A | 4/2000 | Huby et al. | |
| 6,350,430 B1 | 2/2002 | Dooley et al. | |
| 6,476,187 B1 | 11/2002 | Cone et al. | |
| 6,600,015 B2 | 7/2003 | Chen et al. | |
| 6,613,874 B1 | 9/2003 | Mazur et al. | |
| 6,693,165 B2 | 2/2004 | Bednarek | |
| 6,699,873 B1 | 3/2004 | Maguire et al. | |
| 6,887,846 B2 | 5/2005 | Catania et al. | |
| 6,951,916 B2 | 10/2005 | Mazur et al. | |
| 7,008,925 B1 | 3/2006 | Szardenings | |
| 7,176,279 B2 | 2/2007 | Sharma et al. | |
| 7,517,854 B2 | 4/2009 | Conde-Frieboes et al. | |
| 7,541,430 B2 | 6/2009 | Sensfuss et al. | |
| 2001/0056179 A1 | 12/2001 | Chen et al. | |
| 2002/0143141 A1 | 10/2002 | Chen et al. | |
| 2003/0064921 A1 | 4/2003 | Millhauser et al. | |
| 2003/0105024 A1 | 6/2003 | Cone et al. | |
| 2003/0212002 A1 | 11/2003 | Haskell-Luevano et al. | |
| 2004/0023859 A1 | 2/2004 | Mazur et al. | |
| 2004/0138136 A1 | 7/2004 | Sharma et al. | |
| 2005/0038230 A1 | 2/2005 | Sharma et al. | |
| 2005/0130901 A1 | 6/2005 | Lipton et al. | |
| 2005/0164914 A1 | 7/2005 | Sharma et al. | |
| 2005/0187164 A1 | 8/2005 | Pinel | |
| 2005/0239711 A1 | 10/2005 | Chen et al. | |
| 2006/0014194 A1 | 1/2006 | Sharma et al. | |
| 2006/0105951 A1 | 5/2006 | Cunningham et al. | |
| 2006/0111281 A1 | 5/2006 | Sharma et al. | |
| 2006/0258590 A1 | 11/2006 | Haskell-Luevano | |
| 2006/0293223 A1 | 12/2006 | Gadski et al. | |
| 2007/0027091 A1 | 2/2007 | Conde-Frieboes et al. | |
| 2007/0105759 A1 | 5/2007 | Flora et al. | |
| 2007/0123453 A1 | 5/2007 | Heiman et al. | |

(Continued)

FOREIGN PATENT DOCUMENTS

WO  WO-98/27113  6/1998
WO  WO-99/21571  5/1999

(Continued)

OTHER PUBLICATIONS

Prusis et al., Eur. J. Med. Chem., 2001 (36) 137-146.*

(Continued)

*Primary Examiner* — Karlheinz R Skowronek
*Assistant Examiner* — Roy Teller
(74) *Attorney, Agent, or Firm* — Stephen A. Slusher

(57) ABSTRACT

Melanocortin receptor-specific cyclic peptides of the formula

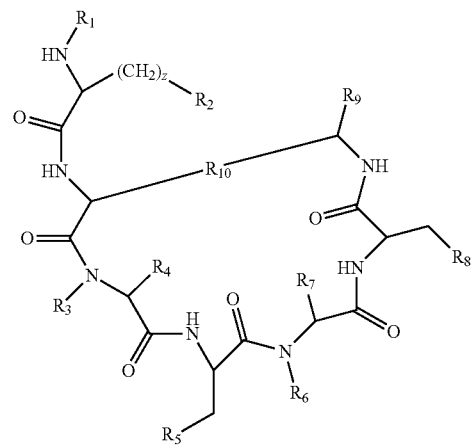

where $R_1$, $R_2$, $R_3$, $R_4$, $R_5$, $R_6$, $R_7$, $R_8$, $R_9$, $R_{10}$ and z are as defined in the specification, compositions and formulations including the peptides of the foregoing formula, and methods of preventing, ameliorating or treating melanocortin receptor-mediated diseases, indications, conditions and syndromes.

12 Claims, 1 Drawing Sheet

(56) References Cited

U.S. PATENT DOCUMENTS

| | | |
|---|---|---|
| 2007/0244054 A1 | 10/2007 | Sensfuss et al. |
| 2007/0293423 A1 | 12/2007 | Jungheim et al. |
| 2008/0004213 A1 | 1/2008 | Humphrey |
| 2008/0039387 A1 | 2/2008 | Sensfuss et al. |
| 2008/0305152 A1 | 12/2008 | Kleinig et al. |
| 2009/0069224 A1 | 3/2009 | Sharma et al. |
| 2010/0311648 A1 | 12/2010 | Dodd et al. |

FOREIGN PATENT DOCUMENTS

| | | |
|---|---|---|
| WO | WO-99/54358 | 10/1999 |
| WO | WO 00/05263 | 2/2000 |
| WO | WO-00/35952 | 6/2000 |
| WO | WO-00/58361 | 10/2000 |
| WO | WO-01/30808 | 5/2001 |
| WO | WO-01/52880 | 7/2001 |
| WO | WO-01/74844 | 10/2001 |
| WO | WO-01/85930 | 11/2001 |
| WO | WO-01/90140 | 11/2001 |
| WO | WO-02/18437 | 3/2002 |
| WO | WO-02/26774 | 4/2002 |
| WO | WO-03/006604 | 1/2003 |
| WO | WO-03/006620 | 1/2003 |
| WO | WO-2004/005324 | 1/2004 |
| WO | WO-2004/046166 | 6/2004 |
| WO | WO-2004/099246 | 11/2004 |
| WO | WO-2005/000338 | 1/2005 |
| WO | WO-2005/000339 | 1/2005 |
| WO | WO-2005/000877 | 1/2005 |
| WO | WO-2005/014617 | 2/2005 |
| WO | WO-2005/030797 | 4/2005 |
| WO | WO-2005/060985 | 7/2005 |
| WO | WO-2006/012667 | 2/2006 |
| WO | WO-2006/014552 | 2/2006 |
| WO | WO-2006/048449 | 5/2006 |
| WO | WO-2006/048450 | 5/2006 |
| WO | WO-2006/048451 | 5/2006 |
| WO | WO-2006-048452 | 5/2006 |
| WO | WO-2006/097526 | 9/2006 |
| WO | WO-2007/008684 | 1/2007 |
| WO | WO-2007-008704 | 1/2007 |
| WO | WO-2007/009894 | 1/2007 |
| WO | WO-2007/027574 | 3/2007 |
| WO | WO-2008/025094 | 3/2008 |
| WO | WO-2008/087186 | 7/2008 |
| WO | WO-2008/087187 | 7/2008 |
| WO | WO-2008/087188 | 7/2008 |
| WO | WO-2008/087190 | 7/2008 |
| WO | WO-2008/156677 | 12/2008 |
| WO | WO-2009/061411 | 5/2009 |
| WO | WO-2009/152079 | 12/2009 |

OTHER PUBLICATIONS

Li et al., Eur. J. Biochem., 1999, 265, 430-440.*

Adan, Rah et al., "The MC4 Receptor and Control of Appetite", *British Journal of Pharmacology*, (Oct. 16, 2006),149:815-827.

Balbani, Aracy P., et al., "Recent developments for smoking cessation and treatment of nicotine dependence", *Informa healthcare / Expert Opinion*, (2007),17:287-297.

Bednarek, Maria A., et al., "Analogs of MTII, Lactam Derivatives of alpha-Melanotropin, Modified at the n-Terminus, and their selectivity at human melanocortin receptors 3, 4 and 5", *Biochemical and Biophysical Research Communications*, (1999)261:209-213.

Communication, "Extended European Search Report", (Feb. 20, 2013).

Gautron, Laurent et al., "Melanocortin-4 Receptor Expression in a Vago-vagal Circuitry Involved in Postprandial Functions", *The Journal of Comparative Neurology*, (2010),518:6-24.

Giuliani, D. et al., "Selective melanocortin MC4 receptor agonists reverse haemorrhagic shock and prevent multiple organ damage", *British Journal of Pharmacology*, (2007)150:595-603.

Grieco, Paolo et al., "Structure-activity studies of new melanocortin peptides containing an aromatic amino acid at the N-terminal position", *Peptides*, 27(2),(Feb. 2006),472-481.

Hadley, Mac E., et al., "The Proopiomelanocortin System", *Annals New York Academy of Science*, (1995),1-21.

Maaser, Christian et al., "Role of the Melanocortin System in Inflammation", *Ann. N.Y. Acad. Science*, (2006),1072:123-134.

Navarro, Montserrat et al., "Effects of Melanocortin Receptor Activation and Blockade on Ethanol Intake: A Possible Role for the Melanocortin-4 Receptor", *Alcohol Clin. Exp. Res.*, (2005),29(6):949-957.

Nogueiras, Ruben et al., "The central melanocortin system directly controls peripheral lipid metabolism", *The Journal of Clinical Investigation*, (2007),117(11): 3475.

Wikberg, Jarl E., et al., "Targeting melanocortin receptors: an approach to treat weight disorders and sexual dysfunction", *Nature Reviews Drug Discovery*, (2008),7:307-323.

* cited by examiner

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic melanocortin binding peptide derived
      from human alpha-MSH

<400> SEQUENCE: 1

His Phe Arg Trp
1

<210> SEQ ID NO 2
<211> LENGTH: 13
<212> TYPE: PRT
<213> ORGANISM: Artificial Sequence
<220> FEATURE:
<223> OTHER INFORMATION: Synthetic melanocortin binding peptide derived
      from human alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 2

Ser Tyr Ser Met Glu His Phe Arg Trp Gly Lys Pro Val
1               5                   10

MELANOCORTIN RECEPTOR-SPECIFIC PEPTIDES

CROSS-REFERENCE TO RELATED APPLICATIONS

This application is a continuation-in-part of International Application No. PCT/US2010/037589, published as International Publication No. WO 2010/144344, entitled "Melanocortin Receptor-Specific Peptides", filed on Jun. 7, 2010, which in turn claimed priority to and the benefit of the filing of U.S. Provisional Patent Application Ser. No. 61/184,929 entitled "Melanocortin Receptor-Specific Peptides", filed Jun. 8, 2009. The specification and claims of each of the foregoing applications are incorporated herein by reference.

BACKGROUND OF THE INVENTION

1. Field of the Invention (Technical Field)

The present invention relates to melanocortin receptor-specific cyclic peptides which may be used in the treatment of melanocortin receptor-mediated diseases, indications, conditions and syndromes.

2. Description of Related Art

The following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, midbrain and brainstem, and melanocortin-5 receptors (MC5-R), expressed in a wide distribution of peripheral tissues. MC1-R has been suggested to be associated with hair and skin pigmentation and inflammation, MC2-R is believed to mediate steroidogenesis, MC3-R has been suggested to be associated with energy homeostasis, food intake, and inflammation, MC4-R is believed to control feeding behavior, energy homeostasis, and sexual function (e.g. erectile function), and MC5-R has been suggested to be involved in the exocrine gland system.

Significant work has been done in determining the structure of melanocortin receptors, including both the nucleic acid sequences encoding for the receptors and the amino acid sequences constituting the receptors. MC4-R is a G protein-coupled, 7-transmembrane receptor that is believed to be expressed primarily in the brain.

MC4-R inactivation has been shown to result in obesity (Hadley, 1999, *Ann N Y Acad Sci*, 885:1-21). Agouti-related protein (AgRP) is an endogeneous compound that has been suggested to be a MC antagonist or an inverse agonist on MC4-R. The α-melanocyte stimulating hormone (α-MSH) is believed to be the principle endogenous MC4-R agonist.

Also peripherally located MC4-R receptors have been suggested to be involved in the control of energy homeostasis, and the role of MC4-R signalling in the vagus nerve and its relevance for treatment of obesity and diabetes is discussed by Gautron et al., *The Journal of Comparative Neurology*, 518:6-24 (2010).

Peptides specific for MC4-R, and secondarily peptides specific for MC3-R, are believed to be useful in regulation of mammalian energy homeostasis, including use as agents for attenuating food intake and body weight gain. MC4-R agonist peptides are believed to be useful for treating sexual dysfunction, including male erectile dysfunction, and for decreasing food intake and body weight gain, such as for treatment of obesity. Such peptides may also be employed for decreasing voluntary ethanol consumption, treatment of drug addictions, and the like. MC4-R agonist peptides, as well as MC3-R agonist peptides, may further be employed for treatment of circulatory shock, ischemia, hemorrhagic shock, inflammatory diseases and related diseases, indications, conditions and syndromes. MC4-R antagonist peptides, by contrast, are believed to be useful for weight gain aid, such as for use in treatment of cachexia, sarcopenia, wasting syndrome or disease, and anorexia. Such peptides may also be employed for treatment of depression and related disorders. (Wikberg et al., *Nature Reviews, Drug Discovery*, 7, 307, (2008); Adan et al., *British J. Pharm.*, 149, 815-827 (2006); Nogueiras et al., *J. Clin., Invest.*, 117(11): 3475-3488 (2007); Maaser et al., *Ann. N.Y. Acad. Sci.*, 1072, 123-134 (2006); Giuliani et al., *British J. Pharm.*, 150, 595-603 (2007); Balbani, *Expert Opin. Ther. Patents*, 17(3), 287-297 (2007); and Navarro et al., *Alcohol. Clin. Exp. Res.*, 29(6), 949-957 (2005)).

Melanocortin receptor-specific cyclic peptides include cyclic α-melanocyte-stimulating hormone ("α-MSH") analog peptides such as Ac-Nle-cyclo(-Asp-His-D-Phe-Arg-Trp-Lys)-NH$_2$ (See U.S. Pat. No. 5,674,839 and U.S. Pat. No. 5,576,290) and Ac-Nle-cyclo(-Asp-His-D-Phe-Arg-Trp-Lys)-OH (See U.S. Pat. No. 6,579,968 and U.S. Pat. No. 6,794,489). These and other melanocortin receptor-specific peptides generally contain the central tetrapeptide sequence of native α-MSH, His$^6$-Phe$^7$-Arg$^8$-Trp$^9$ (SEQ ID NO:1), or a mimetic or variation thereof, such as the substitution of D-Phe for Phe$^7$. Other peptides or peptide-like compounds asserted to be specific for one or more melanocortin receptors are disclosed in U.S. Pat. Nos. 5,731,408, 6,054,556, 6,350,430, 6,476,187, 6,600,015, 6,613,874, 6,693,165, 6,699,873, 6,887,846, 6,951,916, 7,008,925, 7,176,279 and U.S. Pat. No. 7,517,854; in U.S. published patent application Publication Nos. 2001/0056179, 2002/0143141, 2003/0064921, 2003/0105024, 2003/0212002, 2004/0023859, 2005/0130901, 2005/0187164, 2005/0239711, 2006/0105951, 2006/0111281, 2006/0293223, 2007/0027091, 2007/0105759, 2007/0123453, 2007/0244054, 2008/0004213, 2008/0039387, and 2008/0305152; and in international patent applications nos. WO 98/27113, WO 99/21571, WO 00/05263, WO 99/54358, WO 00/35952, WO 00/58361, WO 01/30808, WO 01/52880, WO 01/74844, WO 01/85930, WO 01/90140, WO 02/18437, WO 02/26774, WO 03/006604, WO 2004/046166, WO 2004/099246, WO 2005/000338, WO 2005/000339, WO 2005/000877, WO 2005/030797, WO 2005/060985, WO 2006/012667, WO 2006/048449, WO 2006/048450, WO 2006/048451, WO 2006/048452, WO 2006/097526, WO 2007/008684, WO 2007/008704, WO 2007/009894, WO 2008/025094, and WO 2009/061411. Melanocortin receptor-specific cyclic peptides disclosed in the foregoing are typically cyclized through a lactam bridge formed by the side chains of Asp (aspartic acid) and Lys (lysine), or alternatively through a disulfide bridge formed by the side chains of two Cys (cysteine) or other reactive thiol-containing residues.

Notwithstanding the intense scientific and pharmaceutical interest in melanocortin receptor-specific peptides, evidenced by numerous articles in the scientific literature and numerous patent applications and issued patents, no melanocortin receptor-specific peptide has been approved as a drug for any therapeutic indication. Indeed, there are no reports of any melanocortin receptor-specific peptide for any therapeutic indication having advanced past Phase II clinical trials. There remains a significant and substantial need for melanocortin receptor-specific peptides for use in pharmaceutical applications. It is against this background that the present invention was made.

BRIEF SUMMARY OF THE INVENTION

In one aspect, the present invention relates to a cyclic peptide of the structural formula (I):

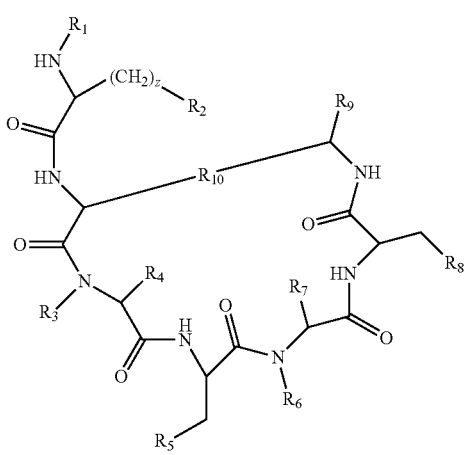

(I)

including all enantiomers, stereoisomers or diastereoisomers thereof, or a pharmaceutically acceptable salt of any of the foregoing,
wherein:
$R_1$ is H— or a $C_1$ to $C_7$ acyl group, wherein the $C_1$ to $C_7$ comprises a linear or branched alkyl or a cycloalkyl or both a linear alkyl and a cycloalkyl;
$R_2$ is —N($R_{15a}$)($R_{15b}$), —NH—($CH_2$)$_z$—N($R_{15a}$)($R_{15b}$), NH—C(=NH)—N($R_{15a}$)($R_{15b}$), C(=O)—N($R_{15a}$)($R_{15b}$) or NH—C(=O)—N($R_{15a}$)($R_{15b}$);
$R_3$ is —H, —$CH_3$ or —$CH_2$—, and if it is —$CH_2$— forms with $R_4$ a ring of the general structure

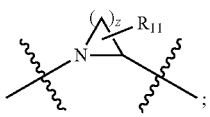

;

$R_4$ is —H, —($CH_2$)$_z$— if $R_3$ is —$CH_2$—, and if it is —($CH_2$)$_z$— forms the ring with $R_3$, provided that if $R_{11}$ is not H, then the carbon atom to which $R_{11}$ is bound is —CH—, or $R_4$ is —($CH_2$)$_w$—$R_{12}$—($CH_2$)$_w$—$R_{13}$, wherein any H in either ($CH_2$)$_w$ is optionally substituted with —($CH_2$)$_w$—$CH_3$, but, if $R_1$ is $CH_3$—(C=O)—, $R_5$ is unsubstituted phenyl, $R_6$ is H, $R_7$ is —($CH_2$)$_3$—NH—C(=NH)—$NH_2$, $R_8$ is indole, and $R_9$ is C(=O)—OH or C(=O)—$NH_2$, then excluding:
—($CH_2$)$_2$— but only if $R_3$ is —$CH_2$— and forms an unsubstituted pyrrolidine ring with $R_3$ and $R_{10}$ is —$CH_2$—C(=O)—NH—($CH_2$)$_4$, —($CH_2$)$_2$—C(=O)—NH—($CH_2$)$_3$ or —($CH_2$)$_3$—NH—C(=O)—($CH_2$)$_2$,

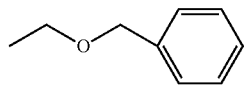

but only if $R_{10}$ is —$CH_2$—C(=O)—NH—($CH_2$)$_4$, —($CH_2$)$_2$—C(=O)—NH—($CH_2$)$_3$ or —($CH_2$)$_3$—NH—C(=O)—($CH_2$)$_2$, and

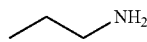

but only if $R_{10}$ is —$CH_2$—C(=O)—NH—($CH_2$)$_3$, —($CH_2$)$_2$—C(=O)—NH—($CH_2$)$_3$, —$CH_2$—C(=O)—NH—($CH_2$)$_4$ or —($CH_2$)—C(=O)—NH—($CH_2$)$_4$;
$R_5$ is unsubstituted phenyl or naphthyl;
$R_6$ is —H, —$CH_3$ or —$CH_2$—, and if it is —$CH_2$— forms with $R_7$ a ring of the general structure

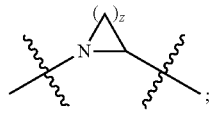

;

$R_7$ is —($CH_2$)$_z$— if $R_6$ is —$CH_2$—, and if it is —($CH_2$)$_z$— forms the ring with $R_6$, or $R_7$ is —($CH_2$)$_w$—$R_{14}$,
$R_8$ is

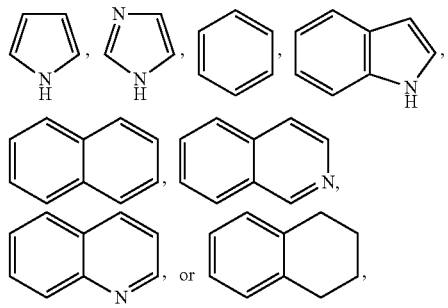

optionally substituted with one or more ring substituents, and when one or more are present, are the same or different and independently hydroxyl, halogen, sulfonamide, alkyl, —O-alkyl, aryl, or —O-aryl;
$R_9$ is H, —C(=O)—OH, —C(=O)—N($R_{15a}$)($R_{15b}$), —C(=O)—($CH_2$)$_w$-cycloalkyl or —C(=O)—$R_{16}$;
$R_{10}$ is
—($CH_2$)$_x$—C(=O)—NH—($CH_2$)$_y$—,
—($CH_2$)$_x$—NH—C(=O)—($CH_2$)$_y$,
—($CH_2$)$_x$—C(=O)—($CH_2$)$_z$—C(=O)—($CH_2$)$_y$—,
—($CH_2$)$_x$—C(=O)—NH—C(=O)—($CH_2$)$_y$—, or
—($CH_2$)$_x$—NH—C(=O)—NH—($CH_2$)$_y$—;
$R_{11}$ is —H or —$R_{12}$—($CH_2$)$_w$—$R_{13}$,
$R_{12}$ is optionally present, and if present is
—O—,
—S—,
—NH—,
—S(=O)$_2$—,
—S(=O)—,
—S(=O)$_2$—NH—,
—NH—S(=O)$_2$—, —C(=O)—,
—C(=O)—O—,
—O—C(=O)—,
—NH—C(=O)—O—,
—O—C(=O)—NH—,
—NH—C(=O)—, or
—C(=O)—NH—;

$R_{13}$ is H, —CH$_3$, —N(R$_{15a}$)(R$_{15b}$), —NH—(CH$_2$)$_z$—N(R$_{15a}$)(R$_{15b}$), —NH—CH(=NH)—N(R$_{15a}$)(R$_{15b}$), —NH—CH(=O)—N(R$_{15a}$)(R$_{15b}$), —O(R$_{15a}$), —(R$_{15a}$)(R$_{15b}$), —S(=O)$_2$(R$_{15a}$), —C(=O)—O(R$_{15a}$),

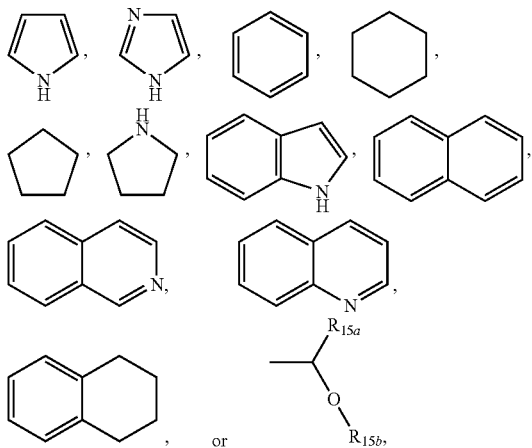

wherein any ring in $R_{13}$ is optionally substituted with one or more ring substituents, and when one or more are present, are the same or different and independently hydroxyl, halogen, sulfonamide, alkyl, —O-alkyl, aryl, —O-aryl, C(=O)—OH, or C(=O)—N(R$_{15a}$)(R$_{15b}$);

$R_{14}$ is H, —N(R$_{15a}$)(R$_{15b}$), —NH—(CH$_2$)$_z$—N(R$_{15a}$)(R$_{15b}$), —NH—CH(=NH)—N(R$_{15a}$)(R$_{15b}$), —NH—CH(=O)—N(R$_{15a}$)(R$_{15b}$), —O(R$_{15a}$), a linear or branched C$_1$ to C$_{17}$ alkyl chain, —C(=O)—N(R$_{15a}$)(R$_{15b}$), —S(=O)$_2$(R$_{15a}$),

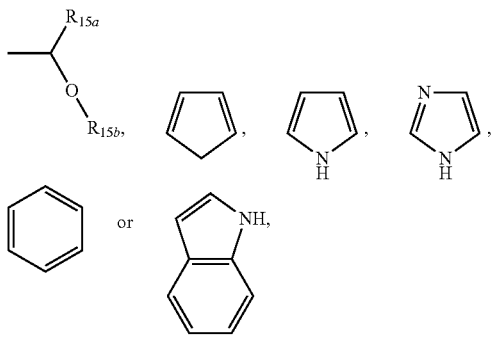

wherein any ring is optionally substituted with one or more optional ring substituents, and when one or more are present, are the same or different and independently hydroxyl, halogen, sulfonamide, alkyl, —O-alkyl, aryl, aralkyl, O-aralkyl, or —O-aryl;

$R_{15a}$ and $R_{15b}$ are each independently H or a C$_1$ to C$_4$ linear or branched alkyl chain;

$R_{16}$ is

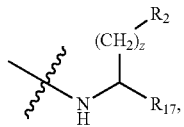

$R_{17}$ is H, —C(=O)—OH, or —C(=O)—N(R$_{15a}$)(R$_{15b}$);
w is in each instance independent 0 to 5;
x is 1 to 5;
y is 1 to 5; and
z is in each instance independently 1 to 5.

In another aspect there is provided the cyclic peptide of formula (I) wherein $R_{10}$ is —(CH$_2$)$_x$—C(=O)—NH—(CH$_2$)$_y$— where x is 4 and y is 3, where x is 3 and y is 2, or where x is 2 and y is 1. In an alternative aspect there is provided the cyclic peptide of formula (I) wherein $R_{10}$ is —(CH$_2$)$_x$—NH—C(=O)—(CH$_2$)$_y$— where x is 1 and y is 2, where x is 2 and y is 3, or where x is 3 and y is 4.

In another aspect there is provided the cyclic peptide of formula (I) wherein z is three and $R_2$ is NH—C(=NH)—NH$_2$.

In another aspect there is provided the cyclic peptide of formula (I) wherein $R_{16}$ is

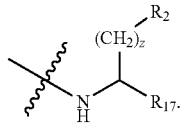

In another aspect there is provided the cyclic peptide of formula (I) wherein $R_{16}$ is

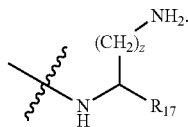

In such cyclic peptide $R_{17}$ may optionally be —C(=O)—OH or —C(=O)—NH$_2$.

In another aspect there is provided the cyclic peptide of formula (I) wherein $R_3$ forms with $R_4$ a ring of the general structure

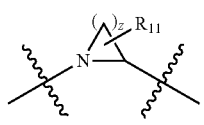

where z is 3.

In another aspect there is provided a cyclic heptapeptide of formula (II)

$$Z\text{-}Xaa^1\text{-}Xaa^2\text{-}Xaa^3\text{-}Xaa^4\text{-}Xaa^5\text{-}Xaa^6\text{-}Xaa^7\text{-}Y \quad (II)$$

or a pharmaceutically acceptable salt thereof, wherein:
Z is H or an N-terminal group;
Xaa$^1$ is an amino acid with a side chain including at least one primary amine, guanidine or urea group;
Xaa$^2$ and Xaa$^7$ are amino acids wherein the side chains thereof form a lactam-containing cyclic bridge;

Xaa³ is Pro, optionally substituted with hydroxyl, halogen, sulfonamide, alkyl, —O-alkyl, aryl, alkyl-aryl, alkyl-O-aryl, alkyl-O-alkyl-aryl, or —O-aryl, or Xaa³ is an amino acid with a side chain including at least one primary amine, secondary amine, alkyl, cycloalkyl, cycloheteroalkyl, aryl, heteroaryl, ether, sulfide, or carboxyl;

Xaa⁴ is an amino acid with a side chain including unsubstituted phenyl or naphthyl;

Xaa⁵ is Pro or Xaa⁵ is an amino acid with a side chain including at least one primary amine, secondary amine, guanidine, urea, alkyl, cycloalkyl, cycloheteroalkyl, aryl, heteroaryl, or ether;

Xaa⁶ is an amino acid with a side chain including at least one aryl or heteroaryl, optionally substituted with one or more ring substituents, and when one or more are present, are the same or different and independently hydroxyl, halogen, sulfonamide, alkyl, —O-alkyl, aryl, or —O-aryl; and Y is a C-terminal group;

but excluding cyclic peptides wherein Z is Ac, Xaa¹ is Arg, Xaa² and Xaa⁷ together are Glu . . . Orn, Orn . . . Glu, or Asp . . . Lys, Xaa³ is Pro or Ser(Bzl), Xaa⁴ is D-Phe, Xaa⁵ is Arg, Xaa⁶ is Trp, and Y is —OH or —NH₂.

In another aspect there is provided the cyclic peptide of formula (II) wherein Xaa¹ is Dap, Dab, Orn, Lys, Cit or Arg.

In another aspect there is provided the cyclic peptide of formula (II) wherein Xaa⁴ is D-Phe.

In another aspect there is provided the cyclic peptide of formula (II) wherein one of Xaa² and Xaa⁷ is Asp, hGlu or Glu and the other of Xaa² and Xaa⁷ is Lys, Orn, Dab or Dap.

In another aspect there is provided the cyclic peptide of formula (II) wherein the N-terminal group is a $C_1$ to $C_7$ acyl group, a linear or branched $C_1$ to $C_{17}$ alkyl, aryl, heteroaryl, alkene, alkenyl, or aralkyl chain or an N-acylated linear or branched $C_1$ to $C_{17}$ alkyl, aryl, heteroaryl, alkene, alkenyl, or aralkyl chain.

In another aspect there is provided the cyclic peptide of formula (II) wherein Y is a hydroxyl, an amide, an amide substituted with one or two linear or branched $C_1$ to $C_{17}$ alkyl, cycloalkyl, aryl, alkyl cycloalkyl, aralkyl, heteroaryl, alkene, alkenyl, or aralkyl chains.

In another aspect, the present invention provides a melanocortin receptor-specific peptide-based pharmaceutical composition for use in treatment of melanocortin receptor-mediated diseases, indications, conditions and syndromes.

In another aspect, the present invention provides a peptide-based melanocortin receptor-specific pharmaceutical, wherein the peptide is a selective MC4-R ligand, for use in treatment of sexual dysfunction and other MC4-R associated disorders.

In another aspect, the present invention provides peptides which are specific for melanocortin receptor MC4-R and which are agonists.

In another aspect, the present invention provides a peptide-based melanocortin receptor-specific pharmaceutical for use in treatment of obesity, modulation of feeding behavior and other energy homeostasis disorders.

In another aspect, the present invention provides a specific MC4-R cyclic peptide that is effective over a significant dose range.

Other aspects and novel features, and the further scope of applicability of the present invention will be set forth in part in the detailed description to follow, and in part will become apparent to those skilled in the art upon examination of the following, or may be learned by practice of the invention. The aspects of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention.

Figure 1:
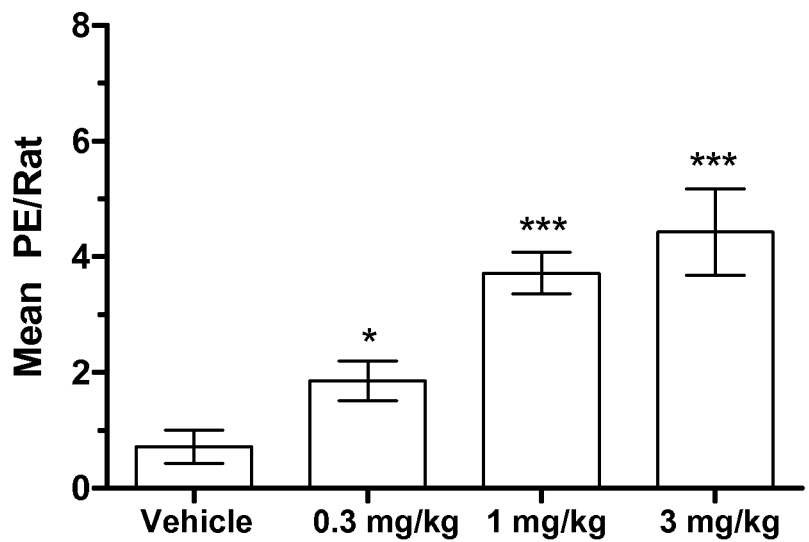
FIG. 1 is a bar graph of the mean number of penile erections per rat in a 60 minute observation period following administration of the indicated doses of peptide No. 154, with a vehicle control, where "*" indicates a p value of less than 0.05 and "***" indicates a p value of less than 0.01.

DETAILED DESCRIPTION OF THE INVENTION 1.0 Definitions

Before proceeding with the description of the invention, certain terms are defined as set forth herein.

In the sequences given for the peptides according to the present invention, the amino acid residues have their conventional meaning as given in Chapter 2400 of the *Manual of Patent Examining Procedure*, 8th Ed. Thus, "Ala" is alanine, "Asn" is asparagine, "Asp" is aspartic acid, "Arg" is arginine, "Cys" is cysteine, "Gly" is glycine, "Gln" is glutamine, "Glu" is glutamic acid, His is histidine, "Ile" is isoleucine, "Leu" is leucine, "Lys" is lysine, "Met" is methionine, "Phe" is phenylalanine, "Pro" is proline, "Ser" is serine, "Thr" is Threonine, "Trp" is tryptophan, "Tyr" is tyrosine, and "Val" is valine, and so on. It is to be understood that "D" isomers are designated by a "D-" before the three letter code or amino acid name, such that for example D-Phe is D-phenylalanine. Amino acid residues not encompassed by the foregoing have the following definitions:

| Abbreviation | Common Name | Side Chain or Amino Acid Structure |
|---|---|---|
| Aib | alpha-aminoisobutyric acid | $H_3C$ $CH_3$ $H_2N$ —COOH |
| Aic | 2-aminoindane-2-carboxylic acid | (indane structure with $H_2N$ and COOH) |

| Abbreviation | Common Name | Side Chain or Amino Acid Structure |
|---|---|---|
| Cit | citruline | -(CH₂)₃-NH-C(=O)-NH₂ |
| Dab | diaminobutyric acid | -(CH₂)₂-NH₂ |
| Dab(Acetyl) | 2-amino, 4-acetyl-aminobutyric acid | -(CH₂)₂-NH-C(=O)-CH₃ |
| Dab(betaPro) | 2-amino, 4-(beta-prolyl)aminobutyric acid | -(CH₂)₂-NH-C(=O)-(3-pyrrolidinyl) |
| Dab(Glycyl) | 2-amino, 4-(glycyl)aminobutyric acid | -(CH₂)₂-NH-C(=O)-CH₂-NH₂ |
| Dap | diaminoproprionic acid | -CH₂-NH₂ |
| hGlu | homoglutamic acid | -(CH₂)₃-COOH |
| Hyp | hydroxyproline | 4-hydroxyproline structure |
| Hyp(Bzl) | O-benzyl-hydroxyproline | 4-benzyloxyproline structure |
| Met(O₂) | Methionine sulfone | -(CH₂)₂-S(=O)₂-CH₃ |
| Met(=O) | Methionine sulfoxide | -(CH₂)₂-S(=O)-CH₃ |
| Nal 1 | 3-(1-naphthyl)alanine | -CH₂-(1-naphthyl) |
| Nal 2 | 3-(2-naphthyl)alanine | -CH₂-(2-naphthyl) |
| Nle | norleucine | -(CH₂)₃-CH₃ |
| Orn | ornithine | -(CH₂)₃-NH₂ |
| Phe(2-C(=O)-NH₂) | 2-carbamoyl-phenylalanine | -CH₂-(2-carbamoylphenyl) |
| Phe(3-C(=O)-NH₂) | 3-carbamoyl-phenylalanine | -CH₂-(3-carbamoylphenyl) |
| Phe(4-C(=O)-NH₂) | 4-carbamoyl-phenylalanine | -CH₂-(4-carbamoylphenyl) |
| Pro(4R-Bzl) | 4(R)benzyl-proline | 4(R)-benzyl-proline structure |
| Pro(4R-NH₂) | 4(R)amino-proline | 4(R)-amino-proline structure |
| Sar | sarcosine | CH₃-NH-CH₂-COOH |

| Abbreviation | Common Name | Side Chain or Amino Acid Structure |
|---|---|---|
| Ser(Bzl) | O-benzyl-serine | 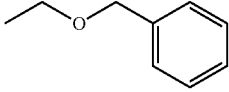 |
| Thr(Bzl) | O-benzyl-threonine | 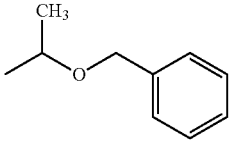 |

An "α,α-disubstituted amino acid" means any α-amino acid having a further substituent in the α-position, which substituent may be the same as or different from the side chain moiety of the α-amino acid. Suitable substituents, in addition to the side chain moiety of the α-amino acid, include $C_1$ to $C_6$ linear or branched alkyl. Aib is an example of an α,α-disubstituted amino acid. While α,α-disubstituted amino acids can be referred to using conventional L- and D-isomeric references, it is to be understood that such references are for convenience, and that where the substituents at the α-position are different, such amino acid can interchangeably be referred to as an α,α-disubstituted amino acid derived from the L- or D-isomer, as appropriate, of a residue with the designated amino acid side chain moiety. Thus (S)-2-Amino-2-methylhexanoic acid can be referred to as either an α,α-disubstituted amino acid derived from L-Nle or as an α,α-disubstituted amino acid derived from D-Ala. Similarly, Aib can be referred to as an α,α-disubstituted amino acid derived from Ala. Whenever an α,α-disubstituted amino acid is provided, it is to be understood as including all (R) and (S) configurations thereof. Whenever a claim or description herein refers to an "amino acid", such designation includes, but is not limited to, an "α,α-disubstituted amino acid."

An "N-substituted amino acid" means any amino acid wherein an amino acid side chain moiety is covalently bonded to the backbone amino group, including optionally where there are no substituents other than H in the α-carbon position. Sarcosine is an example of an N-substituted amino acid. By way of example, sarcosine can be referred to as an N-substituted amino acid derivative of Ala, in that the amino acid side chain moiety of sarcosine and Ala is the same, methyl. Whenever a claim or description herein refers to an "amino acid", such designation includes, but is not limited to, an "N-substituted amino acid."

The term "alkane" includes linear or branched saturated hydrocarbons. Examples of linear alkane groups include methane, ethane, propane, and the like. Examples of branched or substituted alkane groups include methylbutane or dimethylbutane, methylpentane, dimethylpentane or trimethylpentane, and the like. In general, any alkyl group may be a substituent of an alkane.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkyne" includes a linear monovalent hydrocarbon radical of two to six carbon atoms or a branched monovalent hydrocarbon radical of three to six carbon atoms containing at least one triple bond; examples thereof include ethyne, propyne, butyne, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkylthio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —$R^aR^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group R(C=O)—, where R is an organic group, such as an alkyl, aryl, heteroaryl, carbocyclyl or heterocyclyl. Thus, when reference is made herein to a substituted acyl group, it means that said organic group (R) is substituted. The acetyl group $CH_3$—C(=O)—, referred to herein as "Ac", is non-limiting example of an acyl.

A peptide or aliphatic moiety is "acylated" when an alkyl or substituted alkyl group as defined above is bonded through one or more carbonyl {—(C=O)—} groups. A peptide is most usually acylated at the N-terminus.

An "omega amino aliphatic chain" includes an aliphatic moiety with a terminal amino group. Examples of omega amino aliphatic chains include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

As used herein, the term "amide" includes compounds that have a trivalent nitrogen attached to a carbonyl group, i.e. —C(=O)—$NH_2$ (i.e. primary amide), —C(=O)—$NHR_c$ and —C(=O)—$NR_cR_d$, wherein each of $R_c$ and $R_d$ independently represents an organic group. When reference is made herein to a substituted amide group, it means that at least one of said organic groups ($R_c$ and $R_d$) is substituted. Examples of amides include methylamide, ethylamide, propylamide, and the like.

An "amine" includes an amino group (—$NH_2$), —$NHR_a$ and —$NR_aR_b$, wherein each of $R_a$ and $R_b$ independently represents an organic group. When reference is made herein to a substituted amine group, it means that at least one of the organic groups ($R_a$ and $R_b$) is substituted.

An "imide" includes compounds containing an imido group (—C(=O)—NH—C(=O)—).

A "nitrile" includes compounds that contain a (—CN) group bound to an organic group.

The term "halogen" is intended to include the halogen atoms fluorine, chlorine, bromine and iodine, and groups including one or more halogen atoms, such as —$CF_3$ and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions utilized in the present invention encompass any composition made by admixing an active ingredient and one or more pharmaceutically acceptable carriers.

By a melanocortin receptor "agonist" is meant an endogenous substance, drug substance or compound, including a compound such as the peptides of the present invention, which can interact with a melanocortin receptor and initiate a pharmacological response, including but not limited to adenyl cyclase activation, characteristic of the melanocortin receptor. For the present invention, a melanocortin receptor agonist which is an agonist at melanocortin-4 receptor (MC4-R) is preferred, but for certain applications, a melanocortin receptor agonist which is an agonist at both MC4-R and melanocortin-1 receptor (MC1-R) is preferred, and for other applications a melanocortin receptor agonist which is an agonist at one or more of MC1-R, melanocortin-3 receptor (MC3-R), MC4-R and melanocortin-5 receptor (MC5-R) is preferred.

By "α-MSH" is meant the peptide Ac-Ser-Tyr-Ser-Met-Glu-His-Phe-Arg-Trp-Gly-Lys-Pro-Val-$NH_2$ (SEQ ID NO:2) and analogs and homologs thereof, including without limitation NDP-α-MSH.

By "NDP-α-MSH" is meant the peptide Ac-Ser-Tyr-Ser-Nle-Glu-His-D-Phe-Arg-Trp-Gly-Lys-Pro-Val-$NH_2$ and analogs and homologs thereof.

By "$EC_{50}$" is meant the molar concentration of an agonist, including a partial agonist, which produced 50% of the maximum possible response for that agonist. By way of example, a test compound which, at a concentration of 72 nM, produces 50% of the maximum possible response for that compound as determined in a cAMP assay in an MC4-R cell expression system has an $EC_{50}$ of 72 nM. Unless otherwise specified, the molar concentration associated with an $EC_{50}$ determination is in nanomoles per liter (nM).

By "Ki (nM)" is meant the equilibrium inhibitor dissociation constant representing the molar concentration of a competing compound that binds to half the binding sites of a receptor at equilibrium in the absence of radioligand or other competitors. In general, the numeric value of the Ki is inversely correlated to the affinity of the compound for the receptor, such that if the Ki is low, the affinity is high. Ki may be determined using the equation of Cheng and Prusoff (Cheng Y., Prusoff W. H., *Biochem. Pharmacol.* 22, 3099-3108, 1973):

$$Ki = \frac{EC_{50}}{1 + \frac{[ligand]}{K_D}}$$

where "ligand" is the concentration of radioligand and $K_D$ is an inverse measure of receptor affinity for the radioligand which produces 50% receptor occupancy by the radioligand. Unless otherwise specified, the molar concentration associated with a Ki determination is in nM. Ki may be expressed in terms of specific receptors (e.g., MC1-R, MC3-R, MC4-R or MC5-R) and specific ligands (e.g., α-MSH or NDP-α-MSH).

By "inhibition" is meant the percent attenuation, or decrease in receptor binding, in a competitive inhibition assay compared to a known standard. Thus, by "inhibition at 1 µM (NDP-α-MSH)" is meant the percent decrease in binding of NDP-α-MSH by addition of a determined amount of the compound to be tested, such as 1 µM of a test compound, such as under the assay conditions hereafter described. By way of example, a test compound that does not inhibit binding of NDP-α-MSH has a 0% inhibition, and a test compound that completely inhibits binding of NDP-α-MSH has a 100% inhibition. Typically, as described hereafter, a radio assay is used for competitive inhibition testing, such as with $I^{125}$-labeled NDP-α-MSH, or a lanthanide chelate fluorescent assay, such as with Eu-NDP-α-MSH. However, other methods of testing competitive inhibition are known, including use of label or tag systems other than radioisotopes, and in general any method known in the art for testing competitive inhibition may be employed in this invention. It may thus be seen that "inhibition" is one measure to determine whether a test compound attenuates binding of α-MSH to melanocortin receptors.

By "binding affinity" is meant the ability of a compound or drug to bind to its biological target, expressed herein as Ki (nM).

By "intrinsic activity" is meant the maximal functional activity achievable by a compound in a specified melanocortin receptor expressing cell system, such as the maximal stimulation of adenylyl cyclase. The maximal stimulation achieved by α-MSH or NDP-α-MSH is designated as an intrinsic activity of 1.0 (or 100%) and a compound capable of stimulating half the maximal activity that of α-MSH or NDP-α-MSH is designated as having an intrinsic activity of 0.5 (or 50%). A compound of this invention that under assay conditions described herein has an intrinsic activity of 0.7 (70%) or higher is classified as an agonist, a compound with intrinsic activity between 0.1 (10%) and 0.7 (70%) is classified as a partial agonist, and a compound with intrinsic activity below 0.1 (10%) is classified as inactive or having no intrinsic activity. In one aspect, the cyclic peptides of the present invention may generally be characterized as a partial agonist at MC4-R with respect to α-MSH or NDP-α-MSH.

In general, "functional activity" is a measure of the signaling of a receptor, or measure of a change in receptor-associated signaling, such as a melanocortin receptor, and in particular MC4-R or hMC4-R, upon activation by a compound. Melanocortin receptors initiate signal transduction through activation of heterotrimeric G proteins. In one aspect, melanocortin receptors signal through $Gα_S$, which catalyzes production of cAMP by adenylyl cyclase. Thus determination of stimulation of adenylyl cyclase, such as determination of maximal stimulation of adenylyl cyclase, is one measure of functional activity, and is the primary measure exemplified herein. However, it is to be understood that alternative measures of functional activity may be employed in the practice of this invention, and are specifically contemplated and included within the scope of this invention. Thus, in one example intracellular free calcium may be measured, such as reported by and using the methods disclosed in Mountjoy K. G. et al., Melanocortin receptor-mediated mobilization of intracellular free calcium in HEK293 cells. *Physiol Genom-* ics 5:11-19, 2001, or Kassack M. U. et al., Functional screening of G protein-coupled receptors by measuring intracellular calcium with a fluorescence microplate reader. *Biomol Screening* 7:233-246, 2002. It is also possible to measure activation by measurement of the production of inositol triphosphate or diacylglycerol from phosphatidylinositol 4,5-biphosphate, such as by use of radioassays. Yet another measure of functional activity is receptor internalization, resulting from activation of regulatory pathways, such as using the methods disclosed in Nickolls S. A. et al., Functional selectivity of melanocortin 4 receptor peptide and nonpeptide agonists: evidence for ligand specific conformational states. *J Pharm Exper Therapeutics* 313:1281-1288, 2005. Yet another measure of functional activity is the exchange, and exchange rate, of nucleotides associated with activation of a G protein receptor, such as the exchange of GDP (guanosine diphosphate) for GTP (guanosine triphosphase) on the G protein α subunit, which may be measured by any number of means, including a radioassay using guanosine 5'-(γ-[$^{35}$S]thio)-triphosphate, as disclosed in Manning D. R., Measures of efficacy using G proteins as endpoints: differential engagement of G proteins through single receptors. *Mol Pharmacol* 62:451-452, 2002. Various gene-based assays have been developed for measuring activation of G-coupled proteins, such as those disclosed in Chen W. et al., A colorimetric assay from measuring activation of Gs- and Gq-coupled signaling pathways. *Anal Biochem* 226:349-354, 1995; Kent T. C. et al., Development of a generic dual-reporter gene assay for screening G-protein-coupled receptors. *Biomol Screening*, 5:437-446, 2005; or Kotarsky K. et al., Improved receptor gene assays used to identify ligands acting on orphan seven-transmembrane receptors. *Pharmacology & Toxicology* 93:249-258, 2003. The colorimetric assay of Chen et al. has been adapted for use in measuring melanocortin receptor activation, as disclosed in Hruby V. J. et al., Cyclic lactam α-melanocortin analogues of Ac-Nle$^4$-cyclo[Asp$^5$,D-Phe$^7$, Lys$^{10}$]α-melanocyte-stimulating hormone-(4-10)-NH$_2$ with bulky aromatic amino acids at position 7 shows high antagonist potency and selectivity at specific melanocortin receptors. *J Med Chem* 38:3454-3461, 1995. In general, functional activity may be measured by any method, including methods of determining activation and/or signaling of a G-coupled receptor, and further including methods which may be hereafter developed or reported. Each of the foregoing articles, and the methods disclosed therein, is incorporated here by reference as if set forth in full.

The terms "treat," "treating" and "treatment," as used herein, contemplate an action that occurs while a patient is suffering from the specified disease or disorder, which reduces the severity of the disease or disorder.

As used herein, the term "pharmacologically effective amount" (including "therapeutically effective amount") means an amount of a peptide according to the invention that is sufficient to induce a desired therapeutic or biological effect.

As used herein, the term "therapeutically effective amount" means the amount of a compound including a peptide of the invention that will elicit a biological or medical response in the mammal that is being treated by a medical doctor or other clinician.

As used herein, the term "prophylactically effective" or "preventive" means the amount of a compound including a peptide of the invention that will prevent or inhibit affliction or mitigate affliction of a mammal with a medical condition that a medical doctor or other clinician is trying to prevent, inhibit, or mitigate before a patient begins to suffer from the specified disease or disorder.

The term "obesity" means the condition of excess body fat (adipose tissue), including by way of example in accordance with the National Institutes of Health Federal Obesity Clinical Guidelines for adults, whereby body mass index calculated by dividing body mass in kilograms by height in meters squared is equal to or greater than twenty-five (25), and further including an overweight condition and comparable obesity and overweight condition in children.

The term "diabetes" includes type 1 diabetes, which is insulin-dependent diabetes mellitus as diagnosed according to criteria published in the Report of the Expert Committee on the Diagnosis and Classification of Diabetes Mellitus (*Diabetes Care*, Vol. 24, Supp. 1, January 2001) whereby fasting plasma glucose level is greater than or equal to 126 milligrams per deciliter and for which the primary cause is pancreatic beta cell destruction, type 2 diabetes, which is non-insulin-dependent diabetes mellitus as diagnosed according to criteria published in the Report of the Expert Committee on the Diagnosis and Classification of Diabetes Mellitus whereby fasting plasma glucose level is greater than or equal to 126 milligrams per deciliter, and latent autoimmune diabetes mellitus of adults.

The term "metabolic syndrome" refers to metabolic disorders, particularly glucose and lipid regulatory disorders, including insulin resistance and defective secretion of insulin by pancreatic beta cells, and may further include conditions and states such as abdominal obesity, dyslipidemia, hypertension, glucose intolerance or a prothrombitic state, and which may further result in disorders such as hyperlipidemia, obesity, diabetes, insulin resistance, glucose intolerance, hyperglycemia, and hypertension.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, female sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity.

Sexual anhedonia can be caused by depression, drugs, or interpersonal factors. Female sexual arousal disorder can be caused by reduced estrogen, illness, treatment with diuretics, antihistamines, antidepressants, or antihypertensive agents and other factors. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

By "circulatory shock" is meant the general medical condition in which organs and/or tissues of the body of the subject, which subject may be human or animal, are not receiving an adequate flow of blood. Circulatory shock includes conditions such as hypovolemic shock, cardiogenic shock, vasodilatory shock and the like. These conditions or dysfunctions in circulation can in turn have different causes, such as bacterial blood infection (septic shock or infectious), severe allergic reaction (anaphylactic shock), trauma (traumatic shock), severe bleeding or loss of blood (hemorrhagic shock), neurologic dysfunction causing abnormal opening of blood vessels (neurogenic shock) or endocrine related (endocrine shock). Circulatory shock can further result in ischemia and ischemic damage to bodily organs, tissues, cells or parts. Upon reperfusion, or restoration of blood flow, ischemia-reperfusion injury can occur, also resulting in damage to bodily organs, tissues, or cells.

By "inflammatory disease," also sometimes called an "inflammatory condition," is meant a disease or condition characterized in part by inflammatory mechanisms, such as specific T lymphocyte reactions or antibody-antigen interactions causing the recruitment of inflammatory cells and endogenous mediator chemicals, including but not limited to cytokines, which mediator chemicals include but are not limited to one or more of increased NF-κB activity, increased TNF-α production, increased IL-1 production and increased IL-6 production.

By "Stage I shock," also sometimes called "compensated shock" or "non-progressive shock," is meant a condition which occurs when the body detects decreased blood flow or perfusion and begins to activate one or more of several reactive mechanisms to restore perfusion or direct blood flow to the most vital body organs. Stage I shock can be asymptomatic, but may also include, but is not limited to, symptoms such as low blood flow or perfusion, rapid or increased heart rate, shallow or irregular breathing, hypotension, hypertension, pallor and cyanosis.

By "Stage II shock," also sometimes called "decompensated shock" or "progressive shock," is mean a condition which occurs when the compensatory mechanisms of the body begin to fail and organ perfusion cannot be restored to normal or maintained. Symptoms of Stage II shock include, but are not limited to, confusion, anxiety, disorientation and other mental disturbances indicating a lack of oxygen to the brain, chest pains, increased heart rate, oliguria, multiple organ dysfunction, falling blood pressure (hypotension), rapid breathing, weakness and pupil dilation.

By "Stage III shock," also sometimes called "irreversible shock," is meant a condition which occurs after the state of decreased perfusion or blood flow has existed to such an extent that the organs and tissues of the body are permanently affected. Such symptoms include, but are not limited to, multiple organ failure, kidney failure, coma, blood pooling in the extremities and death.

2.0 Clinical Indications and Utility

The compositions and methods disclosed herein can be used for both medical applications and animal husbandry or veterinary applications. Typically, the methods are used in humans, but may also be used in other mammals. The term "patient" is intended to denote a mammalian individual, and is so used throughout the specification and in the claims. The primary applications of the present invention involve human patients, but the present invention may be applied to laboratory, farm, zoo, wildlife, pet, sport or other animals. Clinical indications and specific utilities include the following:

2.1 Obesity and Related Metabolic Syndrome.

Peptides of formula (I) and (II) have been found to be ligands of the MC4 receptor. Such peptides are believed to be useful in treating diseases, disorders and/or conditions responsive to modulation of the MC4-R function, more particularly activation of the MC4-R, i.e. diseases, disorders and/or conditions which would benefit from agonism (including full or partial agonism) at the MC4-R, including energy homeostasis and metabolism related (such as diabetes, in particular type 2 diabetes; dyslipidemia; fatty liver; hypercholesterolemia; hypertriglyceridemia; hyperuricacidemia; impaired glucose tolerance; impaired fasting glucos; insulin resistance syndrome; and metabolic syndrome), food intake related (such as hyperphagia; binge eating; bulimia; and compulsive eating) and/or energy balance and body weight related diseases, disorders and/or conditions, more particularly such diseases, disorders and conditions characterized by excess body weight and/or excess food intake.

Such peptides are particularly believed to be useful for treatment of body weight related diseases, disorders and/or conditions characterized by excess body weight, including obesity and overweight (by promotion of weight loss, maintenance of weight loss, and/or prevention of weight gain, including medication-induced weight gain or weight gain subsequent to cessation of smoking), and diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

It will be understood that there are medically accepted definitions of obesity and overweight. A patient may be identified by, for example, measuring body mass index (BMI), which is calculated by dividing weight in kilograms by height in meters squared, and comparing the result with the definitions. The recommended classifications for BMI in humans, adopted by the Expert Panel on the Identification, Evaluation and Treatment of Overweight and Obesity in Adults, and endorsed by leading organizations of health professionals, are as follows: underweight <18.5 kg/m$^2$, normal weight 18.5-24.9 kg/m$^2$, overweight 25-29.9 kg/m$_2$, obesity (class 1) 30-34.9 kg/m$^2$, obesity (class 2) 35-39.9 kg/m$^2$, extreme obesity (class 3)≥40 kg/m$^2$ (Practical Guide to the Identification, Evaluation, and Treatment of Overweight and Obesity in Adults, The North American Association for the Study of Obesity (NAASO) and the National Heart, Lung and Blood Institute (NHLBI) 2000). Modifications of this classification may be used for specific ethnic groups. Another alternative for assessing overweight and obesity is by measuring waist circumference. There are several proposed classifications and differences in the cutoffs based on ethnic group. For instance, according to the classification from the International Diabetes Federation, men having waist circumferences above 94 cm (cut off for europids) and women having waist circumferences above 80 cm (cut off for europids) are at higher risk of diabetes, dyslipidemia, hypertension and cardiovascular diseases because of excess abdominal fat. Another classification is based on the recommendation from the Adult Treatment Panel III where the recommended cut-offs are 102 cm for men and 88 cm for women. However, the peptides of formula (I) or (II) may also be used for reduction of self-diagnosed overweight and for decreasing the risk of becoming obese due to life style, genetic considerations, heredity and/or other factors.

2.2 Sexual Dysfunction.

Peptides, compositions and methods of the present invention may be employed for the treatment of sexual dysfunction, including both male erectile dysfunction and female sexual dysfunction. In one particular embodiment, the peptides, compositions and methods of the present invention are used in male patients to increase erectile function, including but not limiting to increasing erectile function so as to permit vaginal intercourse. In another particular embodiment, the peptides, compositions and methods of the present invention are used to treat female sexual dysfunction, including but not limited to an increase in arousal success rate, desire success rate, levels of arousal and desire. For female sexual dysfunction, endpoints may, but need not, be determined by any of a number of validated instruments, including but not limited to the Female Sexual Distress Scale, Female Sexual Encounter Profile, Female Sexual Function Index, and Global Assessment Questionnaire. Patients treated for female sexual dysfunction may be premenopausal women or postmenopausal women.

2.3 Circulatory Shock and Related Diseases, Indications, Conditions and Syndromes.

Peptides, compositions and methods of the present invention may be employed for the treatment of circulatory shock in a subject. The compositions and methods provided herein may be employed to treat Stage I shock, Stage II shock or Stage III shock. In one particular embodiment, the methods of the present invention are used to treat the initial stage of shock, which initial stage of shock is characterized by cardiac output insufficient to meet the body's metabolic needs, but not otherwise low enough to produce significant symptoms. The patient may be anxious and alert, with increased respiration.

The invention provides compositions for use and methods of treating or preventing hemorrhagic shock in a patient, which include administering a composition including one or more of the peptides of the present invention to a patient diagnosed as suffering from blood loss. The blood loss may, but need not, be measured as a percentage of the subject's blood volume, such as, for example, a blood loss of greater than about 15% total blood volume, or greater than 20%, 25%, 30%, 35%, 40%, or 50% of the subject's total volume. Alternatively, the blood loss may, but need not, be measured in terms of a drop in blood volume in any amount sufficient to cause hemorrhagic shock in a particular subject, such as, for example, a loss of about 750 mL, 1000 mL, of about 1500 mL, or of about 2000 mL or more in a human subject. The blood loss may also be measured in terms of a drop in systolic blood pressure, such as, for example, a drop in systolic blood pressure that is about 20 mm Hg, 30 mm Hg, 40 mm Hg, 50 mm Hg, 60 mm Hg, 70 mm Hg, 80 mm Hg, 90 mm Hg or 100 mm Hg or more than 100 mm Hg lower than the subject's normal systolic blood pressure. In particular embodiments, the subject is undergoing or has undergone a medical procedure, such as, but not limited to, surgery, a transfusion or child birth. In other particular embodiments, the subject has suffered a traumatic injury, such as, but not limited to, resulting from a motor vehicle accident, from an industrial injury, or from a gunshot wound.

In additional embodiments of the present invention, the compositions and methods are used to treat cardiogenic shock, hypovolemic shock and vasodilatory shock, each of which can be in any of the aforementioned stages of shock. In one particular embodiment of the present invention, the methods are used to treat cardiogenic shock. Cardiogenic shock is, generally speaking, low blood flow or perfusion that is caused by heart malfunction where the heart does not pump adequate blood. Causes can include any condition that interferes with ventricular filling or emptying, such as, but not limited to, embolism, ischemia, regurgitation and valve malfunction. In another particular embodiment of the present invention, the methods are used to treat vasodilatory shock. Vasodilatory shock is caused by severe venous or arteriolar dilation, which results in inadequate blood flow. Several known causes contribute to vasodilatory shock including, but not limited to, cerebral trauma, drug or poison toxicity, anaphylaxis, liver failure, bacteremia and sepsis. In another more particular embodiment of the present invention, the methods are used to treat shock resulting from sepsis or bacteremia. In an even more particular embodiment, the compositions and methods are used to treat septic shock or bacteremic shock in Stage I, II or III. In yet another embodiment, the compositions and methods of the present invention are used to treat hypovolemic shock. Hypovolemic shock is, generally speaking, decreased intravascular volume, which decrease in intravascular volume can be relative or absolute. Hemorrhage from conditions such as, but not limited to, ulcers, gastrointestinal injury, trauma, accidents, surgery, and aneurysm may cause hypovolemic shock; but loss of other body fluids may also cause hypovolemic shock. For instance, renal fluid loss, intravascular fluid loss, water or other peritoneal fluid loss may contribute to hypovolemic shock. In one particular embodiment of the present invention, the compositions and methods, including administration of one or more of the peptides of the present invention, are used to treat hypovolemic shock. In an even more particular embodiment, the compositions and methods are used to treat hypovolemic shock in Stage I, Stage II or Stage III.

Circulatory shock, including hemorrhagic shock, may also result from partially controlled or uncontrolled bleeding within one or more internal organs or vessels of a patient. Bleeding may result from any cause, including by way of example from a ruptured aneurysm, dissected aorta, an ulcer, trauma or other gastrointestinal bleeding. In some instances the patient exhibits signs of circulatory shock or hypovolemia, which may include hypotension, but the source of internal bleeding is unknown.

In one embodiment, the invention is directed to methods of using one or more of the peptides of the present invention to protect the heart, brain or other organs of a patient against injury caused by circulatory shock. The protective effect against circulatory shock occurs instantaneously or within a short time period following administration of a composition comprising one or more of the peptides of the present invention, preferably within at least about 40 minutes following administration, more preferably within 1-20 minutes, more preferably within 1-15 minutes, and most preferably within about 1-10 minutes.

2.4 Ischemia and Related Diseases, Indications, Conditions and Syndromes.

Ischemia refers to any decrease or stoppage in the blood supply to any bodily organ, tissue, cell, or part, particularly where that decrease or stoppage leads to or would likely lead to ischemic damage to the bodily organ, tissue, cell, or part. An "ischemic episode" refers to any transient or permanent period of ischemia. Ischemia may result from any constriction or obstruction of the vasculature, or may result from circulatory shock, such as hemorrhagic shock, hypovolemic shock, or the like. The decrease or lack of blood flow results in a decrease or lack of oxygen to the affected part of the body, and may also result in an increase of inflammatory disease mediator chemicals such as various cytokines and other substances. During certain surgical procedures such as cardiac surgery and organ transplantation, the flow of blood is stopped temporarily and then resumed (reperfusion), resulting in ischemia-reperfusion injury. During a heart attack, the blood that supplies the heart is stopped, also resulting in ischemia that can evolve into infarction. Current treatment to relieve heart attacks requires reperfusion of the ischemic area of the heart, such as by using thrombolytic drugs or coronary angioplasty.

The invention has particular application in prevention of injury due to renal ischemia, including lung injury secondary to renal ischemia, preventing or limiting ischemic heart injuries subsequent to a myocardial infarction, preventing or limiting ischemic brain injuries subsequent to a cardiovascular injury, including without limitation myocardial infarction, stroke or the like. Neuroprotection is provided by administration of a composition of the invention to a patient with cerebral ischemia or stroke, particularly patients who are concurrently hypotensive. The invention has further particular application in preventing or limiting ischemic organ damage in organ transplant, including transplant of the heart, kidney, liver, lungs, pancreas or small intestine. In one aspect, the pharmaceutical composition of the present invention may be utilized for perfusion of a transplant organ, which perfusion may be prior to, during or subsequent to transplant of the organ.

In one embodiment, the invention is directed to methods of using one or more of the peptides of the present invention to protect the heart, brain or other organs of a patient against injury caused by ischemia. The protective effect against ischemia occurs instantaneously or within a short time period following administration of a composition comprising one or more of the peptides of the present invention, preferably within at least about 40 minutes following administration, more preferably within 1-20 minutes, more preferably within 1-15 minutes, and most preferably within about 1-10 minutes.

Ischemia may also results from any of a variety of diseases or conditions, and in one embodiment the invention is directed to methods of using one or more of the peptides of the present invention to protect the organs of a patient against injury resulting from ischemia, which ischemia is caused by a disease or condition. Such disease or condition may include, by way of example and not limitation, atherosclerotic diseases such as atheromata with thrombosis, embolism from the heart or from blood vessel from any organ, vasospasm, hypotension due to heart disease, hypotension due to systemic disease including infection or allergic reactions, or hypotension resulting from administration, ingestion or other exposure to one or more toxic compounds or drugs. Ischemia may also be secondary ischemia, and in another embodiment the invention is directed to methods of using one or more of the peptides of the present invention to protect the organs of a patient against injury resulting from secondary ischemia. Such secondary ischemia may be secondary to a disease or condition such diabetes mellitus, hyperlipidemia, hyperlipoproteinemia, dyslipidemia Buerger's disease, also called thromboangiitis obliterans, Takayasu's arteritis, arteritis temporalis, Kawasaki disease, also called lymph node syndrome, mucocutaneous node disease, infantile polyarteritis, cardiovascular syphilis, and various connective tissue diseases and disorders.

2.5 Ischemia-Reperfusion Injury and Related Diseases, Indications, Conditions and Syndromes.

Ischemia-reperfusion is the interruption of blood flow to bodily tissue and the subsequent and often abrupt restoration of blood flow to the tissue. While restoration of blood flow following ischemia is essential to preserve functional tissue, the reperfusion itself is known to be harmful to the tissue. Both ischemia and reperfusion are known to be important contributors to tissue necrosis. Several mechanisms appear to play a causative role in the generation of tissue damage associated with ischemia-reperfusion injury.

Various methods of limiting reperfusion injury have been described, such as induced hypothermia, controlled reperfusion, and ischemic preconditioning. Induced hypothermia is the induction of moderate hypothermia, thought to suppress many of the chemical reactions associated with reperfusion injury. Controlled reperfusion refers to controlling the initial period of reperfusion by reperfusing the tissue at a low pressure using blood that has been modified to be hyperosmolar, alkalotic, and substrate-enriched. Ischemic preconditioning is the purposeful causing of short ischemic events to have protective effect by slowing cell metabolism during a longer ischemic event. Although these treatments may be useful in surgical settings (e.g., before or after planned heart surgery), they are not possible in emergency settings.

The invention has particular application in preventing or limiting the severity of renal reperfusion injury, including lung injury secondary to renal reperfusion, preventing or limiting reperfusion heart injuries subsequent to a myocardial infarction, preventing or limiting reperfusion brain injuries subsequent to a cardiovascular injury, including without limitation myocardial infarction, stroke or the like. The invention has further particular application in preventing or limiting reperfusion organ damage in organ transplant, including transplant of the heart, kidney, liver, lungs, pancreas or small intestine. In one aspect, the pharmaceutical composition of the present invention may be utilized for perfusion of a transplant organ, which perfusion may be prior to, during or subsequent to transplant of the organ.

In one embodiment, the invention is directed to methods of using one or more of the peptides of the present invention to protect the heart, brain or other organs of a patient against injury caused by ischemia-reperfusion injury, including injury caused by or during reperfusion. The protective effect against ischemia-reperfusion injury occurs instantaneously or within a short time period following administration of a composition comprising one or more of the peptides of the present invention, preferably within at least about 40 minutes following administration, more preferably within 1-20 minutes, more preferably within 1-15 minutes, and most preferably within about 1-10 minutes.

2.6 Diseases Related to Increased Cytokine Expression and Related Diseases, Indications, Conditions and Syndromes.

Expression of various cytokines is increased during an inflammatory process, including an inflammatory process secondary to circulatory shock, ischemia, reperfusion injury and the like. TNF-α is a pleiotropic cytokine produced mainly by macrophages, and also by other types of cells. Other cytokines which increase during an inflammatory process, including an inflammatory process secondary to circulatory shock, ischemia, reperfusion injury and the like, include IL-1 and IL-6. While cytokines such as TNF-α have beneficial effects in many instances, significantly increased levels, such as secondary to circulatory shock, ischemia, reperfusion injury and the like, can have pathological effects. In one aspect, reperfusion of hypoxic or ischemic tissues, such hypoxic as secondary to circulatory shock, results in inflammatory responses, including increased cytokine expression.

In one embodiment, the invention is directed to methods of using one or more of the peptides of the present invention to decrease pro-inflammatory cytokine production and expression, including decreasing pro-inflammatory cytokine production and expression secondary to circulatory shock, ischemia, reperfusion injury and the like. The decrease in pro-inflammatory cytokine production and expression, including without limitation one or more of TNF-α, IL-1 and IL-6, occurs instantaneously or within a short time period following administration of a composition comprising one or more of the peptides of the present invention, preferably within at least about 40 minutes following administration, more preferably within 1-20 minutes, more preferably within 1-15 minutes, and most preferably within about 1-10 minutes.

In a related embodiment, the invention is directed to methods of using one or more of the peptides of the present invention to increase anti-inflammatory cytokine production and expression. The increase in anti-inflammatory cytokine production and expression, including without limitation IL-10, occurs instantaneously or within a short time period following administration of a composition comprising one or more of the peptides of the present invention, preferably within at least about 40 minutes following administration, more preferably within 1-20 minutes, more preferably within 1-15 minutes, and most preferably within about 1-10 minutes.

2.7 Use for Hemodialysis.

The compositions and methods of the present invention may be employed to prevent hypotension while subjects are undergoing hemodialysis, as an adjunct in the removal of excess extracellular fluid during hemodialysis by preventing or minimizing hypotension secondary to removal of excess fluid, to stabilize high blood pressures between hemodialysis treatments by removal of excess extracellular fluid, and for similar and related indications. In hemodialysis, blood is pumped through the blood compartment of a dialyzer, exposing it to a semipermeable membrane. The cleansed blood is then returned via the circuit back to the body. Ultrafiltration occurs by increasing the hydrostatic pressure across the dialyzer membrane, generally by applying a negative pressure to the dialysate compartment of the dialyzer. This pressure gradient causes water and dissolved solutes to move from blood to the dialysate, and allows removal of up to several liters of excess extracellular fluid during a typical 3 to 5 hour treatment.

Removal of excess extracellular fluid in subjects on long-term hemodialysis is critical because the presence of chronic volume expansion of excess fluid results in hypertension. However, it is frequently not possible to remove all accumulated excess fluid during hemodialysis because of intradialytic (during dialysis) hypotension. Intradialytic hypotension is defined as a decrease in systolic blood pressure by 20 mm Hg or a decrease in mean arterial pressure by 10 mm Hg more. Intradialytic hypotension is associated with symptoms such as abdominal discomfort, nausea, vomiting, muscle cramps, dizziness or fainting, and anxiety. Intradialytic hypotension can induce cardiac arrhythmias, and predispose the subject to coronary ischemic events or cerebral ischemic events.

Estimates are that intradialytic hypotension occurs in about 25% to 50% of all hemodialysis sessions. The primary cause of intradialytic hypotension is believed to be the rapid removal of circulatory volume during hemodialysis, resulting in hemodynamic instability. The most common current treatment for intradialytic hypotension is either to decrease the rate of fluid removal or infuse fluid, but both methods result in insufficient dialysis and resulting volume overload. Pharmacological interventions have been considered, such as use of midodrine, an α-adrenergic agent. However, this is associated with a number of side effects, including induction of supine systolic hypertension. In addition, various vasopressin receptor agonists have been considered for this indication, as disclosed in U.S. Pat. No. 7,183,255, issued Feb. 27, 2007.

2.8 Acute Blood Loss Secondary to Surgery and Related Indications, Conditions and Syndromes.

The pharmaceutical compositions and methods of the present invention can be utilized for subjects with acute blood loss that occurs during surgery. In one embodiment, the subject can be undergoing a surgery that can cause acute blood loss. In another embodiment, the subject can be scheduled to undergo a surgery that can cause acute blood loss. In another embodiment, the subject can be predisposed to or at high risk of needing a surgery that can cause acute blood loss as a result of genetic factors (e.g., family history) and/or environmental factors (e.g., diet).

As used herein, the term "surgery" is used interchangeable with the term "operation." A surgery that causes acute blood loss can involve any type of cell (e.g., somatic cell, germ cell, embryonic cell, stem cell), tissue (e.g., bone, muscle, connective, blood), and/or organ (e.g., brain, kidney, lung, heart, pancreas, prostate, ovary, uterus, gastrointestinal tract). Examples of surgeries that can cause acute blood loss include, but are not limited to, an elective surgery.

There are many different types of surgery including, but is not limited to, optional or elective surgery, required surgery, and urgent or emergency surgery. Many surgical procedures are associated with a high risk of hemorrhage or blood loss. These include cardiac surgeries, coronary artery bypass graft surgery, abdominal hysterectomies, cerebral amyloid angiopathy, repair of a brain aneurysm, radiosurgery for arteriovenous malformations, endovascular treatment of posteri or circulation aneurysms, proliferative vitreoretinopathy, lipoma excision, and sinus surgery. As such, the subject can be one who is undergoing, scheduled to undergo, or has undergone one of the foregoing surgical procedures, or any other surgical procedure with a high risk of hemorrhage or blood loss, or any other surgical procedure in which there is intra-operative or post-operation hemorrhage, blood loss, hypovolemia or hypotension.

In one aspect, the compositions and methods of the invention have particular application in cardiac surgery, such as coronary artery bypass graft surgery. Over 500,000 bypass surgeries are performed per year in the United States, but there are no approved cardioprotective drugs for reduction of cardiovascular events post surgery. Additionally, a large proportion of bypass patients are hypotensive prior to or during surgery, and are currently administered conventional vasopressor drugs.

The subject can be administered compositions including one or more of the peptides of the present invention by the methods of the present invention before, during and/or after the surgery. The timing and quantity of compositions administered to a patient which include one or more peptides of the present invention can be selected by the skilled practitioner using ordinary skill taking into account, for example, the degree of blood loss in the subject.

2.9 Acute Blood Loss Secondary to Trauma and Related Indications, Conditions and Syndromes.

The pharmaceutical compositions and methods of the present invention can be utilized for subjects with acute blood loss from trauma. In one embodiment, the subject is suffering from or diagnosed with a trauma that can cause acute blood loss. In another embodiment, the subject can be predisposed to or at risk of suffering a trauma that causes acute blood loss as a result of genetic factors (e.g., triple-X syndrome) and/or environmental factors (e.g., living in a high crime neighborhood).

As used herein, the term "trauma" is used interchangeable with the term "injury." A trauma that causes acute blood loss can involve any type of cell (e.g., somatic cell, germ cell, embryonic cell, stem cell), tissue (e.g., bone, muscle, connective, blood), and/or organ (e.g., brain, kidney, lung, heart, pancreas, prostate, ovary, uterus, gastrointestinal tract). Examples of trauma that can cause acute blood loss include, but are not limited to, a burn, a gunshot wound, and a stab wound.

There are many different types of trauma including, but not limited to, accidental injury and criminal injury. An accidental injury is injury sustain in any type of accident (e.g., automobile accident injury, whiplash, drowning, fall, sports injury, burn, machinery accident, suffocation, natural accident, accidental eye injury, occupational injury, toy-related injury). Criminal injury is injury caused by criminal activity (e.g., child abuse, assault), and in particular, gunshot wound and stab wound.

Trauma includes battlefield trauma. Battlefield trauma includes trauma secondary to gunshot or an explosive device, including but not limited to rockets, mortars, mines, improvised explosive devices and the like. Uncontrolled hemorrhage is the leading cause of preventable combat-related deaths. The vast majority of these deaths occur in the field before the injured can be transported to a treatment facility. It has been estimated that the most common cause single cause of preventable death on the battlefield results from bleeding from extremity wounds. Bleeding from torso wounds is another cause of preventable death. Battlefield trauma also includes penetrating head wounds and injuries.

The subject can be administered compositions including one or more of the peptides of the present invention by the methods of the present invention, which administration may be before the onset of symptoms of conditions such as hypovolemic shock, traumatic shock or hemorrhagic shock, or after the onset of symptoms. The timing and quantity of compositions administered can be selected by the skilled practitioner using ordinary skill taking into account, for example, the degree of blood loss in the subject.

2.10 Ocular Disease, Indications, Conditions and Syndromes.

Dry eye disease is an ocular disease affecting approximately 10-20% of the population. This disease progressively affects larger percentages of the population as it ages, with the majority of these patients being women. In addition, almost everyone experiences ocular irritation, or the symptoms and/or signs of dry eye as a condition, from time to time under certain circumstances, such as prolonged visual tasking (e.g., working on a computer), being in a dry environment, using medications that result in ocular drying and so on. In individuals suffering from dry eye, the protective layer of tears that normally protects the ocular surface is compromised, a result of insufficient or unhealthy production of one or more tear components. This can lead to exposure of the surface of the eye, ultimately promoting desiccation and damage of surface cells. Signs and symptoms of dry eye include but are not limited to keratitis, conjunctival and corneal staining, redness, blurry vision, decreased tear film break-up time, decreased tear production, tear volume, and tear flow, increased conjunctival redness, excess debris in the tear film, ocular dryness, ocular grittiness, ocular burning, foreign body sensation in the eye, excess tearing, photophobia, ocular stinging, refractive impairment, ocular sensitivity, and ocular irritation. Patients may experience one or more of these symptoms. The excess tearing response may seem counter-intuitive, but it is a natural reflex response to the irritation and foreign body sensation caused by the dry eye. Some patients may also experience ocular itching due to a combination of ocular allergy and dry eye symptoms.

There are many possible variables that can influence a patient's signs or symptoms of dry eye including levels of circulating hormones, various autoimmune diseases (e.g. Sjogren's syndrome and systemic lupus erythematosus), ocular surgeries including PRK or LASIK, many medications, environmental conditions, visual tasking such as computer use, ocular fatigue, contact lens wear, and mechanical influences such as corneal sensitivity, partial lid closure, surface irregularities (e.g. pterygium), and lid irregularities (e.g. ptosis, entropion/ectropion, pinguecula). Environments with low humidity, such as those that cause dehydration, can exacerbate or cause dry eye symptoms, such as sitting in a car with the defroster on or living in a dry climate zone. In addition, visual tasking can exacerbate symptoms. Tasks that can greatly influence symptoms include watching TV or using a computer for long periods of time where the blink rate is decreased.

Uveitis is an ocular disease involving inflammation of the middle layer or uvea of the eye, and may also be understood to include any inflammatory process involving the interior of the eye. Uveitis includes anterior, intermediate, posterior and panuveitic forms, with the majority of uveitis cases anterior in location, involving inflammation of the iris and anterior chamber. This condition can occur as a single episode and subside with proper treatment or may take on a recurrent or chronic nature. Symptoms include red eye, injected conjunctiva, pain and decreased vision. Signs include dilated ciliary vessels, presence of cells and flare in the anterior chamber, and keratic precipitates on the posterior surface of the cornea. Intermediate uveitis includes inflammation and the presence of inflammatory cells in the vitreous cavity, and posterior uveitis include the inflammation of the retina and choroid. Uveitis may be secondary to any of a number of diseases and disorders, including acute posterior multifocal placoid pigment epitheliopathy, ankylosing spondylitis, Behçet's disease, birdshot retinochoroidopathy, brucellosis, herpes simplex, herpes zoster, inflammatory bowel disease, juvenile rheumatoid arthritis, Kawasaki disease, leptospirosis, Lyme disease, multiple sclerosis, psoriatic arthritis, Reiter's syndrome, sarcoidosis, syphilis, systemic lupus erythematosus, toxocariasis, toxoplasmosis, tuberculosis, Vogt-Koyanagi-Harada syndrome, Whipple disease or polyarteritis nodosa.

2.11 Inflammatory Diseases, Indications, Conditions and Syndromes.

Peptides, compositions and methods of the present invention are further directed towards the treatment of inflammatory diseases and inflammatory conditions in a subject. There are a number of inflammatory diseases and inflammatory conditions which may be so treated. In one aspect, the inflammatory condition results from a disease including a form of arthritis, including but not limited to osteoarthritis, rheumatoid arthritis, septic arthritis, gout and pseudogout, juvenile idiopathic arthritis, Still's disease and ankylosing spondylitis, as well as arthritis secondary to other diseases, such as arthritis secondary to lupus erythematosus, Henoch-Schönlein purpura, psoriatic arthritis, reactive arthritis, haemochromatosis, hepatitis, Wegener's granulomatosis, vasculitis syndromes, Lyme disease, familial Mediterranean fever, hyperimmunoglobulinemia D with recurrent fever, TNF receptor-associated periodic syndrome and inflammatory bowel disease, including Crohn's disease and ulcerative colitis. In another aspect, the inflammatory condition results from a disease including a form of inflammatory bowel disease, such as Crohn's disease, ulcerative colitis, collagenous colitis, lymphocytic colitis, ischemic colitis, diversion colitis, Behçet's syndrome, infective colitis and indeterminate colitis. In another aspect, the inflammatory condition results from an autoimmune disease, including but not limited to systemic syndromes such as systemic lupus erythematosus, Sjögren's syndrome, scleroderma, rheumatoid arthritis and polymyositis, or a syndrome affecting only a local body system, such as the endocrine system (diabetes mellitus type 1, Hashimoto's thyroiditis, Addison's disease, etc.), dermatologic system (pemphigus vulgaris), hematologic system (autoimmune hemolytic anemia), or neural system (multiple sclerosis). Thus autoimmune diseases include, in addition to the general syndromes discussed above, such diseases and conditions as acute disseminated encephalomyelitis, Addison's disease, ankylosing spondylitis, antiphospholipid antibody syndrome, aplastic anemia, autoimmune hepatitis, autoimmune oophoritis, celiac disease, Crohn's disease, gestational pemphigoid, Goodpasture's syndrome, Graves' disease, Guillain-Barré syndrome, Hashimoto's disease, idiopathic thrombocytopenic purpura, Kawasaki disease, lupus erythematosus, mixed connective tissue disease, multiple sclerosis, myasthenia gravis, opsoclonus myoclonus syndrome, optic neuritis, Ord's thyroiditis, pemphigus, pernicious anaemia, primary biliary cirrhosis, Reiter's syndrome, Sjögren's syndrome, Takayasu's arteritis, temporal arteritis, autoimmune hemolytic anemia and Wegener's granulomatosis.

In another aspect, the inflammatory condition results from or is related to chronic obstructive pulmonary disease (COPD), also known as chronic obstructive airway diseases, including but not limited to diseases characterized by the pathological limitation of airflow in the airway that is not fully reversible, such as for example chronic bronchitis, emphysema, pneumoconiosis, pulmonary neoplasms and other lung disorders. Other inflammatory conditions include upper or lower airway diseases and disorders, such as allergic asthma, non-allergic asthma, allergic rhinitis, vasomotor rhinitis, allergic conjunctivitis, non-allergic conjunctivitis, and the like, as well as airway diseases related to external toxins or substances, such as various forms of pneumoconiosis (coalworker's pneumoconiosis, asbestosis, silicosis, bauxite fibrosis, berylliosis, or siderosis), byssinosis or hypersensitivity pneumonitis (farmer's lung or bird fancier's lung).

In yet another aspect, the inflammatory condition results from or is related to some form of transplant-related condition or syndrome, such as graft-versus-host disease, hyperacute rejection, acute rejection, or chronic rejection. Graft-versus-host disease is a common complication of allogeneic bone marrow transplantation, but can occur with other transplantations, and particularly those with T cells present in the graft, either as contaminants or intentionally introduced. Hyperacute, acute or chronic rejection can occur with bodily organs such as kidneys, liver, pancreas, spleen, uterus, heart or lungs, as well as transplantation of bone, cornea, face, hand, penis or skin. In one embodiment, a pharmaceutical composition including one or more of the peptides of the present invention is given prophylactically to limit or prevent a transplant-related condition or syndrome, such as immediately before, during or after transplantation of a bodily fluid, organ or part. In another embodiment, the bodily fluid, organ or part being transplanted is perfused with a solution of a pharmaceutical composition including one or more of the peptides of the present invention. In yet another embodiment, one or more of the peptides of the present invention are administered in conjunction with, combination with or series with one or more other agents for transplant rejection, such as calcineurin inhibitors including cyclosporin or tacrolimus, mTOR inhibitors including sirolimus or everolimus, anti-proliferatives including azathioprine or mycophenolic acid, corticosteroids including prednisolone or hydrocortisone, antibodies such as monoclonal anti-IL-2Rα receptor antibodies, basiliximab or daclizumab, or polyclonal anti-T-cell antibodies such as anti-thymocyte globulin or anti-lymphocyte globulin.

2.12 Addiction Related Diseases, Indications, Conditions and Syndromes.

In one aspect, one or more of the present peptides may be employed for inhibiting alcohol consumption, or for reducing alcohol consumption, or for treating or preventing alcoholism, or for treating or preventing alcohol abuse, or for treating or preventing alcohol-related disorders. In another related aspect, one or more of the present peptides may be employed for inhibiting consumption of drugs of abuse, or for reducing consumption of drugs of abuse, or for treating or preventing drug abuse, or for treating or preventing drug abuse-related disorders. Drugs of abuse are typically controlled substances. These include controlled naturally derived drugs such as heroin, morphine, opium, cocaine, marijuana and the like, as well as synthetically made drugs such as Vicodin®, Lortab®, Lorcet®, Percocet®, Percodan®, Tylox®, hydrocodone, OxyContin®, methadone, tramadol, various methamphetamines, and other tranquilizers, stimulants, or sedatives known to be abused, as well as drugs for which there is no established pharmaceutical utility, such as ecstasy, LSD, or PCP.

3.0 Combination Therapy for Certain Indications

The peptides, compositions and methods of the present invention may be used for treatment of any of the foregoing diseases, indications, conditions or syndromes, or any disease, indication, condition or syndrome which is melanocortin receptor mediated, by administration in combination with one or more other pharmaceutically active compounds. Such combination administration may be by means of a single dosage form which includes both a peptide of the present invention and one more other pharmaceutically active compounds, such single dosage form including a tablet, capsule, spray, inhalation powder, injectable liquid or the like. Alternatively, combination administration may be by means of administration of two different dosage forms, with one dosage form containing a peptide of the present invention, and the other dosage form including another pharmaceutically active compound. In this instance, the dosage forms may be the same or different. Without meaning to limit combination therapies, the following exemplifies certain combination therapies which may be employed.

3.1 Combination Therapy for Obesity and Related Metabolic Syndrome.

One or more peptides of the invention may be combined with one or more other pharmacologically active agent(s) that is (are) useful in the treatment of various weight and feeding-related disorders, such as obesity and/or overweight, in particular other anti-obesity drugs that affect energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, or gastrointestinal motility. Drugs that reduce energy intake include, in part, various pharmacological agents, referred to as anorectic drugs, which are used as adjuncts to behavioral therapy in weight reduction programs.

Generally, a total dosage of the below-described obesity control agents or medications, when used in combination with one or more peptides of the present invention can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

One or more peptides of the invention may be combined with one or more other pharmacologically active agent(s) that is (are) useful in the treatment of diabetes, such as other anti-diabetic drugs.

One or more peptides of the invention may in addition or alternatively further be combined with one or more other pharmacologically active agent(s) that is (are) useful in the treatment of diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

According to a further aspect of the invention there is provided a combination treatment comprising the administration of a pharmacologically effective amount of a peptide according to the invention, or a pharmaceutically acceptable salt thereof, optionally together with a pharmaceutically acceptable diluent or carrier, with the simultaneous, sequential or separate administration one or more of the following agents selected from:

insulin and insulin analogues;

insulin secretagogues, including sulphonylureas (e.g. glipizide) and prandial glucose regulators (sometimes called "short-acting secretagogues"), such as meglitinides (e.g. repaglinide and nateglinide);

agents that improve incretin action, for example dipeptidyl peptidase IV (DPP-4) inhibitors (e.g. vildagliptin, saxagliptin, and sitagliptin), and glucagon-like peptide-1 (GLP-1) agonists (e.g. exenatide);

insulin sensitising agents including peroxisome proliferator activated receptor gamma (PPARγ) agonists, such as thiazolidinediones (e.g. pioglitazone and rosiglitazone), and agents with any combination of PPAR alpha, gamma and delta activity;

agents that modulate hepatic glucose balance, for example biguanides (e.g. metformin), fructose 1,6-bisphosphatase inhibitors, glycogen phopsphorylase inhibitors, glycogen synthase kinase inhibitors, and glucokinase activators;

agents designed to reduce/slow the absorption of glucose from the intestine, such as alpha-glucosidase inhibitors (e.g. miglitol and acarbose);

agents which antagonise the actions of or reduce secretion of glucagon, such as amylin analogues (e.g. pramlintide);

agents that prevent the reabsorption of glucose by the kidney, such as sodium-dependent glucose transporter 2 (SGLT-2) inhibitors (e.g. dapagliflozin);

agents designed to treat the complications of prolonged hyperglycaemia, such as aldose reductase inhibitors (e.g. epalrestat and ranirestat); and agents used to treat complications related to micro-angiopathies;

anti-dyslipidemia agents, such as HMG-CoA reductase inhibitors (statins, e.g. rosuvastatin) and other cholesterol-lowering agents; PPARα agonists (fibrates, e.g. gemfibrozil and fenofibrate); bile acid sequestrants (e.g. cholestyramine); cholesterol absorption inhibitors (e.g. plant sterols (i.e. phytosterols), synthetic inhibitors); cholesteryl ester transfer protein (CETP) inhibitors; inhibitors of the ileal bile acid transport system (IBAT inhibitors); bile acid binding resins; nicotinic acid (niacin) and analogues thereof; anti-oxidants, such as probucol; and omega-3 fatty acids;

antihypertensive agents, including adrenergic receptor antagonists, such as beta blockers (e.g. atenolol), alpha blockers (e.g. doxazosin), and mixed alpha/beta blockers (e.g. labetalol); adrenergic receptor agonists, including alpha-2 agonists (e.g. clonidine); angiotensin converting enzyme (ACE) inhibitors (e.g. lisinopril), calcium channel blockers, such as dihydropridines (e.g. nifedipine), phenylalkylamines (e.g. verapamil), and benzothiazepines (e.g. diltiazem);

angiotensin II receptor antagonists (e.g. candesartan); aldosterone receptor antagonists (e.g. eplerenone); centrally acting adrenergic drugs, such as central alpha agonists (e.g. clonidine); and diuretic agents (e.g. furosemide);

haemostasis modulators, including antithrombotics, such as activators of fibrinolysis; thrombin antagonists; factor VIIa inhibitors; anticoagulants, such as vitamin K antagonists (e.g. warfarin), heparin and low molecular weight analogues thereof, factor Xa inhibitors, and direct thrombin inhibitors (e.g. argatroban); antiplatelet agents, such as cyclooxygenase inhibitors (e.g. aspirin), adenosine diphosphate (ADP) receptor inhibitors (e.g. clopidogrel), phosphodiesterase inhibitors (e.g. cilostazol), glycoprotein IIB/IIA inhibitors (e.g. tirofiban), and adenosine reuptake inhibitors (e.g. dipyridamole);

anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyltransferase (DGAT) inhibitors, and cannabinoid (CB1) receptor antagonists (e.g. rimonabant);

feeding behavior modifying agents, such as orexin receptor modulators and melanin-concentrating hormone (MCH) modulators;

glucagon like peptide-1 (GLP-1) receptor modulators;

neuropeptideY (NPY)/NPY receptor modulators;

pyruvate dehydrogenase kinase (PDK) modulators;

serotonin receptor modulators;

leptin/leptin receptor modulators;

ghrelin/ghrelin receptor modulators; or monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), triple monoamine reuptake blockers (e.g. tesofensine), and monoamine oxidase inhibitors (MAOI) (e.g. toloxatone and amiflamine), or a pharmaceutically acceptable salt, solvate, solvate of such a salt or a prodrug thereof, optionally together with a pharmaceutically acceptable carrier to a mammal, such as man, in need of such therapeutic treatment.

According to an additional further aspect of the present invention there is provided a combination treatment comprising the administration of a pharmacologically effective amount of a compound according to the invention, or a pharmaceutically acceptable salt thereof, optionally together with a pharmaceutically acceptable carrier, with the simultaneous, sequential or separate administration of very low calorie diets (VLCD) or low-calorie diets (LCD).

3.2 Combination Therapy for Sexual Dysfunction.

It is also possible and contemplated to use cyclic peptides of the present invention in combination with other drugs or agents, such as for treatment of sexual dysfunction. These other drugs and agents may include agents that induce erectile activity, including phosphodiesterase-5 (PDE-5) inhibitors, testosterone, prostaglandin and the like. In a preferred embodiment of the invention, cyclic peptides of the invention are used in combination with a therapeutically effective amount of a cyclic-GMP-specific phosphodiesterase inhibitor or an alpha-adrenergic receptor antagonist. The teachings and disclosure of U.S. Pat. No. 7,235,625 entitled "Multiple Agent Therapy for Sexual Dysfunction" are incorporated here by reference as if set forth in full.

The present invention thus provides methods of treating sexual dysfunction, the methods comprising the step of administering to the patient having or at risk of having sexual dysfunction a therapeutically effective amount of a cyclic peptide of the present invention in combination with a therapeutically effective amount of a second sexual dysfunction pharmaceutical agent. The cyclic peptide of the present invention may be administered simultaneously with, prior to or subsequent to administration with a therapeutically effective amount of a second sexual dysfunction pharmaceutical agent. Preferably the peptide of the present invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the peptide of the present invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the peptide of the present invention when desired or needed by the patient.

The present invention thus provides methods of treating sexual dysfunction, the methods comprising the step of administering to a patient having or at risk of having sexual dysfunction a therapeutically effective amount of a cyclic peptide of the present invention in combination with another compound that is useful in the treatment of sexual dysfunction. In a preferred embodiment of combination therapy the sexual dysfunction is female sexual dysfunction. In an especially preferred embodiment of combination therapy the sexual dysfunction is erectile dysfunction.

The present invention also provides pharmaceutical compositions that comprise a cyclic peptide of the present invention and a second compound useful for the treatment of sexual dysfunction. In an embodiment of the composition, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphine; oxytocin modulators; α-adrenergic antagonists; androgens; selective androgen receptor modulators (SARMs); buproprion; vasoactive intestinal peptide (VIP); neutral endopeptidase inhibitors (NEP); and neuropeptide Y receptor antagonists (NPY).

In an embodiment of the method and composition, the second sexual dysfunction pharmaceutical agent is testosterone.

In another embodiment of combination therapy, the second sexual dysfunction pharmaceutical agent is a type V phosphodiesterase (PDE-5) inhibitor. For example, the PDE-5 inhibitor may be Viagra®, a brand of sildenafil, Levitra®, a brand of monohydrochloride salt of vardenafil, or Cialis®, a brand of tadalafil. Other PDE-5 inhibitors are disclosed in U.S. Pat. No. 7,235,625, issued Jun. 22, 2007, and entitled "Multiple Agent Therapy for Sexual Dysfunction", incorporated here by reference.

In another embodiment of the composition above, the compound useful for the treatment of sexual dysfunction is an estrogen agonist/antagonist. In one embodiment, the estrogen agonist/antagonist is (−)-cis-6-phenyl-5-[4-(2-pyrrolidin-1-yl-ethoxy)-phenyl]-5,6,7,8-tetrahydro-napthalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a cyclic peptide of the present invention may be used in combination with any known mechanical aids or devices.

The present invention also provides kits for the treatment of sexual dysfunction (including erectile dysfunction), the kits comprising: a first pharmaceutical composition including a cyclic peptide of the present invention; a second pharmaceutical composition comprising a second compound useful for the treatment of sexual dysfunction; and, a container for the first and second compositions.

4.0 Methods of Administration and Use

The method of administration and use varies depending upon the characteristic of specific peptides of the present invention, the disease, indication, condition or syndrome to be treated, and other factors known to those in the art. In general, any method of administration and use known in the art or hereafter developed may be employed with the peptides of the present invention. Without limiting the foregoing, the following methods of administration and use have specific application for the indicated indications.

4.1 Methods of Administration and Use for Obesity and Related Metabolic Syndrome.

Compositions including one or more peptides of the present invention may administered by any suitable means for therapy, including prophylactic therapy, of obesity and metabolic syndrome. In one aspect, the composition is formulated for subcutaneous injection, and a subcutaneous injection is given one or more times each day, preferably prior to a meal, more preferably between about one and about three hours prior to a meal. In another aspect, the composition is formulated as an injectable sustained release formulation. In one embodiment, a peptide of the present invention is formulated with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a peptide of the present invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany). Such formulations may be made, for example, by combining a peptide of the present invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a sustained release injectable formulation. The teachings of U.S. Pat. Nos. 4,938,763, 6,432,438, and 6,673,767, and the biodegradable polymers and methods of formulation disclosed therein, are incorporated here by reference. The formulation may be such that an injection is required on a weekly, monthly or other periodic basis, depending on the concentration and amount of peptide, the biodegradation rate of the polymer, and other factors known to those of skill in the art.

Compositions including one or more peptides of the present invention may be administered orally in an individual dosage form such as a tablet or capsule. In one preferred aspect, the individual dosage form includes an enteric coating, and optionally one or more agents to increase uptake, decrease protease degradation, increase cellular permeability, and the like.

4.2 Methods of Administration and Use for Sexual Dysfunction.

For sexual dysfunction, in a preferred aspect one or more peptides of the present invention is formulated such that it may be administered on demand, such as about less than one hour, less than two hours or less than about four hours prior to anticipated sexual activity. In one embodiment the composition is formulated for subcutaneous injection. In another embodiment, the composition is formulated for any of a variety of transdermal routes of administration, including buccal administration, nasal administration, inhalation administration and the like. If the composition is formulated for nasal administration, administration may comprise a metered spray device delivering a volume of from about 20 to about 200 µL of an aqueous composition including any of a variety of other agents, including permeability enhancing agents.

4.3 Methods of Administration and Use for Circulatory Shock and Related Diseases, Indications, Conditions and Syndromes.

In yet another aspect, the invention includes methods which optionally include monitoring the subject for symptoms of circulatory shock both before and after administration of a pharmaceutical composition including one or more of the peptides of the present invention. Thus a subject may be administered one or more of the peptides of the present invention by one of the methods of the invention after suffering an injury likely to induce circulatory shock but prior to the manifestation of overt symptoms of cardiovascular shock, including prior to manifestation of circulatory shock in Stage I, Stage II or Stage III.

Methods of treating or preventing shock described herein comprise administering a therapeutically effective amount of one or more of the peptides of the present invention to a subject. As used herein, the term "administer" and "administering" are used to mean introducing one or more of the peptides of the present invention into a patient. When administration is for the purpose of treatment, one or more of the peptides of the present invention are provided at, or after the onset of, a symptom of shock. The therapeutic administration of one or more of the peptides of the present invention serves to attenuate any symptom, or prevent additional symptoms from arising. When administration is for the purposes of preventing shock ("prophylactic administration"), one or more of the peptides of the present invention are provided in advance of any visible or detectable symptom. The prophylactic administration of one or more of the peptides of the present invention serve to attenuate subsequently arising symptoms or prevent symptoms from arising altogether. The route of administration of one or more of the peptides of the present invention include, but are not limited to, topical, transdermal, intranasal, vaginal, rectal, oral, subcutaneous, intravenous, intraarterial, intramuscular, intraosseous, intraperitoneal, epidural and intrathecal.

Furthermore, the methods of treating or preventing circulatory shock of the present invention also relate to coadministering one or more substances to the subject in addition to one or more of the peptides of the present invention. The term "coadminister" indicates that each of at least two compounds is administered during a time frame wherein the respective periods of biological activity or effects overlap. Thus the term includes sequential as well as concurrent administration of compounds where one compound is one or more of the peptides of the present invention. If more than one compound is coadministered, the routes of administration of the two or more compounds need not be the same. The scope of the invention is not limited by the identity of the compound which may be coadministered. For example, one or more of the peptides of the present invention may be coadministered with androstenetriol, androstenediol or derivatives thereof, various vasopressin agonists, or other pharmaceutically active substances, such as catecholamines or other a adrenergic agonists, $\alpha_2$ adrenergic agonists, $\beta$ adrenergic agonists or $\beta_2$ adrenergic agonists, including but not limited to epinephrine, norepinephrine, dopamine, isoproterenol, vasopressin and dobutamine. Alternatively, one or more of the peptides of the present invention may be coadministered with fluids or other substances that are capable of alleviating, attenuating, preventing or removing symptoms in a subject suffering from, exhibiting the symptoms of, or at risk of suffering from hypovolemic shock, vasodilatory shock or cardiogenic shock. Types of fluid that can be coadministered with one or more of the peptides of the present invention should be specific to the circumstances surrounding the particular subject that is suffering from, exhibiting the symptoms of, or at risk of suffering from shock. For example, fluids that may be coadministered with one or more of the peptides of the present invention include, but are not limited to, salt solutions—such as sodium chloride and sodium bicarbonate—as well as whole blood, synthetic blood substitutes, plasma, serum, serum albumin and colloid solutions. Colloid solutions include, but are not limited to, solutions containing hetastarch, albumin or plasma. In one particular embodiment of the present invention, fluids such as one or more of salt solutions, colloidal solutions, whole blood, synthetic blood substitutes, plasma or serum are coadministered with one or more of the peptides of the present invention in patients suffering from or exhibiting the symptoms of a hypovolemic shock, such as hemorrhagic shock.

Particular embodiments of the coadministration methods of the present invention include methods of performing a transfusion in a subject, with the transfusion methods comprising providing blood or synthetic blood substitutes that comprise one or more of the peptides of the present invention to a subject. The blood used in the transfusion methods can be whole blood, synthetic blood substitutes, or any fractionated portion of whole blood, such as plasma, serum, or red blood cells.

4.4 Methods of Administration and Use for Prophylactic Therapy for Circulatory Shock and Related Diseases, Indications, Conditions and Syndromes.

The invention also relates to methods of preventing or preventing the progression of shock in a subject at risk of suffering from shock by administering a therapeutically effective amount of one or more of the peptides of the present invention to the subject, prior to or immediately at the onset of the first symptoms of shock. As used herein, the term "prevent," as it relates to shock, indicates that a substance of the present invention is administered to a subject to prohibit one or more symptoms of shock from detectably appearing or to attenuate the effects of one or more symptoms of shock. The term "prevent" also encompasses prohibiting entirely shock or any of its associated symptoms, from detectably appearing. Thus a subject may be "pretreated," such as a subject in a surgical setting, by using the substances of the present invention to prevent shock from arising. The phrase "preventing the progression," as it relates to shock, is used to mean a procedure designed to prohibit the detectable appearance of one or more additional symptoms of shock in a patient already exhibiting one or more symptoms of shock, and is also used to mean prohibiting the already-present symptoms of shock from worsening in the subject. The symptoms of shock that are included in preventative methods of the present invention include, but are not limited to, such symptoms of shock as highlighted herein, such as tachycardia, shallow or erratic breathing and death. A subject that is "at risk of shock" may be recognized based upon the specific circumstances surrounding a subject. For example, a surgery patient or a subject that has been wounded and begun losing blood would be at risk of shock. Similarly, a patient with a bacterial infection and exhibiting a fever or low blood pressure may also be at risk of shock or an inflammatory disease or condition.

In additional embodiments of the present invention, the methods are used to prevent cardiogenic shock, hypovolemic shock and vasodilatory shock, each of which can be in any of the three aforementioned stages of shock. In one particular embodiment of the present invention, the methods are used to prevent cardiogenic shock. In another particular embodiment of the present invention, the methods are used to prevent vasodilatory shock. In another more particular embodiment of the present invention, the methods are used to prevent shock resulting from sepsis or bacteremia. In an even more particular embodiment, the methods are used to prevent septic shock or bacteremic shock in Stage I, II or III shock. In yet another embodiment, the methods of the present invention are used to prevent hypovolemic shock. In one particular embodiment of the present invention, the methods are used prevent hemorrhagic shock. In an even more particular embodiment, the methods are used to prevent hemorrhagic shock in Stage I, Stage II or Stage III.

Similar to the methods of treating shock described herein, one embodiment of the methods of preventing shock of the present invention comprises coadministering another substance with one or more of the peptides of the present invention or a derivative thereof. The scope of the invention is not limited by the identity of the substance which may be coadministered with one or more of the peptides of the present invention to prevent shock. For example, one or more of the peptides of the present invention may be coadministered with androstenetriol, androstenediol or derivatives thereof, various vasopressin agonists, or other pharmaceutically active substances, such as catecholamines or other a adrenergic agonists, $\alpha_2$ adrenergic agonists, $\beta$ adrenergic agonists or $\beta_2$ adrenergic agonists, including but not limited to epinephrine, norepinephrine, dopamine, isoproterenol, vasopressin and dobutamine, to prevent shock.

Alternatively, one or more of the peptides of the present invention may be coadministered with fluids or other substances that are capable of preventing or removing symptoms in a subject at risk of suffering from hypovolemic shock, vasodilatory shock or cardiogenic shock. The types of fluid that can be coadministered with one or more of the peptides of the present invention to prevent shock should be specific to the circumstances surrounding the particular subject that is at risk of suffering from shock. For example, fluids that may be coadministered with one or more of the peptides of the present invention include, but are not limited to, salt solutions—such as sodium chloride and sodium bicarbonate—as well as whole blood, synthetic blood substitutes, plasma, serum, serum albumin and colloid solutions. Colloid solutions include, but are not limited to, solutions containing hetastarch, albumin or plasma. In one particular embodiment of the present invention, fluids including one or more of salt solutions, colloidal solutions, whole blood, synthetic blood substitutes, plasma or serum are coadministered with one or more of the peptides of the present invention or a derivative thereof in subjects at risk of suffering a hypovolemic shock, such as hemorrhagic shock.

4.5 Methods of Administration and Use for Inflammation Related Applications, Diseases, Indications, Conditions and Syndromes.

In yet another aspect, the invention includes methods which optionally include monitoring the subject for signs or symptoms of inflammation, inflammatory diseases or inflammatory conditions both before and after administration of one or more of the peptides of the present invention. Thus a subject may be administered one or more of the peptides of the present invention by one of the methods of the invention after being diagnosed with a condition, disease or syndrome likely to induce an inflammatory response, but prior to the manifestation of overt symptoms of inflammation, inflammatory disease or inflammatory condition. Methods of treating or preventing inflammation, inflammatory diseases or inflammatory conditions described herein comprise administering a therapeutically effective amount of one or more of the peptides of the present invention to a subject. When administration is for the purpose of treatment, the substance is provided at, or after the onset of, a sign or symptom of inflammation, inflammatory disease or inflammatory condition. The therapeutic administration of this substance serves to attenuate any symptom, or prevent additional symptoms from arising. When administration is prophylactic administration for the purposes of preventing or limiting inflammation, inflammatory disease or an inflammatory condition, a pharmaceutical composition including one or more of the peptides of the present invention is provided in advance of any visible or detectable symptom. The prophylactic administration of one or more of the peptides of the present invention serve to attenuate subsequently arising symptoms or prevent symptoms from arising altogether. The route of administration of one or more of the peptides of the present invention include, but are not limited to, topical, transdermal, intranasal, vaginal, rectal, oral, subcutaneous intravenous, intraarterial, intramuscular, intraosseous, intraperitoneal, epidural and intrathecal.

4.6 Methods of Administration and Use for Ocular Diseases, Indications, Conditions and Syndromes.

For ocular applications, in one aspect one or more of the peptides of the present invention are formulated in an ophthalmic dosage form and is administered in the form of eye drops, eye washes or by means of other ocular delivery systems.

4.7 Devices for Administration for Hemorrhagic or Traumatic Shock.

In certain aspects, special devices may be provided for delivery and administration of a pharmaceutical composition including one or more of the peptides of the present invention. Thus in one aspect a prefilled syringe may be adapted for use in military applications for emergency treatment under battlefield conditions, such as for treatment of battlefield trauma, or use by paramedic personnel responding to a trauma victim. The prefilled syringe may include a lyophilized component including one or more of the peptides of the present invention and an aqueous solubilizing component, such that the pharmaceutical composition may be reconstituted immediately prior to use. The resulting reconstituted pharmaceutical composition may be an isotonic or hypertonic solution. In a related aspect, the prefilled syringe may include one or more of the peptides of the present invention in solution with the pharmaceutical composition including one or more preservatives or stabilizers, such that the prefilled syringe may be stored for a specified period at ambient temperature, such as room temperature, without substantial degradation.

5.0 Methods of Making

In general, the peptides of the present invention may be synthesized by solid-phase synthesis and purified according to methods known in the art. Any of a number of well-known procedures utilizing a variety of resins and reagents may be used to prepare the peptides of the present invention.

The cyclic peptides of the present invention may be readily synthesized by known conventional procedures for the formation of a peptide linkage between amino acids. Such conventional procedures include, for example, any solution phase procedure permitting a condensation between the free alpha amino group of an amino acid or residue thereof having its carboxyl group and other reactive groups protected and the free primary carboxyl group of another amino acid or residue thereof having its amino group or other reactive groups protected. In a preferred conventional procedure, the cyclic peptides of the present invention may be synthesized by solid-phase synthesis and purified according to methods known in the art. Any of a number of well-known procedures utilizing a variety of resins and reagents may be used to prepare the peptides of the present invention.

The process for synthesizing the cyclic peptides may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide. The resulting peptide is then cyclized to yield a cyclic peptide of the invention.

Solid phase peptide synthesis methods are well known and practiced in the art. In such methods the synthesis of peptides of the invention can be carried out by sequentially incorporating the desired amino acid residues one at a time into the growing peptide chain according to the general principles of solid phase methods. These methods are disclosed in numerous references, including Merrifield, R. B., Solid phase synthesis (Nobel lecture). *Angew Chem* 24:799-810 (1985) and Barany et al. *The Peptides, Analysis, Synthesis and Biology*, Vol. 2, Gross, E. and Meienhofer, J., Eds. Academic Press 1-284 (1980).

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz) and aliphatic urethane-type protecting groups, such as t-butyloxycarbonyl (Boc), diisopropylmethoxycarbonyl, isopropoxycarbonyl, and allyloxycarbonyl (Alloc). Fmoc are preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf) and Boc. Pbf and Pmc are preferred protecting groups for Arg.

The peptides of the invention described herein were prepared using solid phase synthesis, such as by means of a Symphony Multiplex Peptide Synthesizer (Rainin Instrument Company) automated peptide synthesizer, using programming modules as provided by the manufacturer and following the protocols set forth in the manufacturer's manual.

Solid phase synthesis is commenced from the C-terminal end of the peptide by coupling a protected alpha amino acid to a suitable resin. Such starting material is prepared by attaching an alpha amino-protected amino acid by an ester linkage to a p-benzyloxybenzyl alcohol (Wang) resin, a 2-chlorotrityl chloride resin or an oxime resin, by an amide bond between an Fmoc-Linker, such as p-[(R,S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Typically, orthogonal protecting groups are used as appropriate. For example, the peptides of the invention contain multiple amino acids with an amino group-containing side chain. In one aspect, an Allyl-Alloc protection scheme is employed with the amino acids forming a lactam bridge through their side chains, and orthogonal protecting groups, cleavable under different reactive conditions, use for other amino acids with amino group-containing side chains. Thus, for example, Fmoc-Lys(Alloc)-OH, Fmoc-Orn(Alloc)-OH, Fmoc-Dap(Alloc)-OH, Fmoc-Dab(Alloc)-OH, Fmoc-Asp (OAll)-OH or Fmoc-Glu(OAll)-OH amino acids can be employed for the positions forming a lactam bridge upon cyclization, while other amino acids with amino group-containing side chains have a different and orthogonal protecting group, such as with Fmoc-Arg(Pbf)-OH, Fmoc-Lys(Pbf)-OH, Fmoc-Dab(Pbf)-OH or the like. Other protecting groups may be similarly employed; by way of example and not limitation, Mtt/OPp (4-methyltrityl/2-phenylisopropyl) can be employed with the side chains forming a lactam bridge upon cyclization, with orthogonal protecting groups being utilized for other positions that are not cleavable using conditions suitable for cleavage of Mtt/OPp.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Similarly, methods for modifying side chains of amino acids are well known to those skilled in the art of peptide synthesis. The choice of modifications made to reactive groups present on the peptide will be determined, in part, by the characteristics that are desired in the peptide.

In the peptides of the present invention, in one embodiment the N-terminus group is modified by introduction of an N-acetyl group. In one aspect, a method is employed wherein after removal of the protecting group at the N-terminal, the resin-bound peptide is reacted with acetic anhydride in DMF in the presence of an organic base, such as pyridine or diisopropylethylamine. Other methods of N-terminus acetylation are known in the art, including solution phase acetylation, and may be employed.

The peptide can, in one embodiment, be cyclized prior to cleavage from the peptide resin. For cyclization through reactive side chain moieties, the desired side chains are deprotected, and the peptide suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino)phosphonium-hexafluorophosphate (BOP), benzotriazole-1-yl-oxy-tris(pyrrolidino)phosphoniumhexafluorophosphate (PyBOP), 2-(7-aza-1H-benzotriazol-1-yl)-1,1,3,3-tetramethyluronium tetrafluoroborate (TATU), 2-(2-oxo-1(2H)-pyridyl)-1,1,3,3-tetramethyluronium tetrafluoroborate (TPTU) or N,N'-dicyclohexylcarbodiimide/1-hydroxybenzotriazole (DCCI/HOBt). Coupling is conventionally initiated by use of a suitable base, such as N,N-diisopropylethylamine (DIPEA), sym-collidine or N-methylmorpholine (NMM).

For peptides with a non-lactam cyclic bridge, such as peptides containing the bridge:

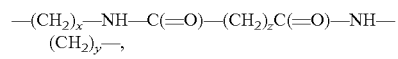

where x, y and z are each independently 1 to 5, the peptides may be made using solid phase synthesis employing a side-chain protected diamine amino acid for the positions to be cyclized. Particularly preferred in such positions are Dap, Dab or Lys, preferably with an amine protecting group such as Alloc, Mtt, Mmt (methoxytrityl), Dde (1-(4,4-dimethyl-2,6-dioxocyclohex-1-ylidene))ethyl), ivDde (1-(4,4-dimethyl-2,6-dioxocyclohex-1-ylidene)-3-methylbutyl) or any other orthogonally cleavable protecting group. Typically, one side chain protecting group is removed first, such as removal of Mtt using 2% TFA in dichloromethane. Following washing of the resin, the resulting resin-bound unprotected amine is acylated, such as with a 0.5 M solution of a cyclic anhydride such as succinic anhydride or glutaric anhydride in dichloromethane/pyridine 1:1. Following additional wash steps, the orthogonally cleavable protecting group of the second diamino amino acid is cleaved, such as removal of Alloc using tetrakis(triphenylphosphine)palladium(0) and phenyl silane in dichloromethane. After washing with dichloromethane and DMF the resin-bound peptide is cyclized using standard coupling reagents such as TBTU and a base. Alternatively, an ivDde protected resin-bound diamino amino acid can be deprotected using a solution of 5% of hydrazine in DMF, and after washing with DMF the resulting resin bound amine can either be acylated with a cyclic anhydride or can be cyclized with a resin bound carboxylic acid.

The cyclized peptides can then be cleaved from solid phase, using any suitable reagent, such as ethylamine in DCM or various combinations of agents, such as trifluoroacetic acid (TFA), tri-isopropylsilane (TIS), dimethoxybenezene (DMB), water and the like. The resulting crude peptide is dried and remaining amino acid side chain protecting groups, if any, are cleaved using any suitable reagent, such as (TFA) in the presence of water, TIS, 2-mercaptoethane (ME), and/or 1,2-ethanedithiol (EDT). The final product is precipitated by adding cold ether and collected by filtration. Final purification is by reverse phase high performance liquid chromatography (RP-HPLC), using a suitable column, such as a $C_{18}$ column, or other methods of separation or purification, such as methods based on the size or charge of the peptide, can also be employed. Once purified, the peptide can be characterized by any number of methods, such as high performance liquid chromatography (HPLC), amino acid analysis, mass spectrometry, and the like.

For peptides of the present invention which have a C-terminus substituted amide derivative or N-alkyl group, synthesis may proceed by solid phase synthesis commenced from the C-terminal end of the peptide by coupling a protected alpha amino acid to a suitable resin. Such methods for preparing substituted amide derivatives on solid-phase have been described in the art. See, for example, Barn D. R. et al., Synthesis of an array of amides by aluminum chloride assisted cleavage on resin bound esters. *Tetrahedron Letters*, 37:3213-3216 (1996); DeGrado W. F. and Kaiser E. T., Solid-phase synthesis of protected peptides on a polymer bound oxime: Preparation of segments comprising the sequences of a cytotoxic 26-peptide analogue. *J. Org. Chem.*, 47:3258-3261 (1982). Such a starting material can be prepared by attaching an alpha amino-protected amino acid by an ester linkage to a p-benzyloxybenzyl alcohol (Wang) resin or an oxime resin by well known means. The peptide chain is grown with the desired sequence of amino acids, the peptide cyclized and the peptide-resin treated with a solution of appropriate amine (such as methyl amine, dimethyl amine, ethylamine, and so on). Peptides employing a p-benzyloxybenzyl alcohol (Wang) resin may be cleaved from resin by aluminum chloride in DCM, and peptides employing an oxime resin may be cleaved by DCM.

While synthesis has been described primarily with reference to solid phase Fmoc chemistry, it is to be understood that other chemistries and synthetic methods may be employed to make the cyclic peptides of the invention, such as by way of example and not limitation, methods employing Boc chemistry, solution chemistry, and other chemistries and synthetic methods.

6.0 Formulations

Depending on the desired route of administration, the formulation of a composition including one or more cyclic peptides of the present invention may be varied. Thus the formulation may be suitable for subcutaneous injection, or intravenous injection, for topical applications, for ocular applications, for nasal spray applications, for inhalation applications, for other transdermal applications and the like.

6.1 Salt Form of Cyclic Peptides of the Present Invention.

The cyclic peptides of the present invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the cyclic peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of peptides of the present invention are prepared in a suitable solvent for the peptide and an excess of an acid, such as hydrochloric, hydrobromic, sulfuric, phosphoric, acetic, trifluoroacetic, citric, tartaric, maleic, succinic or methanesulfonic acid. The acetate, ammonium acetate and trifluoroacetic acid salt forms are especially useful. Where peptides of the present invention include an acidic moiety, suitable pharmaceutically acceptable salts may include alkali metal salts, such as sodium or potassium salts, or alkaline earth metal salts, such as calcium or magnesium salts. It is also to be understood that certain peptides of formula (I) can exist in solvated forms, including solvates of the free peptide or solvates of a salt of the compound, as well as unsolvated forms. The term "solvate" is used herein to describe a molecular complex comprising the compound of the invention and one or more pharmaceutically acceptable solvent molecules, for example, ethanol. The term "hydrate" is employed when said solvent is water. It is to be understood that all polymorphs, including mixtures of different polymorphs, are included within the scope of the claimed peptides.

6.2 Pharmaceutical Compositions.

The invention provides a pharmaceutical composition that includes a cyclic peptide of the present invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The cyclic peptide compositions of the present invention may be formulated or compounded into pharmaceutical compositions that include at least one cyclic peptide of the present invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxylpropyl cellulose, acacia, polyethylene glycol, mannitol, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, cellulose derivatives, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or sustained-release formulations and additives may be employed, so that the dosage may be formulated so as to provide delivery of a peptide of the present invention over a period of time.

In general, the actual quantity of cyclic peptides of the present invention administered to a patient will vary between fairly wide ranges depending on the mode of administration, the formulation used, and the response desired.

In practical use, the cyclic peptides of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent a convenient oral dosage unit form. If desired, tablets may be coated by standard aqueous or nonaqueous techniques. The amount of active peptide in such therapeutically useful compositions is such that an effective dosage will be obtained. In another dosage unit form, sublingual constructs may be employed, such as sheets, wafers, tablets or the like.

The tablets, pills, capsules, and the like may also contain a binder such as povidone, gum tragacanth, acacia, corn starch or gelatin; diluents; fillers such as microcrystalline cellulose; excipients such as dicalcium phosphate; a disintegrating agent such as corn starch, potato starch or alginic acid; preservatives; colorants; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Cyclic peptides may also be administered parenterally. Solutions or suspensions of these active peptides can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The cyclic peptides of the present invention may be therapeutically applied by means of nasal administration. By "nasal administration" is meant any form of intranasal administration of any of the cyclic peptides of the present invention. The peptides may be in an aqueous solution, such as a solution including saline, citrate or other common excipients or preservatives. The peptides may also be in a dry or powder formulation.

The cyclic peptides of the present invention may be formulated with any of a variety of agents that increase effective nasal absorption of drugs, including peptide drugs. These agents may increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, the cyclic peptides may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, and the like, a 50 mM solution may be employed. In addition to buffering agents, a suitable preservative may be employed, to prevent or limit bacteria and other microbial growth. One such preservative that may be employed is 0.05% benzalkonium chloride.

In an alternative embodiment, cyclic peptides of the present invention may be administered directly into the lung. Intrapulmonary administration may be performed by means of a metered dose inhaler, a device allowing self-administration of a metered bolus of a peptide of the present invention when actuated by a patient during inspiration. In one aspect of this embodiment, the cyclic peptide may be in a dried and particulate form, for example particles between about 0.5 and 6.0 μm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multi-dose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 μm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

The cyclic peptides of the present invention may be therapeutically administered by means of an injection of a sustained release formulation. In one embodiment, a cyclic peptide of the present invention is formulated for a deep intramuscular injection, such as in the gluteal or deltoid muscle, of a formulation with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a cyclic peptide of the present invention is formulated with a poly(ortho ester), which may be an autocatalyzed poly(ortho ester) with any of a variable percentage of lactic acid in the polymeric backbone, and optionally one or more additional excipients. In one embodiment poly (D,L-lactide-co-glycolide) polymer is employed. In general, any of a number of injectable and bioerodible polymers, which are preferably also adhesive polymers, may be employed in a sustained release injectable formulation. Alternatively other sustained release formulations may be employed, including formulations permitting subcutaneous injection, which other formulations may include one or more of nano/microspheres (such as compositions including PLGA polymers), liposomes, emulsions (such as water-in-oil emulsions), gels, insoluble salts or suspensions in oil. The formulation may be such that an injection is required on a daily, weekly, monthly or other periodic basis, depending on the concentration and amount of cyclic peptide, the sustained release rate of the materials employed, and other factors known to those of skill in the art.

6.3 Oral Formulations of Peptides of the Present Invention.

In one aspect, the peptides of the present invention are formulated for oral delivery. The peptide is preferably formulated and made such that it is encased in an enteric protectant, more preferably such that it is not released until the tablet or capsule has transited the stomach, and optionally has further transited a portion of the small intestine. In the context of this application it will be understood that the term enteric coating or material refers to a coating or material that will pass through the stomach essentially intact but will rapidly disintegrate in the small intestine to release the active drug substance. One enteric coating solution that may be used includes cellulose acetate phthalate, and optionally other ingredients such as ammonium hydroxide, triacetin, ethyl alcohol, methylene blue, and purified water. Cellulose acetate phthalate is a polymer that has been used in the pharmaceutical industry for enterically coating individual dosage forms such as tablets and capsules, and is not soluble in water at a pH of less than about 5.8. Enteric coatings including cellulose acetate phthalate provide protection against the acidic environment of the stomach, but begin to dissolve in environment of the duodenum (pH of about 6-6.5), and are completely dissolved by the time the dosage form reaches the ileum (pH of about 7-8). In addition to cellulose acetate phthalate, other enteric coating materials are known and may be used with peptides of the present invention, including without limitation hydroxypropylmethylethylcellulose succinate, hydroxypropylmethylcellulose phthalate, polyvinyl acetate phthalate, and methacrylic acid-methyl methacrylate copolymer. The enteric coating employed promotes dissolution of the dosage form primarily at a site outside the stomach, and may be selected such that the enteric coating dissolves at a pH of approximately at least 6.0, more preferable at a pH of from about 6.0 to about 8.0. In one preferred aspect, the enteric coating dissolves and breaks down in the proximity of the ileum.

Any of a variety of permeation enhancers may be employed, to increase uptake in the intestines upon dissolution of the enteric coating. In one aspect, permeation enhancers increase either paracellular or transcellular transport systems. An increase in paracellular transport can be achieved by opening the tight junctions of the cells; an increase in transcellular transport can be achieved by increasing the fluidity of the cell membrane. Representative, non-limiting examples of such permeation enhancers include calcium chelators, bile salts (such as sodium cholate), and fatty acids. The peptides of the present invention may be in an enteric-coated individual dosage form that includes a fatty acid, such as for example oleate, palmitate, stearate, sodium caprate, or conjugated linoleic acid, in an enteric-coated capsule, to increase paracellular transport.

In one aspect, the individual dosage form, such as a tablet or capsule, optionally further includes common pharmaceutical binders such as povidone, diluents, glidants, fillers such as microcrystalline cellulose, lubricants such as magnesium stearate, disintegrants such as croscarmellose sodium, preservatives, colorants and the like in their usual known sizes and amounts. In some embodiments, peptides or polypeptides that act as substrates for intestinal proteases are further added.

6.4 Ophthalmic Formulations.

In one embodiment, ocular diseases, indications, conditions and syndromes, such as for example either dry eye disease or uveitis, may be treated with an ophthalmic dosage form including one or more of the peptides of the present invention. The ophthalmic dosage form may include one or more active ingredients in addition to one or more of the peptides of the present invention, such as for example artificial tear components, topical corticosteroids, non-steroidal anti-inflammatory drugs, or calcineurin inhibitors such as cyclosporine-A (Restasis®—Allergan). In a related embodiment, one or additional compounds may be given separately from one or more of the peptides of the present invention, such as separate administration of an ophthalmic dosage form including an artificial tear component, a topical corticosteroid, a non-steroidal anti-inflammatory drugs, a calcineurin inhibitor such a cyclosporine-A, or a combination of any of the foregoing.

6.5 Routes of Administration.

If a composition including one or more peptides of the present invention is administered by injection, the injection may be intravenous, subcutaneous, intramuscular, intraperitoneal or other means known in the art. The peptides of the present invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, and the like.

6.6 Therapeutically Effective Amount.

In general, the actual quantity of cyclic peptide of the present invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a peptide or pharmaceutical composition of the present invention that is sufficient to therapeutically alleviate sexual dysfunction in a patient, or to prevent or delay onset or recurrence of the sexual dysfunction.

In general, the cyclic peptides of the present invention are highly active. For example, the cyclic peptide can be administered at about 0.1, 0.5, 1, 5, 50, 100, 500, 1000 or 5000 µg/kg body weight, depending on the specific peptide selected, the desired therapeutic response, the route of administration, the formulation and other factors known to those of skill in the art.

7.0 Peptides of the Present Invention

In one aspect, the invention provides a cyclic heptapeptide which contains a core sequence derived from His-Phe-Arg-Trp within the cyclic portion, and where the amino acid in the first position is outside the cyclic portion and has a side chain including at least one primary amine, guanidine or urea group. Representative amino acids which may be in the first position include, but are not limited to, Dap, Dab, Orn, Lys, Cit or Arg.

The core sequence derived from His-Phe-Arg-Trp will include unsubstituted D-Phe, D-Nal 1 or D-Nal 2 in the Phe position, but typically a variety of amino acids may be utilized for the remaining amino acids in the core sequence. In general, the His position may be a substituted or unsubstituted Pro, or may be an amino acid with a side chain including at least one primary amine, secondary amine, alkyl, cycloalkyl, cycloheteroalkyl, aryl, heteroaryl, alcohol, ether, sulfide, sulfone, sufoxide, carbornyl or carboxyl. The Arg position may be a substituted or unsubstituted Pro, or may be an amino acid with a side chain including at least one primary amine, secondary amine, guanidine, urea, alkyl, cycloalkyl, cycloheteroalkyl, aryl, heteroaryl, or ether. The Trp position may be an amino acid with a side chain including at least one substituted or unsubstituted aryl or heteroaryl.

Lactam-bridges are preferred for making the peptide cyclic, but other bridging groups are possible and contemplated, including specifically the groups:

—(CH$_2$)$_x$—C(=O)—NH—(CH$_2$)$_y$—,
—(CH$_2$)$_x$—NH—C(=O)—(CH$_2$)$_y$—,
—(CH$_2$)$_x$—C(=O)—(CH$_2$)$_z$—C(=O)—(CH$_2$)$_y$—,
—(CH$_2$)$_x$—C(=O)—NH—C(=O)—(CH$_2$)$_y$—, or
—(CH$_2$)$_x$—NH—C(=O)—NH—(CH$_2$)$_y$—;

where x and y are each independently 1 to 5. For certain indications and uses, including without limitation for peptides more selective for MC4-R than for MC1-R or, in general, for other melanocortin receptors, particularly preferred are the bridging groups —(CH$_2$)$_2$—C(=O)—NH—(CH$_2$)$_3$— and —(CH$_2$)$_2$—NH—C(=O)—(CH$_2$)$_2$—. In this context, the teachings of U.S. patent application Ser. No. 13/311,817 and International Application No. PCT/US2010/037584, published as International Publication No. WO 2010/144341, entitled "Lactam-Bridged Melanocortin Receptor-Specific Peptides", filed on Jun. 7, 2010, are incorporated herein by reference as if set forth in full.

The peptides encompassed within formulas (I) and (II) contain one or more asymmetric elements such as stereogenic centers, stereogenic axes and the like, so that the peptides encompassed within formula (I) can exist in different stereoisomeric forms. For both specific and generically described peptides, including the peptides encompassed within formulas (I) and (II), all forms of isomers at all chiral or other isomeric centers, including enantiomers and diastereomers, are intended to be covered herein. The peptides of the invention each include multiple chiral centers, and may be used as a racemic mixture or an enantiomerically enriched mixture, in addition to use of the peptides of the invention in enantiopure preparations. Typically, the peptides of the invention will be synthesized with the use of chirally pure reagents, such as specified L- or D-amino acids, using reagents, conditions and methods such that enantiomeric purity is maintained, but it is possible and contemplated that racemic mixtures may be made. Such racemic mixtures may optionally be separated using well-known techniques and an individual enantiomer may be used alone. In cases and under specific conditions of temperature, solvents and pH wherein peptides may exist in tautomeric forms, each tautomeric form is contemplated as being included within this invention whether existing in equilibrium or predominantly in one form. Thus a single enantiomer of a peptide of formula (I), which is an optically active form, can be obtained by asymmetric synthesis, synthesis from optically pure precursors, or by resolution of the racemates.

The invention is further intended to include prodrugs of the present peptides, which on administration undergo chemical conversion by metabolic processes before becoming active pharmacological peptides. In general, such prodrugs will be functional derivatives of the present peptides, which are readily convertible in vivo into a peptide of formulas (I) or (II). Prodrugs are any covalently bonded compounds, which release the active parent peptide drug of formulas (I) or (II) in vivo. Conventional procedures for the selection and preparation of suitable prodrug derivatives are described, for example, in *Design of Prodrugs*, ed. H. Bundgaard, Elsevier, 1985. Typical examples of prodrugs have biologically labile protecting groups on a functional moiety, such as for example by esterification of hydroxyl, carboxyl or amino functions. Thus by way of example and not limitation, a prodrug includes peptides of formula (I) wherein an ester prodrug form is employed, such as, for example, lower alkyl esters of an R group of formula (I), such as where R is —OH, which lower alkyl esters may include from 1-8 carbons in an alkyl radical or aralkyl esters which have 6-12 carbons in an aralkyl radical. Broadly speaking, prodrugs include compounds that can be oxidized, reduced, aminated, deaminated, hydroxylated, dehydroxylated, hydrolyzed, dehydrolyzed, alkylated, dealkylated, acylated, deacylated, phosphorylated or dephosphorylated to produce an active parent peptide drug of formula (I) in vivo.

The subject invention also includes peptides which are identical to those recited in formula (I), but for the fact that one or more atoms depicted in formula (I) are replaced by an atom having an atomic mass or mass number different from the atomic mass or mass number usually found in nature. Examples of isotopes that can be incorporated into compounds of the invention include isotopes of hydrogen, carbon, nitrogen and oxygen, such as $^2$H, $^3$H, $^{13}$C, $^{14}$C, $^{15}$N, $^{18}$O and $^{17}$O, respectively. Peptides of the present invention and pharmaceutically acceptable salts or solvates of said compounds which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, may have use in a variety of assays, such as in drug and/or substrate tissue distribution assays. Substitution with heavier isotopes, such as substitution of one or more hydrogen atoms with deuterium ($^2$H), can provide pharmacological advantages in some instances, including increased metabolic stability. Isotopically labeled peptides of formula (I) can generally be prepared by substituting an isotopically labeled reagent for a non-isotopically labeled reagent.

8.0 Tests and Assays Employed in Evaluation of the Peptides of the Present Invention The melanocortin receptor-specific peptides of the present invention of this invention may be tested by a variety of assay systems and animal models to determine binding, functional status and efficacy.

8.1 Competitive Inhibition Assay Using [I$^{125}$]-NDP-α-MSH.

A competitive inhibition binding assay is performed using membrane homogenates prepared from HEK-293 cells that express recombinant hMC4-R, hMC3-R, or hMC5-R, and from B-16 mouse melanoma cells (containing endogenous MC1-R). In some instances, HEK-293 cells that express recombinant hMC1-R were employed. In the examples that follow, all MC3-R, MC4-R and MC5-R values are for human recombinant receptors. MC1-R values are for B-16 mouse melanoma cells, unless the heading is "hMC1-R", in which case the value is for human recombinant MC1-R. Assays were performed in 96 well GF/B Millipore multiscreen filtration plates (MAFB NOB10) pre-coated with 0.5% bovine serum albumin (Fraction V). Membrane homogenates were incubated with 0.2 nM (for hMC4-R) 0.4 nM (for MC3-R and MC5-R) or 0.1 nM (for mouse B16 MC1-R or hMC1-R) [$I^{125}$]-NDP-α-MSH (Perkin Elmer) and increasing concentrations of test peptides of the present invention in buffer containing 25 mM HEPES buffer (pH 7.5) with 100 mM NaCl, 2 mM $CaCl_2$, 2 mM $MgCl_2$, 0.3 mM 1,10-phenanthroline, and 0.2% bovine serum albumin. After incubation for 60 minutes at 37° C., the assay mixture was filtered and the membranes washed three times with ice-cold buffer. Filters were dried and counted in a gamma counter for bound radioactivity. Non-specific binding was measured by inhibition of binding of [$I^{125}$]-NDP-α-MSH in the presence of 1 μM NDP-α-MSH. Maximal specific binding (100%) was defined as the difference in radioactivity (cpm) bound to cell membranes in the absence and presence of 1 μM NDP-α-MSH. Radioactivity (cpm) obtained in the presence of test compounds was normalized with respect to 100% specific binding to determine the percent inhibition of [$I^{125}$]-NDP-α-MSH binding. Each assay was conducted in triplicate and the actual mean values are described, with results less than 0% reported as 0%. Ki values for test peptides of the present invention were determined using Graph-Pad Prism® curve-fitting software.

8.2 Competitive Binding Assay Using Eu-NDP-α-MSH

Alternatively, a competitive inhibition binding assay was performed employing Eu-NDP-α-MSH (PerkinElmer Life Sciences catalog No. AD0225) with determination by time-resolved fluorometry (TRF) of the lanthanide chelate. In comparison studies with [$I^{125}$]-NDP-α-MSH, the same values, within experimental error ranges, were obtained for percent inhibition and Ki. Typically competition experiments to determine Ki values were conducted by incubating membrane homogenates prepared from HEK-293 cells that express recombinant hMC4-R with 9 different concentrations of test compounds of interest and 2 nM of Eu-NDP-α-MSH in a solution containing 25 mM HEPES buffer with 100 mM NaCl, 2 mM $CaCl_2$, 2 mM $MgCl_2$ and 0.3 mM 1,10-phenanthroline. After incubation for 90 minutes at 37° C., the reaction was stopped by filtration over AcroWell 96-well filter plates (Pall Life Sciences). The filter plates were washed 4 times with 200 μL of ice-cold phosphate-buffered saline. DELFIA Enhancement solution (PerkinElmer Life Sciences) was added to each well. The plates were incubated on a shaker for 15 minutes and read at 340 nm excitation and 615 nm emission wavelengths. Each assay was conducted in duplicate and mean values were utilized. Ki values were determined by curve-fitting with Graph-Pad Prism® software using a one-site fixed-slope competition binding model.

8.3 Competitive Binding Assay Using [$I^{125}$]-AgRP (83-132).

Competitive binding studies using [$I^{125}$]-AgRP (83-132) are carried out using membrane homogenates isolated from cells that express hMC4-R. The assays were performed in 96-well GF/B Millipore multiscreen filtration plates (MAFB NOB10) pre-coated with 0.5% bovine serum albumin (Fraction V). The assay mixture contained 25 mM HEPES buffer (pH 7.5) with 100 mM NaCl, 2 mM $CaCl_2$, 2 mM $MgCl_2$, 0.3 mM 1,10-phenanthroline, 0.5% bovine serum albumin, membrane homogenates, radioligand [$I^{125}$]-AgRP (83-132) (Perkin Elmer) and increasing concentrations of peptides of the present invention in a total volume of 200 μL. Binding was measured at radioligand concentrations of 0.2 nM. After incubating for 1 hour at 37° C., the reaction mixture was filtered and washed with assay buffer containing 500 mM NaCl. The dried discs were punched out from the plate and counted on a gamma counter. Ki values for test peptides of the present invention were determined using Graph-Pad Prism® curve-fitting software.

8.4 Assay for Agonist Activity.

Accumulation of intracellular cAMP was examined as a measure of the ability of the peptides of the present invention to elicit a functional response in HEK-293 cells that express MC4-R. Confluent HEK-293 cells that express recombinant hMC4-R were detached from culture plates by incubation in enzyme-free cell dissociation buffer. Dispersed cells were suspended in Earle's Balanced Salt Solution containing 10 mM HEPES (pH 7.5), 1 mM $MgCl_2$, 1 mM glutamine, 0.5% albumin and 0.3 mM 3-isobutyl-1-methyl-xanthine (IBMX), a phosphodiesterase inhibitor. The cells were plated in 96-well plates at a density of $0.5 \times 10^5$ cells per well and pre-incubated for 10 minutes. Cells were exposed for 15 minutes at 37° C. to peptides of the present invention dissolved in DMSO (final DMSO concentration of 1%) at a concentration range of 0.05-5000 nM in a total assay volume of 200 μL. NDP-α-MSH was used as the reference agonist. cAMP levels were determined by an HTRF® cAMP cell-based assay system from Cisbio Bioassays utilizing cryptate-labeled anti-cAMP and d2-labeled cAMP, with plates read on a Perkin-Elmer Victor plate reader at 665 and 620 nM. Data analysis was performed by nonlinear regression analysis with Graph-Pad Prism® software. The maximum efficacies of the test peptides of the present invention were compared to that achieved by the reference melanocortin agonist NDP-αMSH.

8.5 Food Intake and Body Weight Change.

Change in food intake and body weight was evaluated for selected peptides administered by intravenous (IV) or subcutaneous injection routes. Male Sprague-Dawley rats were obtained from Hilltop Lab Animals, Inc. (Scottsdale, Pa.) or other vendors. Animals were individually housed in conventional polystyrene hanging cages and maintained on a controlled 12 hour on/off light cycle. Water and pelleted food was provided ad libitum. The rats were dosed IV with vehicle or selected peptides (0.3 to 1.0 mg/kg), or dosed subcutaneously with vehicle or selected peptides (doses up to 30 mg/kg). The changes in body weight and food intake for the 24 hour period after dosing was determined. The changes in body weight and food intake for the 48 hour and 72 hour periods after dosing can also be measured to determine reversal of changes in body weight and food intake effects back to baseline levels.

8.6 Induction of Penile Erection.

The ability of peptides of the present invention to induce penile erection (PE) in male rats were evaluated with selected peptides. Male Sprague-Dawley rats weighing 250-300 g were kept on a 12 hour on/off light cycle with food and water ad libitum. All behavioral studies were performed between 9 a.m. and 4 p.m. Groups of 6-8 rats were administered peptides at a variety of doses via an IV or subcutaneous injection route. Immediately after treatment, rats were placed into individual polystyrene cages (27 cm long, 16 cm wide, and 25 cm high) for behavioral observation, typically by remote video monitoring. Rats are observed for one hour, and the number of yawns, grooming bouts and PEs are recorded in 10-minute bins.

9.0 Examples

The invention is further exemplified by the following non-limiting examples:

9.1 Peptides of the following structures were synthesized by the general methods described above, and averaged MC4-R Ki values for peptides were determined as indicated. All Ki values were determined using [$I^{125}$]-NDP-α-MSH unless marked with an "*", in which event the values were determined using Eu-NDP-α-MSH. Ki values marked "ND" were not determined.

| No. | Structure | Amino Acid Sequence | MC4-R Ki (nM) |
|---|---|---|---|
| 1 | 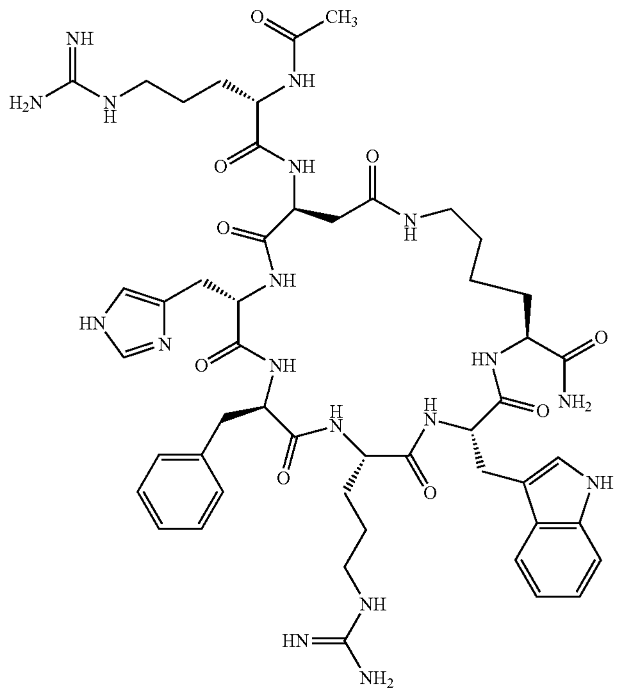 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-cyclo(Asp-His-D-Phe-Arg-Trp-Lys)-NH₂ | 5 |
| 2 | 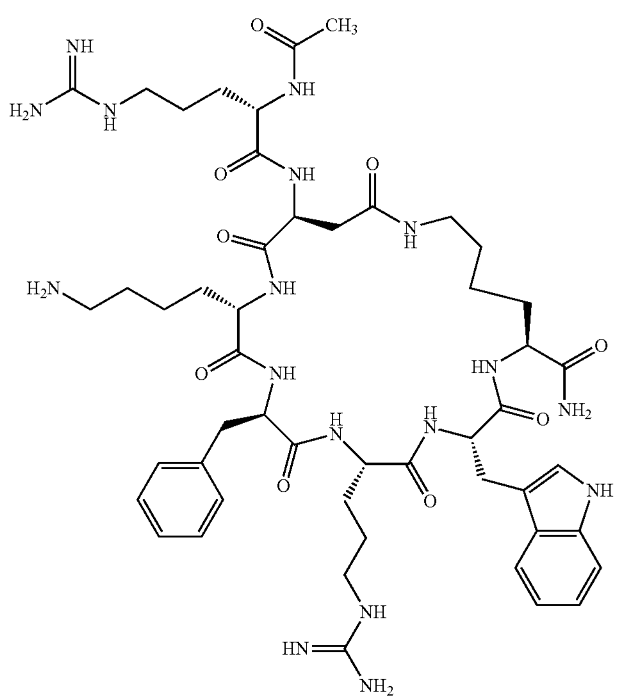 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCCCN)NC1=O] | Ac-Arg-cyclo(Asp-Lys-D-Phe-Arg-Trp-Lys)-NH₂ | 30 |

| No. | Structure | Amino Acid Sequence | MC4-R Ki (nM) |
|---|---|---|---|
| 3 | 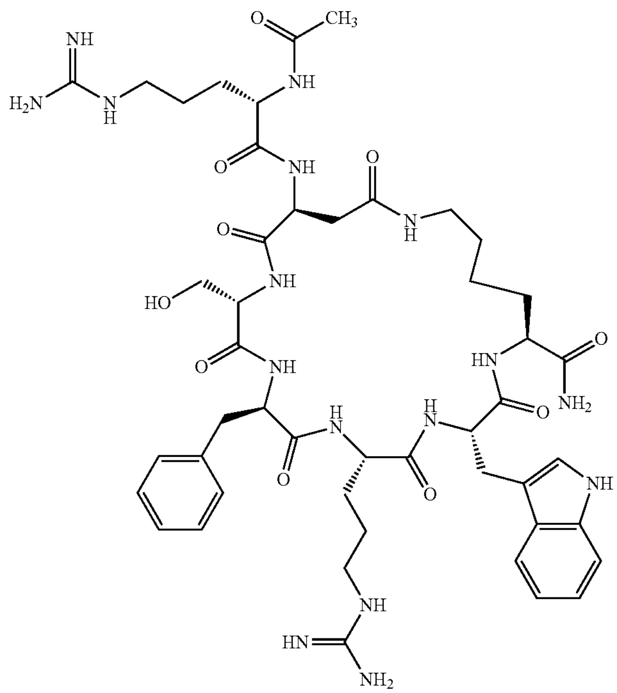 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CO)NC1=O] | Ac-Arg-cyclo(Asp-Ser-D-Phe-Arg-Trp-Lys)-NH$_2$ | 172 |
| 4 | 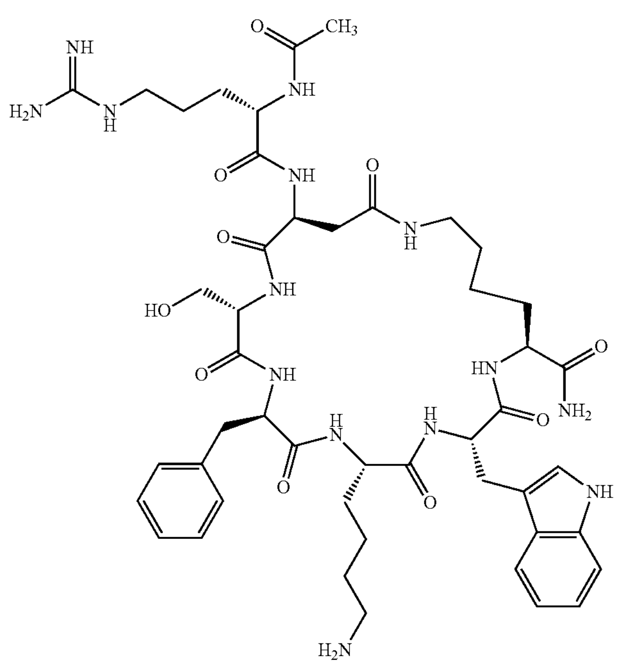 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCCN)NC(=O)[C@@H](Cc2ccccc2)NC(=O)[C@H](CO)NC1=O] | Ac-Arg-cyclo(Asp-Ser-D-Phe-Lys-Trp-Lys)-NH$_2$ | 4293 |

| No. | Structure | Amino Acid Sequence | MC4-R Ki (nM) |
|---|---|---|---|
| 5 | 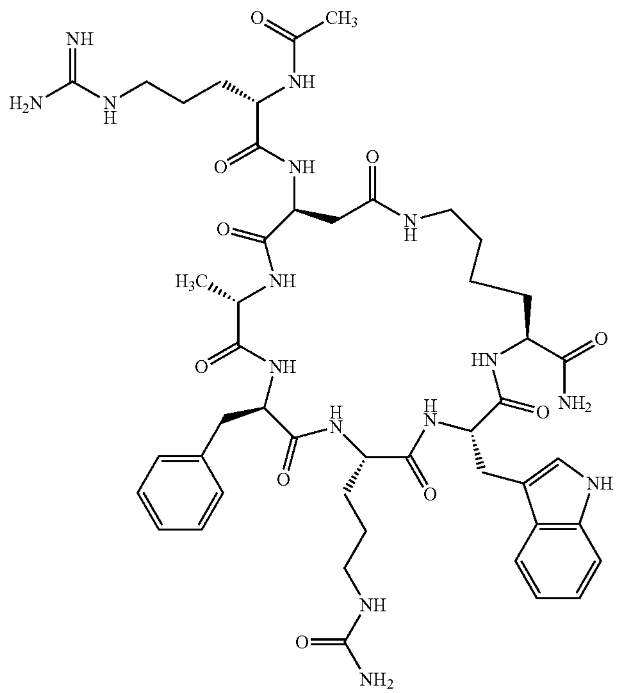 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(N)=O)NC(=O)[C@@H](Cc2ccccc2)NC(=O)[C@H](C)NC1=O] | Ac-Arg-cyclo(Asp-Ala-D-Phe-Cit-Trp-Lys)-NH$_2$ | 2048* |
| 6 | 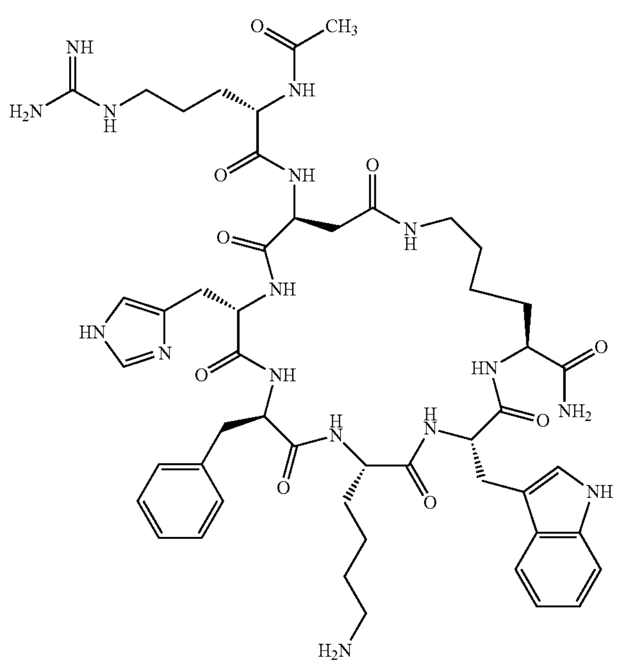 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCCN)NC(=O)[C@@H](Cc2ccccc2)NC(=O)[C@H](Cc2c[nH]cn2)NC1=O] | Ac-Arg-cyclo(Asp-His-D-Phe-Lys-Trp-Lys)-NH$_2$ | 533* |

| No. | Structure | Amino Acid Sequence | MC4-R Ki (nM) |
|---|---|---|---|
| 7 | 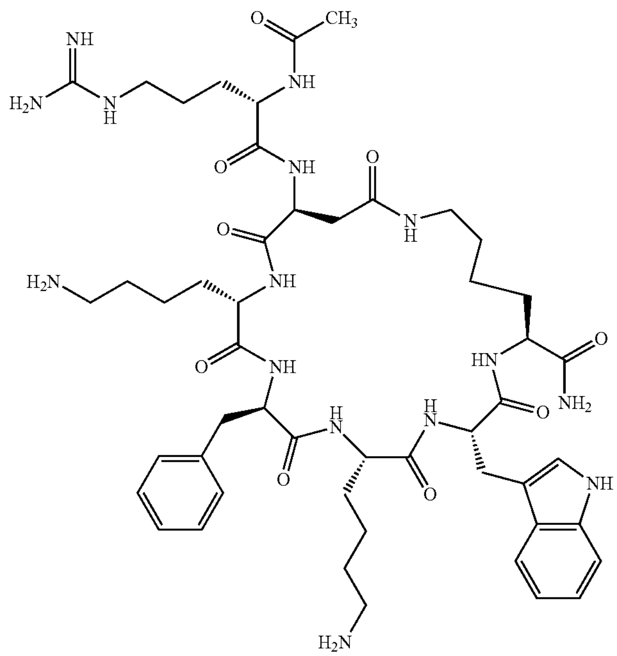 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCCN)NC(=O)[C@@H](Cc2ccccc2)NC(=O)[C@H](CCCCN)NC1=O] | Ac-Arg-cyclo(Asp-Lys-D-Phe-Lys-Trp-Lys)-NH$_2$ | 2957* |
| 8 | 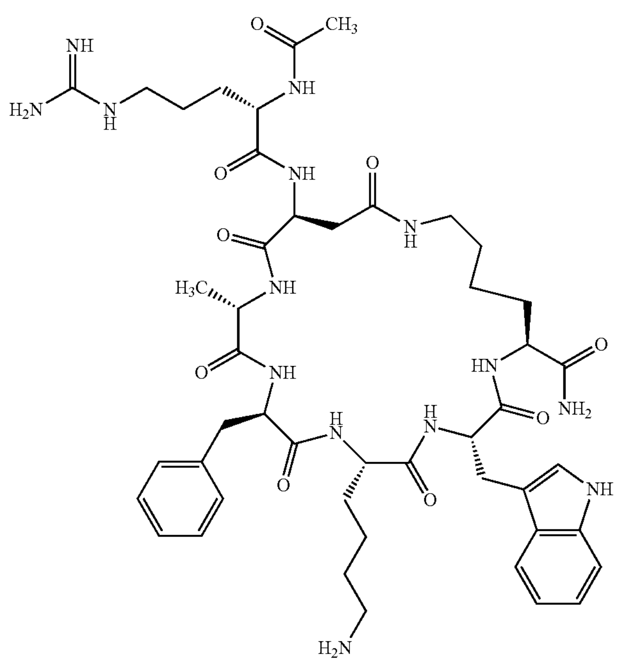 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCCN)NC(=O)[C@@H](Cc2ccccc2)NC(=O)[C@H](C)NC1=O] | Ac-Arg-cyclo(Asp-Ala-D-Phe-Lys-Trp-Lys)-NH$_2$ | 3018* |

| No. | Structure | Amino Acid Sequence | MC4-R Ki (nM) |
|---|---|---|---|
| 9 | 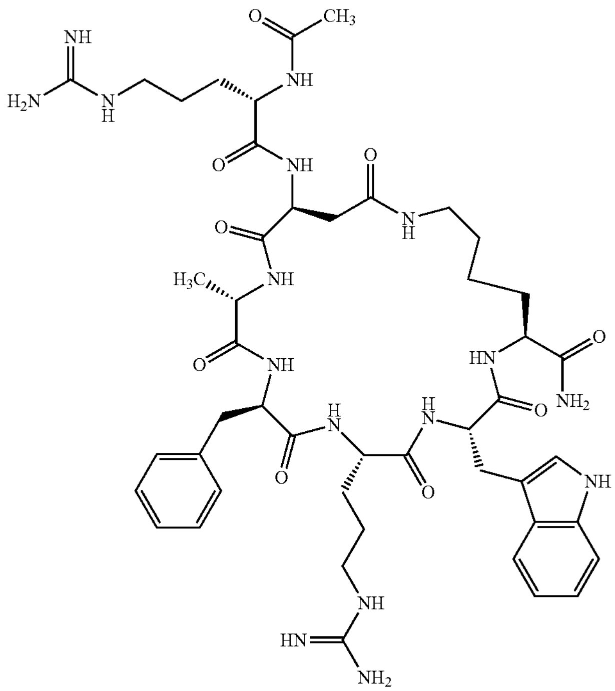 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](C)NC1=O] | Ac-Arg-cyclo(Asp-Ala-D-Phe-Arg-Trp-Lys)-NH₂ | 19* |
| 10 | 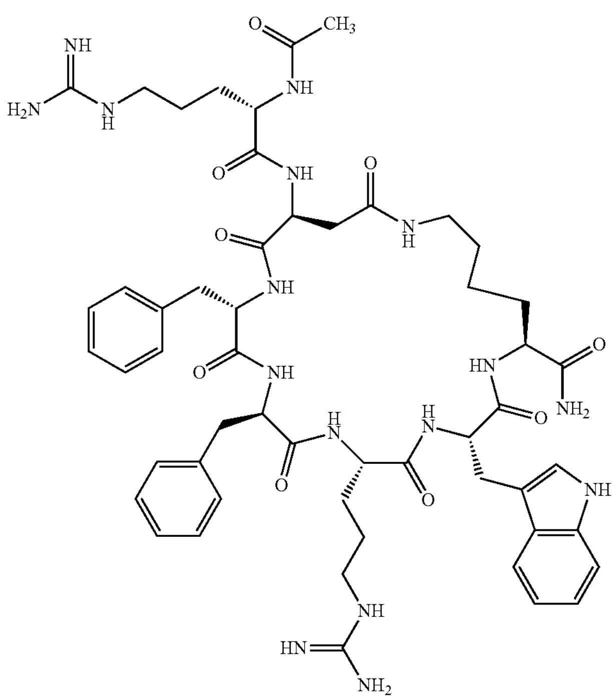 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2ccccc2)NC1=O] | Ac-Arg-cyclo(Asp-Phe-D-Phe-Arg-Trp-Lys)-NH₂ | 51* |

-continued

| No. | Structure | Amino Acid Sequence | MC4-R Ki (nM) |
|---|---|---|---|
| 11 | 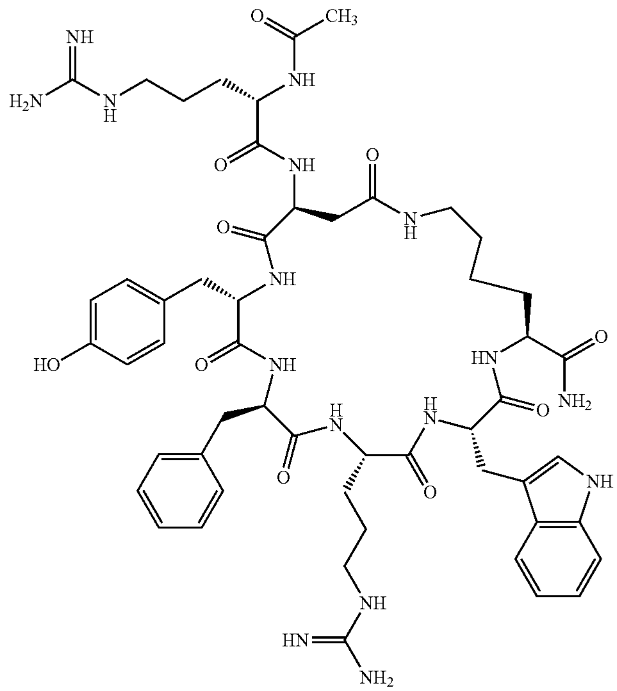 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2ccc(O)cc2)NC1=O] | Ac-Arg-cyclo(Asp-Tyr-D-Phe-Arg-Trp-Lys)-NH₂ | 43* |
| 12 | 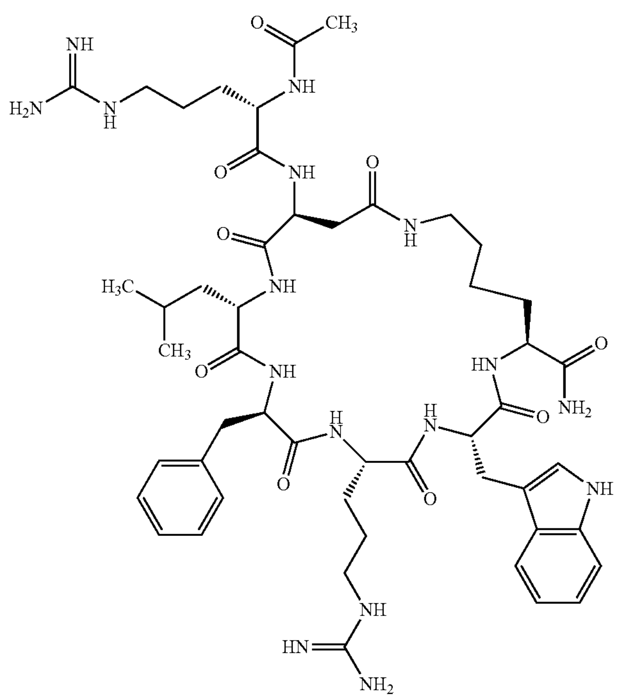 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CC(C)C)NC1=O] | Ac-Arg-cyclo(Asp-Leu-D-Phe-Arg-Trp-Lys)-NH₂ | 33* |

| No. | Structure | Amino Acid Sequence | MC4-R Ki (nM) |
|---|---|---|---|
| 13 | 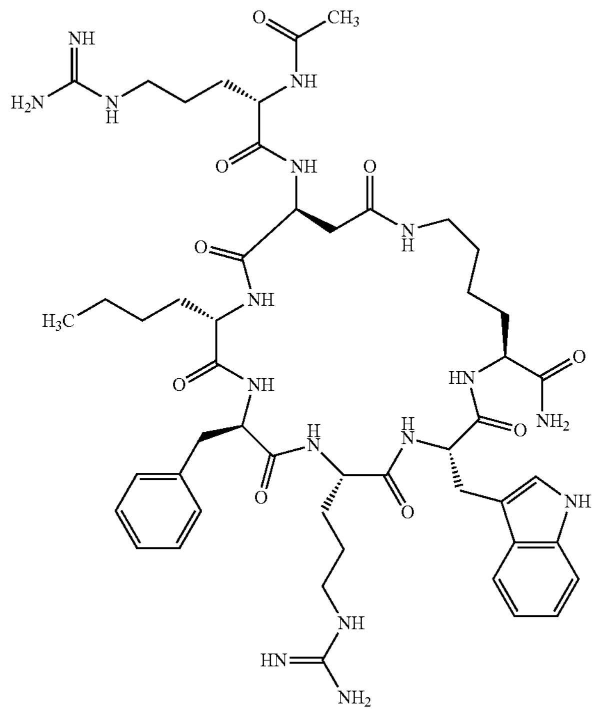 [SMILES: CCCC[C@@H]1NC(=O)[C@@H](NC(=O)[C@H](CCCNC(=N)N)NC(C)=O)CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC1=O] | Ac-Arg-cyclo(Asp-Nle-D-Phe-Arg-Trp-Lys)-NH₂ | 30* |
| 14 | 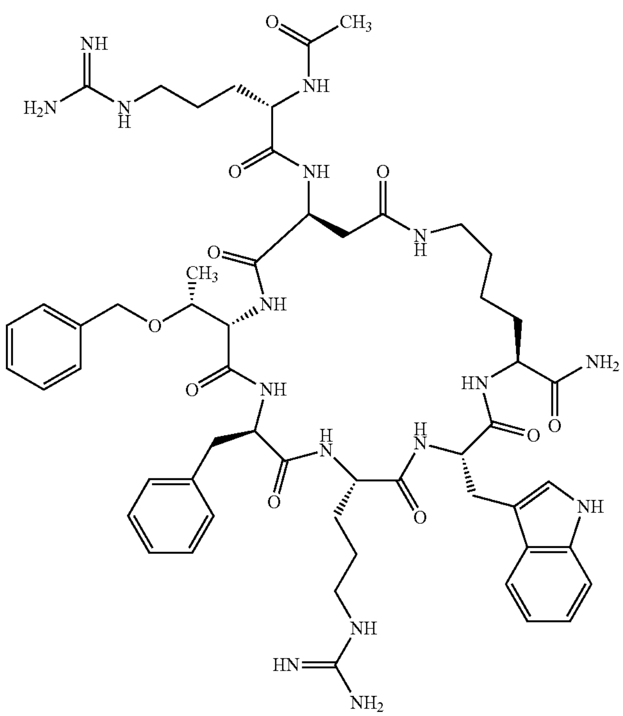 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H]([C@@H](C)OCc2ccccc2)NC1=O] | Ac-Arg-cyclo(Asp-Thr(Bzl)-D-Phe-Arg-Trp-Lys)-NH₂ | 1 |

-continued

| No. | Structure | Amino Acid Sequence | MC4-R Ki (nM) |
|---|---|---|---|
| 15 | 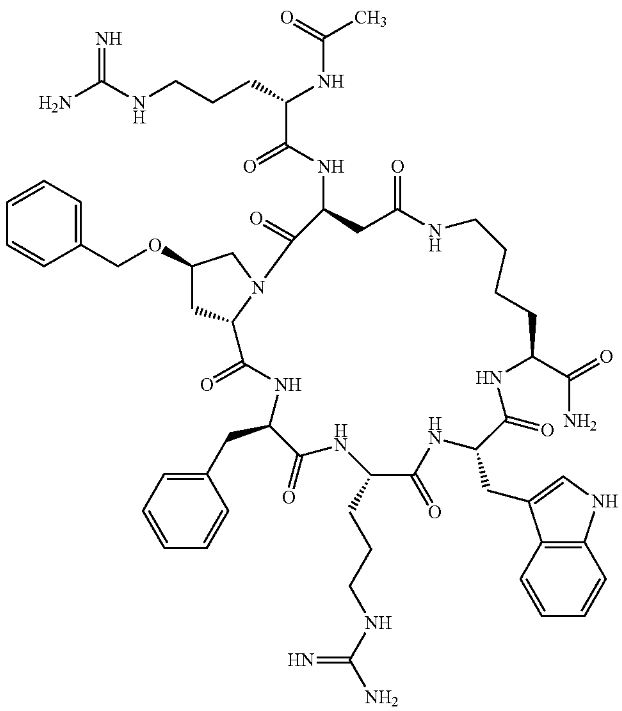 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]2C[C@@H](OCc3ccccc3)CN2C1=O] | Ac-Arg-cyclo(Asp-Hyp(Bzl)-D-Phe-Arg-Trp-Lys)-NH$_2$ | 0.7* |
| 16 | 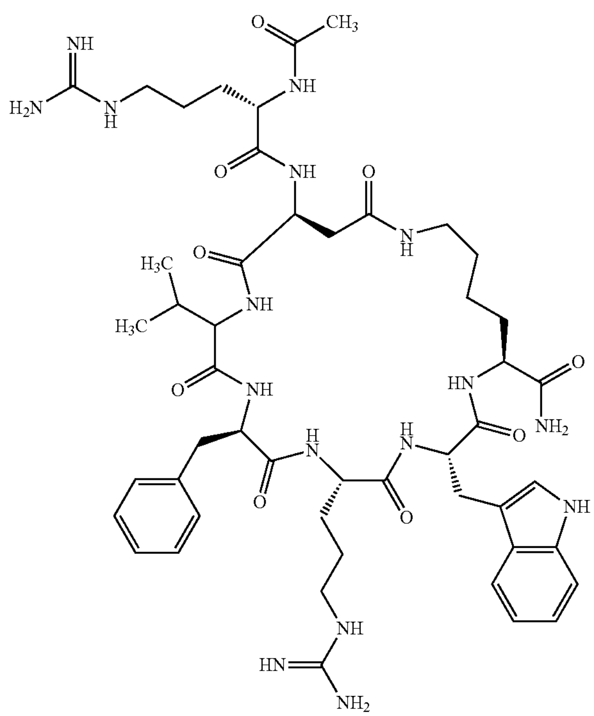 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)C(C(C)C)NC1=O] | Ac-Arg-cyclo(Asp-Val-D-Phe-Arg-Trp-Lys)-NH$_2$ | 23 |

-continued

| No. | Structure | Amino Acid Sequence | MC4-R Ki (nM) |
|---|---|---|---|
| 17 | 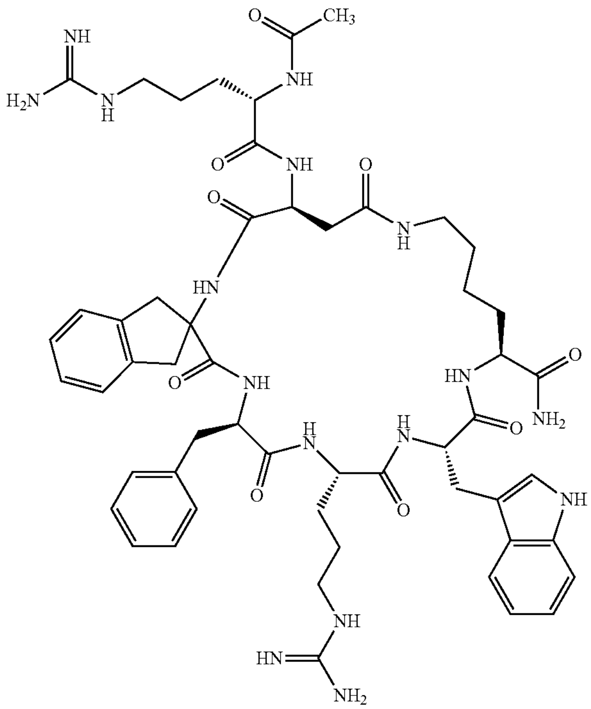 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)C2(Cc3ccccc3C2)NC1=O] | Ac-Arg-cyclo(Asp-Aic-D-Phe-Arg-Trp-Lys)-NH₂ | ND |
| 18 | 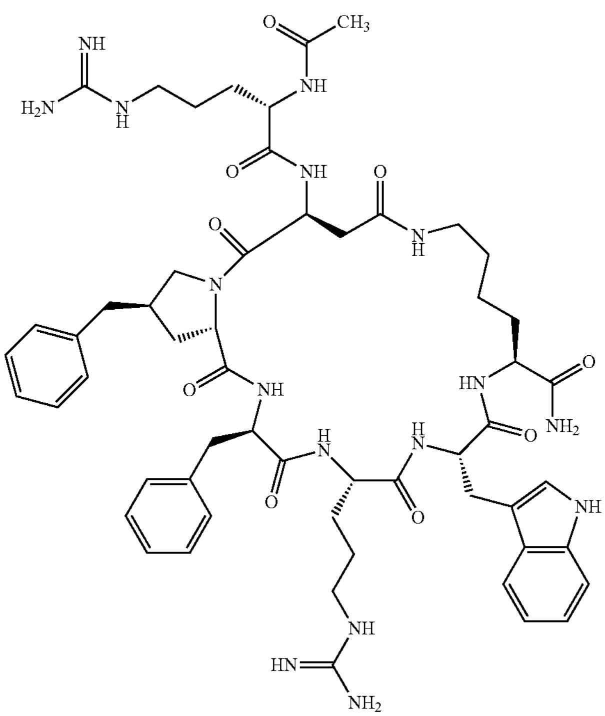 | Ac-Arg-cyclo(Asp-Pro(4R-Bzl)-D-Phe-Arg-Trp-Lys)-NH₂ | 3* |

-continued

| No. | Structure | Amino Acid Sequence | MC4-R Ki (nM) |
|---|---|---|---|
| 19 | 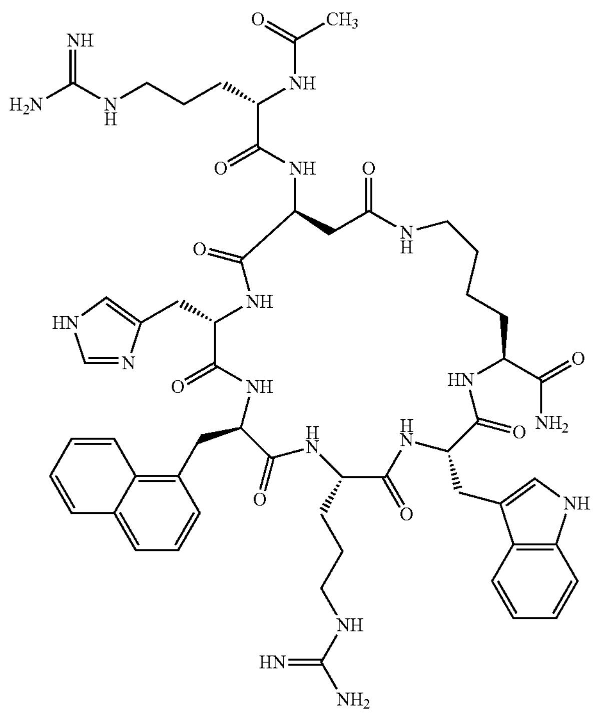 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2cccc3ccccc23)NC(=O)[C@H](Cc2c[nH]cn2)NC1=O] | Ac-Arg-cyclo(Asp-His-D-Nal 1-Arg-Trp-Lys)-NH2 | 3 |
| 20 | 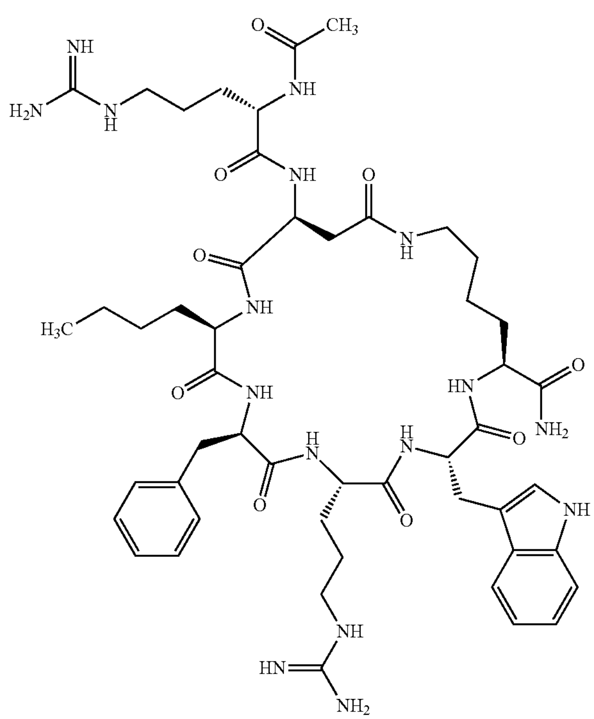 [SMILES: CCCC[C@H]1NC(=O)[C@@H](NC(=O)[C@H](CCCNC(=N)N)NC(C)=O)CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC1=O] | Ac-Arg-cyclo(Asp-D-Nle-D-Phe-Arg-Trp-Lys)-NH2 | ND |

-continued

| No. | Structure | Amino Acid Sequence | MC4-R Ki (nM) |
|---|---|---|---|
| 21 | 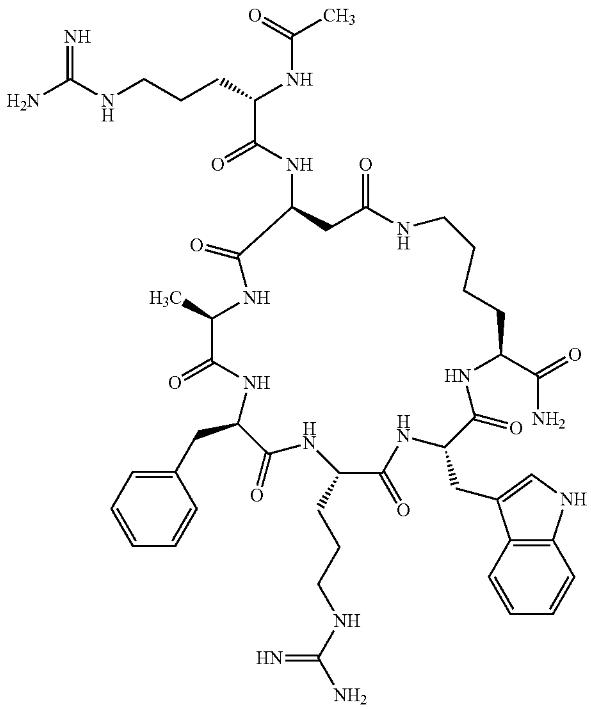 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H](C)NC1=O] | Ac-Arg-cyclo(Asp-D-Ala-D-Phe-Arg-Trp-Lys)-NH₂ | ND |
| 22 | 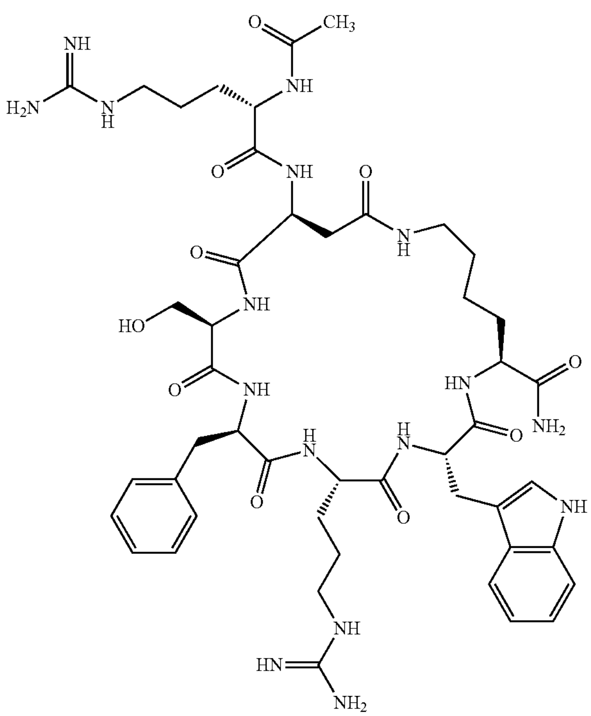 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H](CO)NC1=O] | Ac-Arg-cyclo(Asp-D-Ser-D-Phe-Arg-Trp-Lys)-NH₂ | ND |

| No. | Structure | Amino Acid Sequence | MC4-R Ki (nM) |
|---|---|---|---|
| 23 | 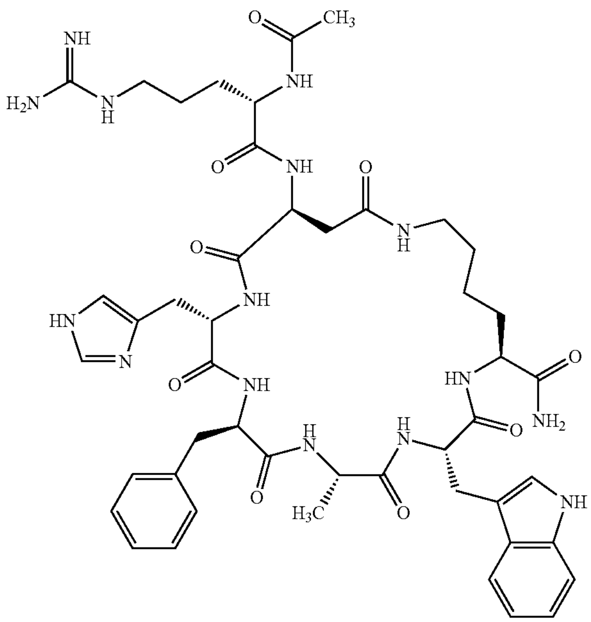 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](C)NC(=O)[C@@H](Cc2ccccc2)NC(=O)[C@H](Cc2c[nH]cn2)NC1=O] | Ac-Arg-cyclo(Asp-His-D-Phe-Ala-Trp-Lys)-NH2 | ND |
| 24 | 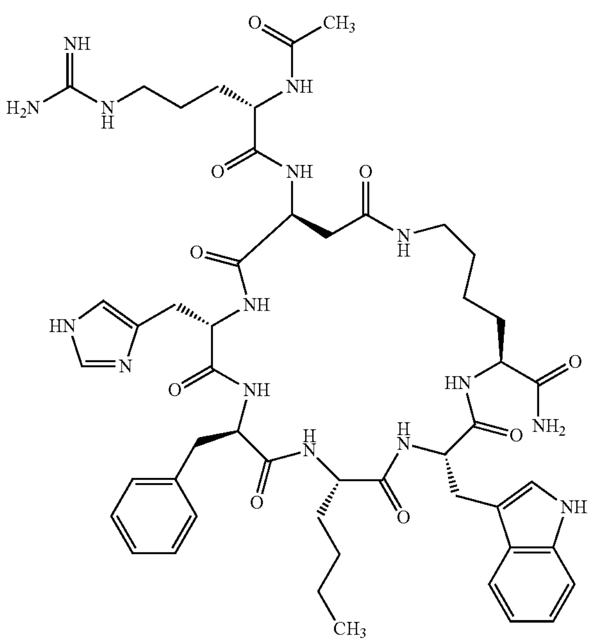 [SMILES: CCCC[C@@H]1NC(=O)[C@@H](Cc2ccccc2)NC(=O)[C@H](Cc2c[nH]cn2)NC(=O)[C@@H](NC(=O)[C@H](CCCNC(=N)N)NC(C)=O)CC(=O)NCCCC[C@@H](C(N)=O)NC(=O)[C@H](Cc2c[nH]c3ccccc23)NC1=O] | Ac-Arg-cyclo(Asp-His-D-Phe-Nle-Trp-Lys)-NH2 | ND |

-continued

| No. | Structure | Amino Acid Sequence | MC4-R Ki (nM) |
|---|---|---|---|
| 25 | 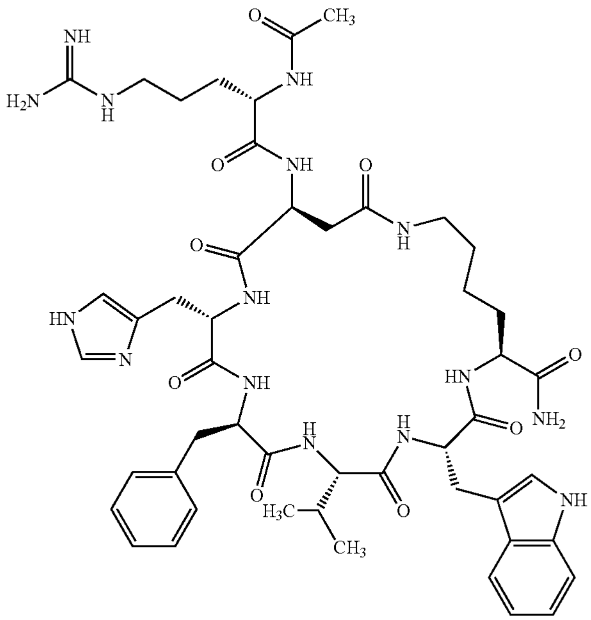 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](C(C)C)NC(=O)[C@@H](Cc2ccccc2)NC(=O)[C@H](Cc2c[nH]cn2)NC1=O] | Ac-Arg-cyclo(Asp-His-D-Phe-Val-Trp-Lys)-NH₂ | ND |
| 26 | 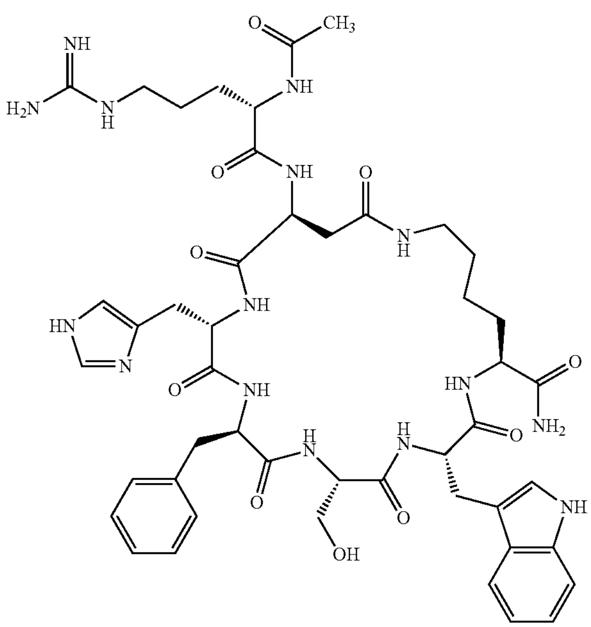 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CO)NC(=O)[C@@H](Cc2ccccc2)NC(=O)[C@H](Cc2c[nH]cn2)NC1=O] | Ac-Arg-cyclo(Asp-His-D-Phe-Ser-Trp-Lys)-NH₂ | ND |

| No. | Structure | Amino Acid Sequence | MC4-R Ki (nM) |
|---|---|---|---|
| 27 | 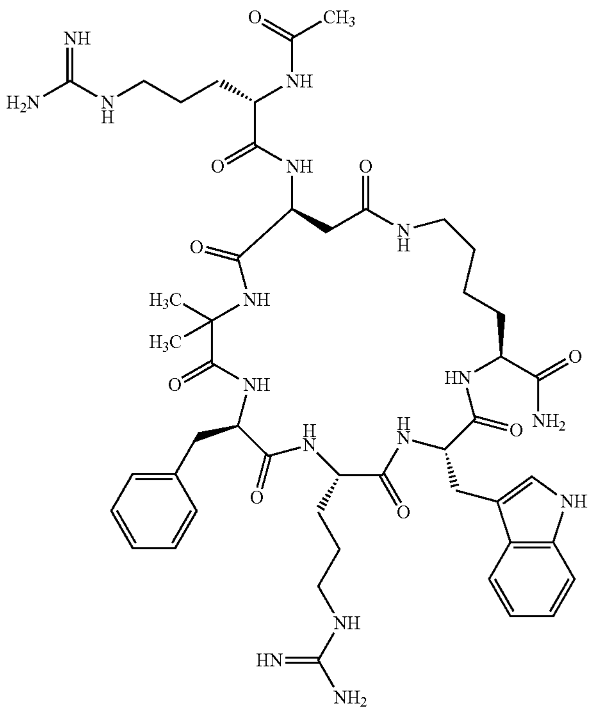 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)C(C)(C)NC1=O] | Ac-Arg-cyclo(Asp-Aib-D-Phe-Arg-Trp-Lys)-NH₂ | ND |
| 28 | 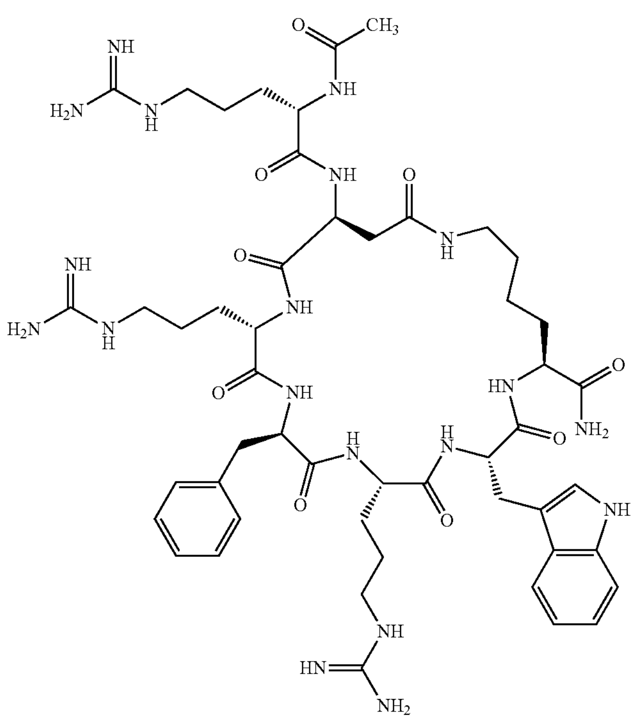 | Ac-Arg-cyclo(Asp-Arg-D-Phe-Arg-Trp-Lys)-NH₂ | 4* |

-continued

| No. | Structure | Amino Acid Sequence | MC4-R Ki (nM) |
|---|---|---|---|
| 29 | 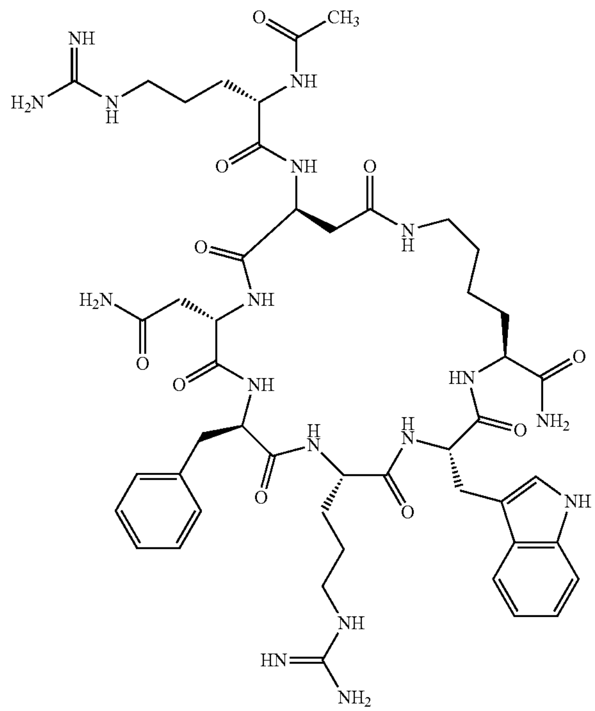 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O] | Ac-Arg-cyclo(Asp-Asn-D-Phe-Arg-Trp-Lys)-NH₂ | 32* |
| 30 | 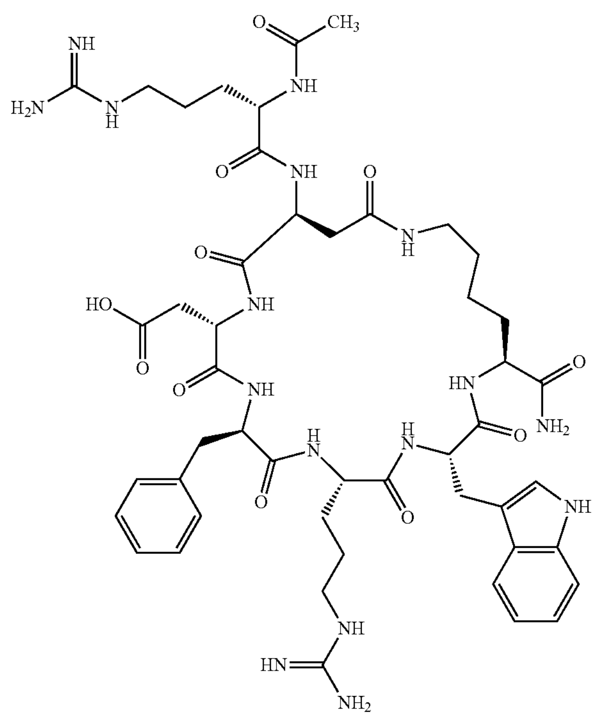 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CC(=O)O)NC1=O] | Ac-Arg-cyclo(Asp-Asp-D-Phe-Arg-Trp-Lys)-NH₂ | ND |

| No. | Structure | Amino Acid Sequence | MC4-R Ki (nM) |
|---|---|---|---|
| 31 | 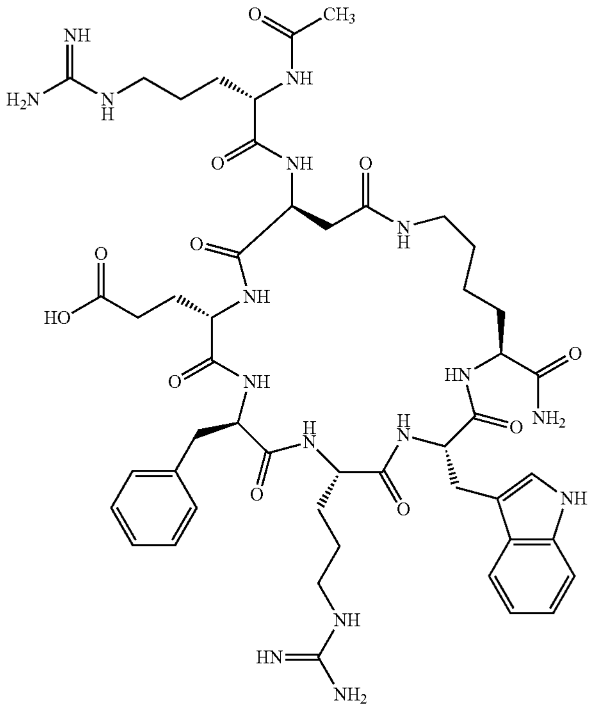 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCC(=O)O)NC1=O] | Ac-Arg-cyclo(Asp-Glu-D-Phe-Arg-Trp-Lys)-NH₂ | ND |
| 32 | 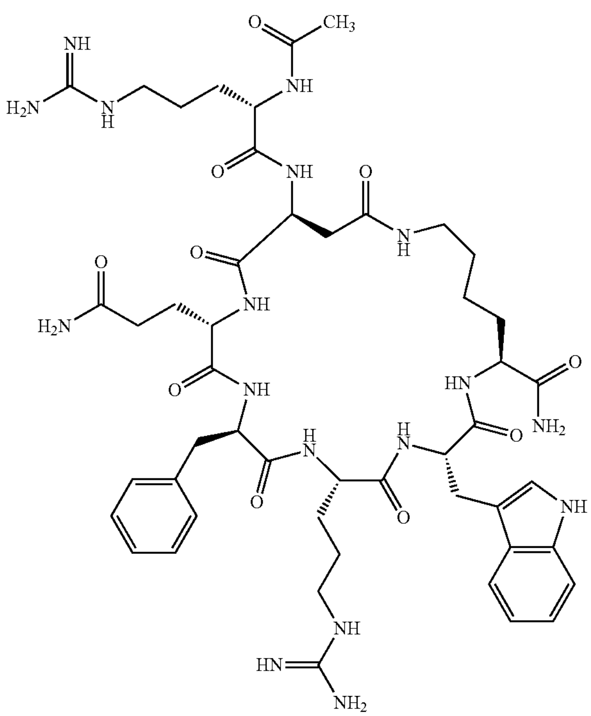 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-Arg-cyclo(Asp-Gln-D-Phe-Arg-Trp-Lys)-NH₂ | 13 |

-continued

| No. | Structure | Amino Acid Sequence | MC4-R Ki (nM) |
|---|---|---|---|
| 33 | 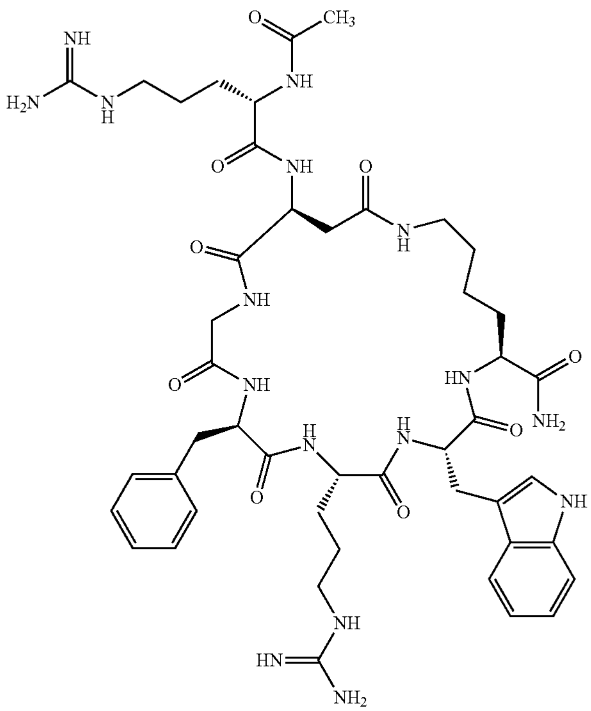 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)CNC1=O] | Ac-Arg-cyclo(Asp-Gly-D-Phe-Arg-Trp-Lys)-NH$_2$ | ND |
| 34 | 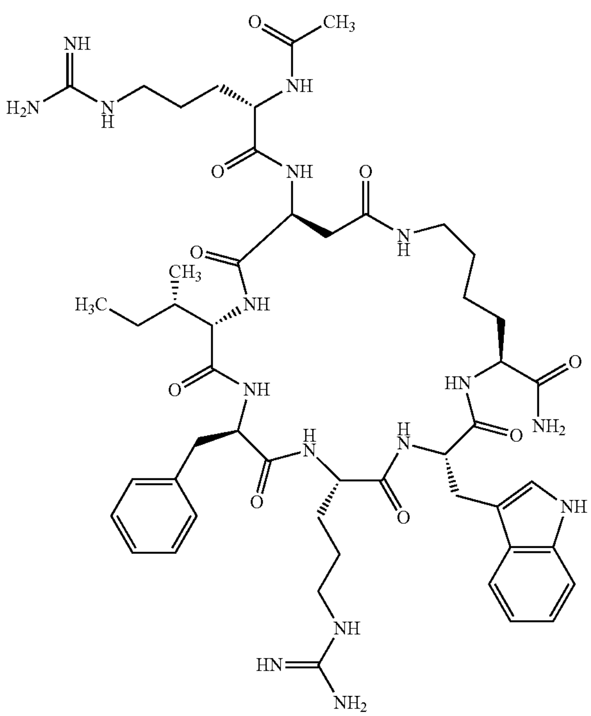 [SMILES: CC[C@H](C)[C@@H]1NC(=O)[C@@H](NC(=O)[C@H](CCCNC(=N)N)NC(C)=O)CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC1=O] | Ac-Arg-cyclo(Asp-Ile-D-Phe-Arg-Trp-Lys)-NH$_2$ | 19* |

-continued

| No. | Structure | Amino Acid Sequence | MC4-R Ki (nM) |
|---|---|---|---|
| 35 | 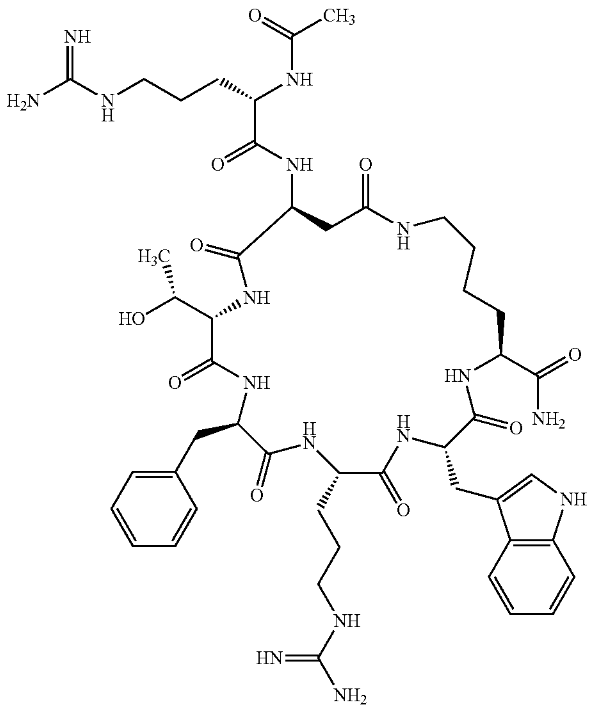 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H]([C@@H](C)O)NC1=O] | Ac-Arg-cyclo(Asp-Thr-D-Phe-Arg-Trp-Lys)-NH$_2$ | 140* |
| 36 | 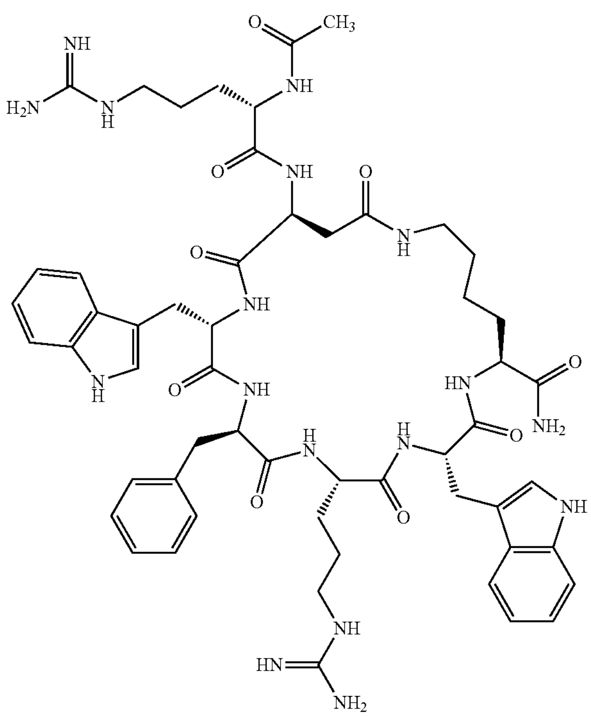 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]c3ccccc23)NC1=O] | Ac-Arg-cyclo(Asp-Trp-D-Phe-Arg-Trp-Lys)-NH$_2$ | 37* |

| No. | Structure | Amino Acid Sequence | MC4-R Ki (nM) |
|---|---|---|---|
| 37 | 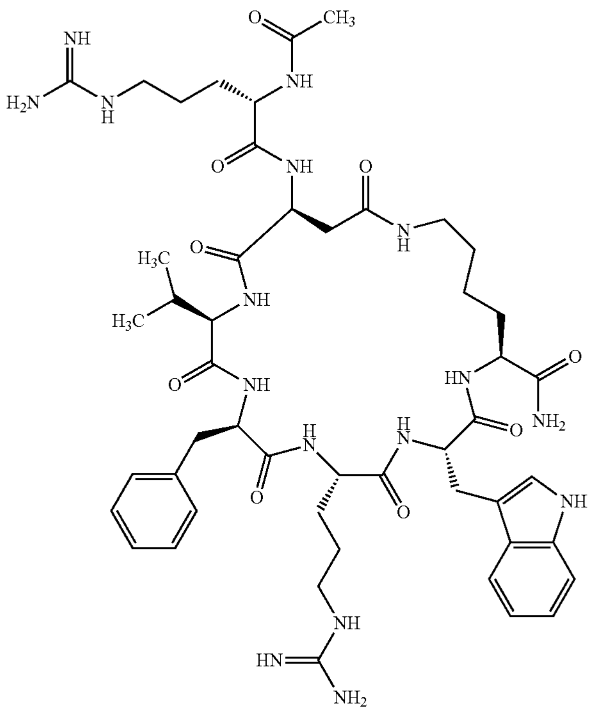 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H](C(C)C)NC1=O] | Ac-Arg-cyclo(Asp-D-Val-D-Phe-Arg-Trp-Lys)-NH$_2$ | ND |
| 38 | 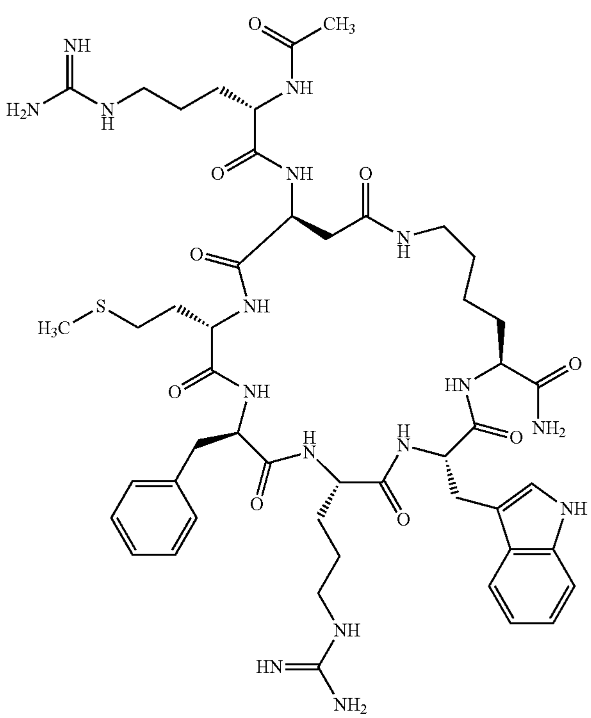 [SMILES: CSCC[C@@H]1NC(=O)[C@@H](NC(=O)[C@H](CCCNC(=N)N)NC(C)=O)CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC1=O] | Ac-Arg-cyclo(Asp-Met-D-Phe-Arg-Trp-Lys)-NH$_2$ | 35* |

| No. | Structure | Amino Acid Sequence | MC4-R Ki (nM) |
|---|---|---|---|
| 39 | 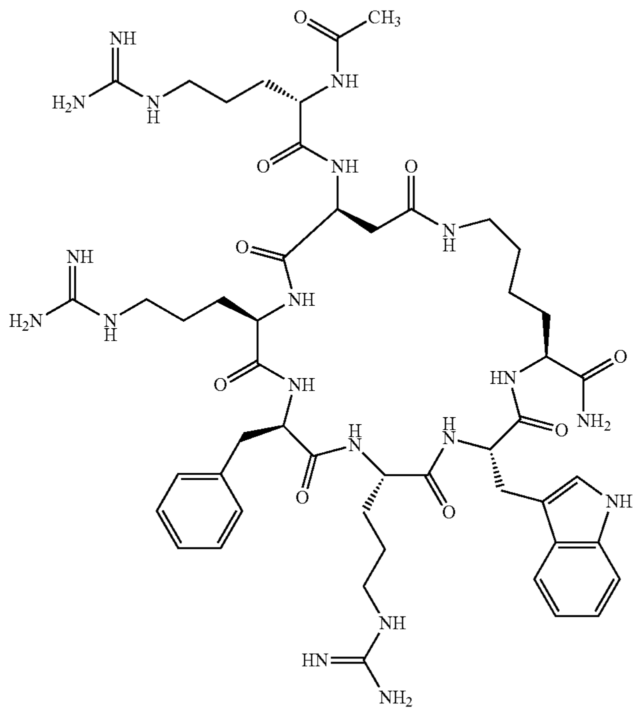 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H](CCCNC(=N)N)NC1=O] | Ac-Arg-cyclo(Asp-D-Arg-D-Phe-Arg-Trp-Lys)-NH$_2$ | ND |
| 40 | 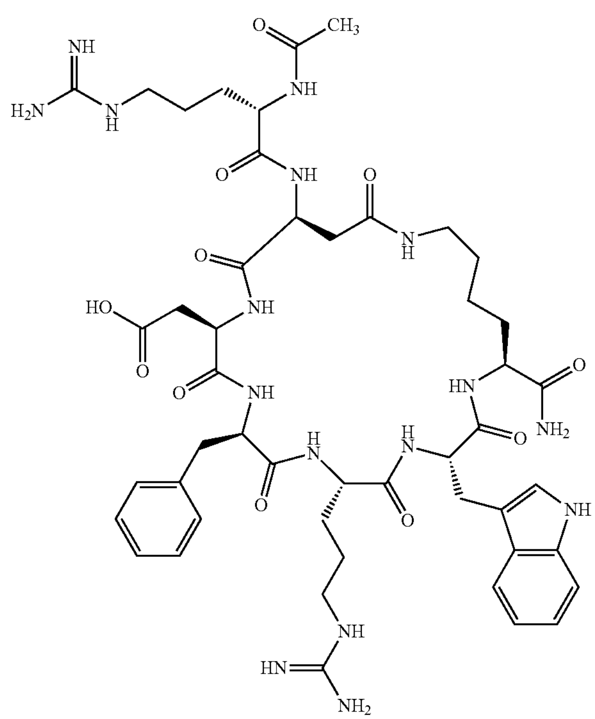 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H](CC(=O)O)NC1=O] | Ac-Arg-cyclo(Asp-D-Asp-D-Phe-Arg-Trp-Lys)-NH$_2$ | ND |

-continued

| No. | Structure | Amino Acid Sequence | MC4-R Ki (nM) |
|---|---|---|---|
| 41 | 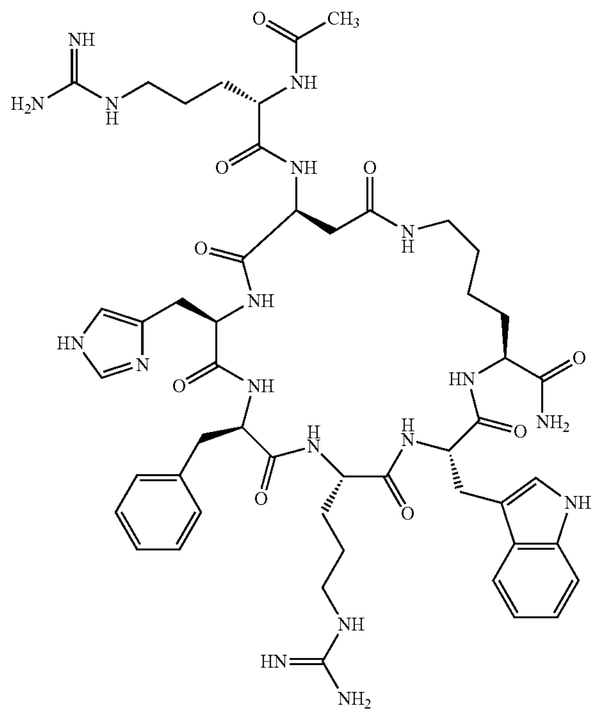 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H](Cc2c[nH]cn2)NC1=O] | Ac-Arg-cyclo(Asp-D-His-D-Phe-Arg-Trp-Lys)-NH$_2$ | 95* |
| 42 | 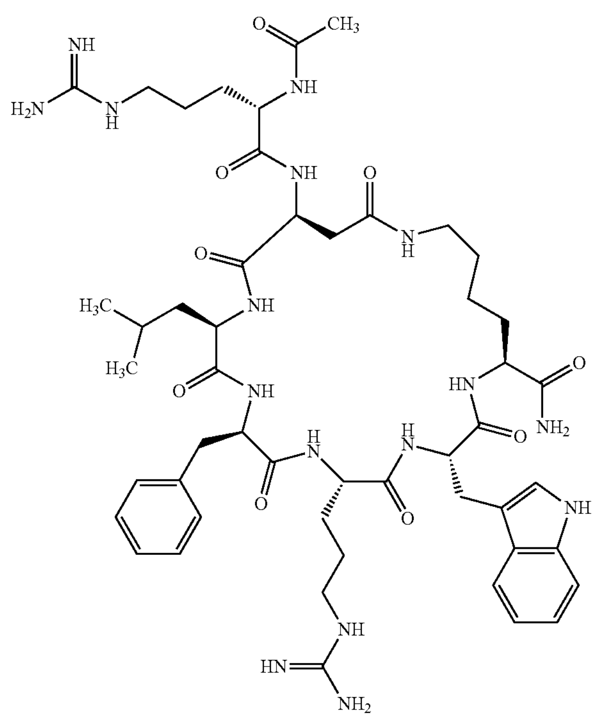 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H](CC(C)C)NC1=O] | Ac-Arg-cyclo(Asp-D-Leu-D-Phe-Arg-Trp-Lys)-NH$_2$ | ND |

| No. | Structure | Amino Acid Sequence | MC4-R Ki (nM) |
|---|---|---|---|
| 43 | 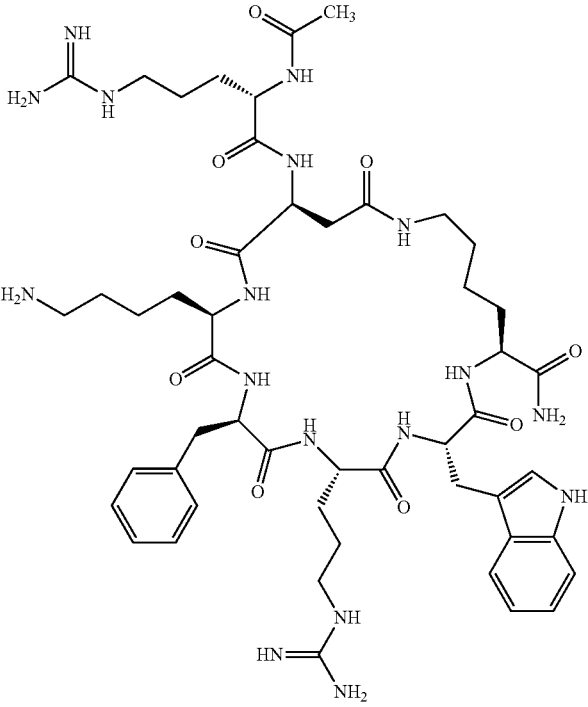 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H](CCCCN)NC1=O] | Ac-Arg-cyclo(Asp-D-Lys-D-Phe-Arg-Trp-Lys)-NH$_2$ | ND |
| 44 | 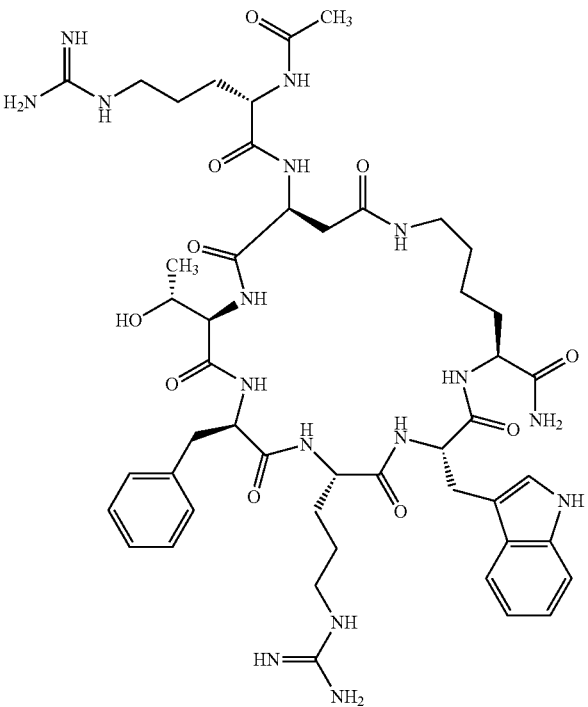 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]([C@@H](C)O)NC1=O] | Ac-Arg-cyclo(Asp-D-Thr-D-Phe-Arg-Trp-Lys)-NH$_2$ | ND |

| No. | Structure | Amino Acid Sequence | MC4-R Ki (nM) |
|-----|-----------|---------------------|---------------|
| 45  | 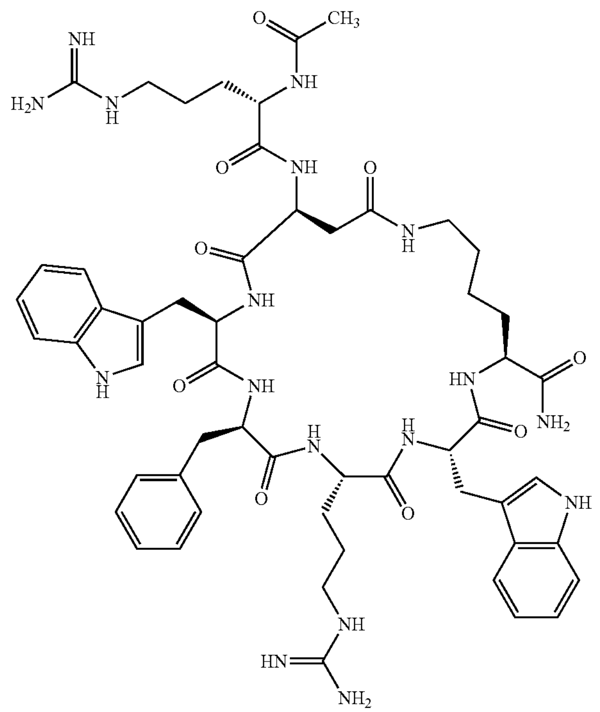 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H](Cc2c[nH]c3ccccc23)NC1=O]          | Ac-Arg-cyclo(Asp-D-Trp-D-Phe-Arg-Trp-Lys)-NH$_2$ | ND |
| 46  | 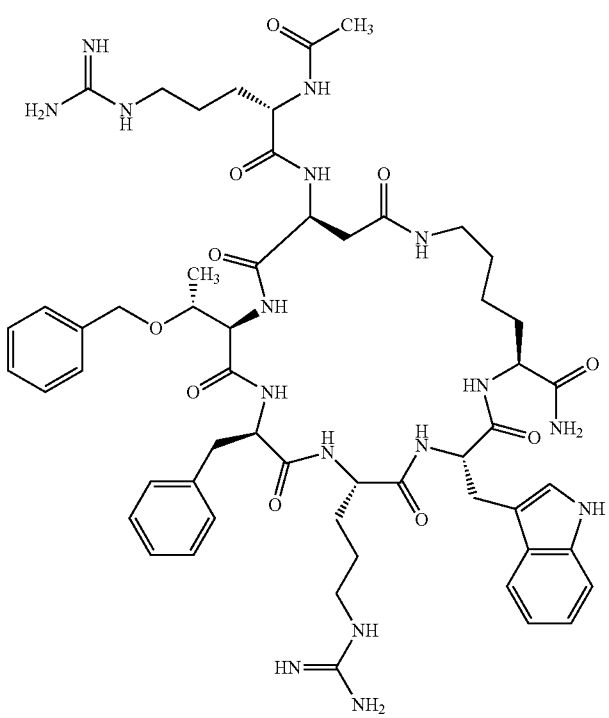 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]([C@@H](C)OCc2ccccc2)NC1=O]          | Ac-Arg-cyclo(Asp-D-Thr(Bzl)-D-Phe-Arg-Trp-Lys)-NH$_2$ | ND |

| No. | Structure | Amino Acid Sequence | MC4-R Ki (nM) |
|---|---|---|---|
| 47 | 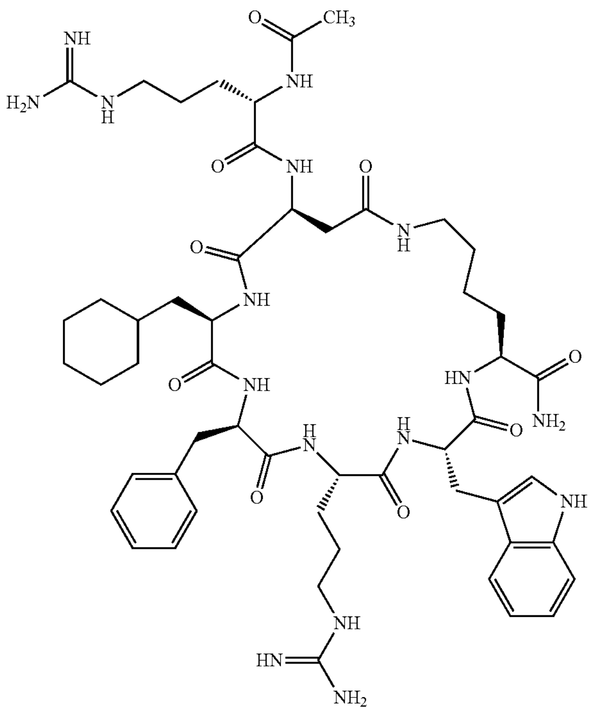 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H](CC2CCCCC2)NC1=O] | Ac-Arg-cyclo(Asp-D-Cha-D-Phe-Arg-Trp-Lys)-NH$_2$ | ND |
| 48 | 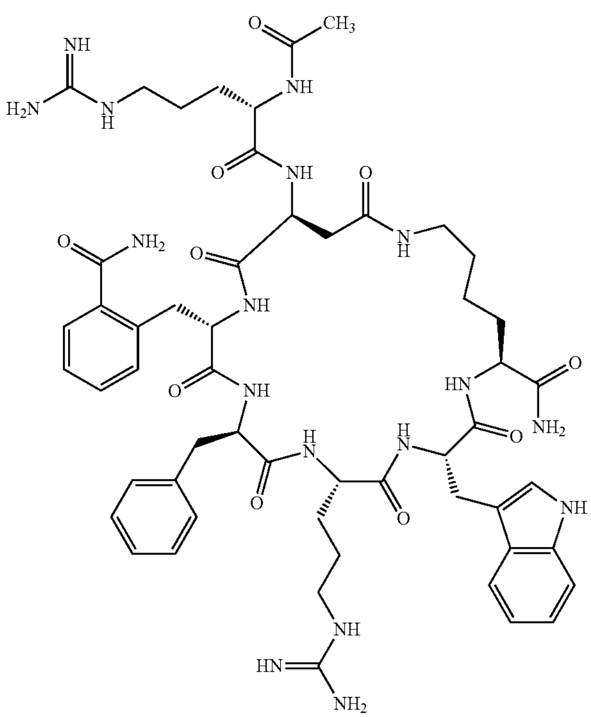 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2ccccc2C(N)=O)NC1=O] | Ac-Arg-cyclo(Asp-Phe(2-C(=O)—NH$_1$)-D-Phe-Arg-Trp-Lys)-NH$_2$ | 23 |

| No. | Structure | Amino Acid Sequence | MC4-R Ki (nM) |
|---|---|---|---|
| 49 | 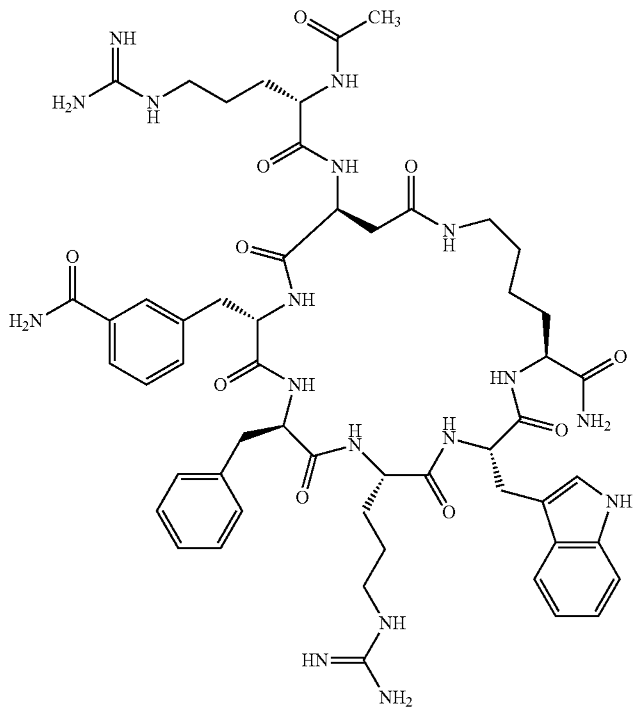 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2cccc(C(N)=O)c2)NC1=O] | Ac-Arg-cyclo(Asp-Phe-(3-(C(=O)—NH₂))-D-Phe-Arg-Trp-Lys)-NH₂ | 15 |
| 50 | 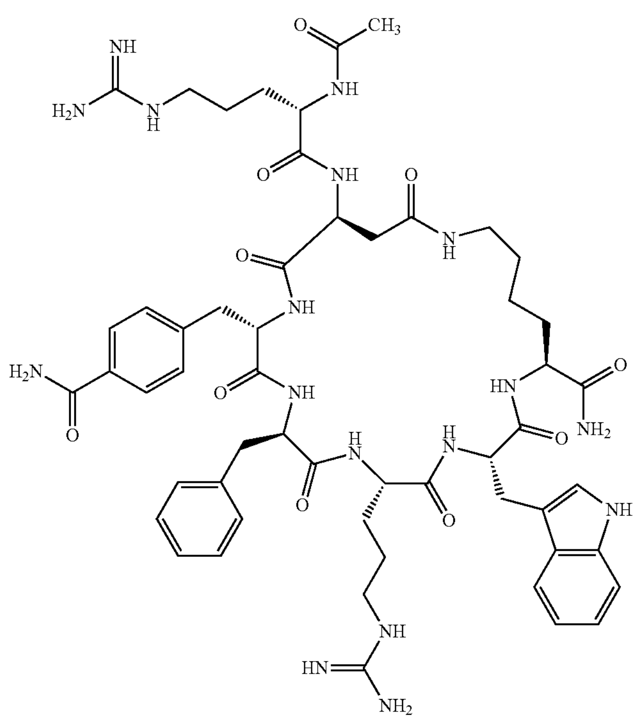 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2ccc(C(N)=O)cc2)NC1=O] | Ac-Arg-cyclo(Asp-Phe(4-(C(=O)—NH₂))-D-Phe-Arg-Trp-Lys)-NH₂ | 30 |

| No. | Structure | Amino Acid Sequence | MC4-R Ki (nM) |
|---|---|---|---|
| 51 | 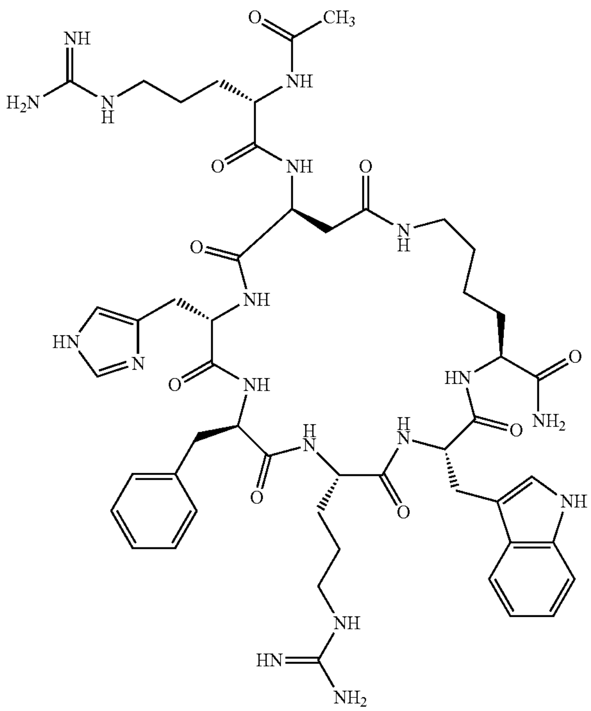 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-cyclo(Asp-His-D-Phe-Arg-Trp-Lys)-OH | 22* |
| 52 | 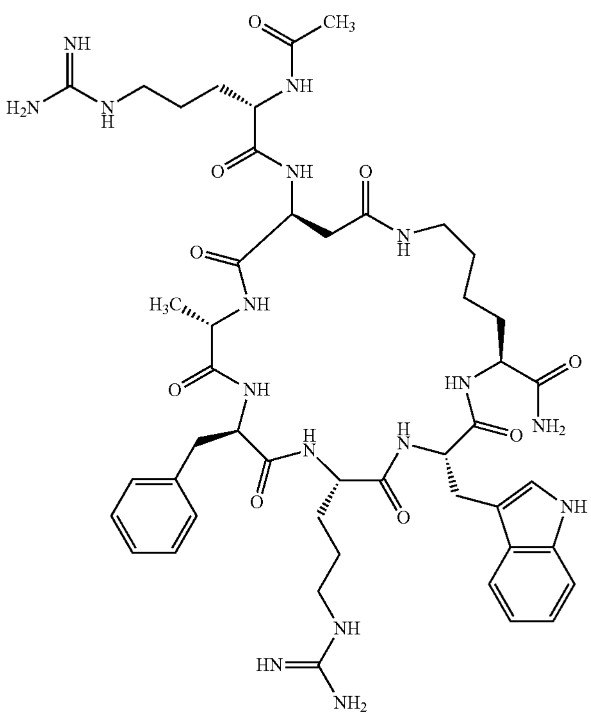 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](C)NC1=O] | Ac-Arg-cyclo(Asp-Ala-D-Phe-Arg-Trp-Lys)-OH | 144* |

| No. | Structure | Amino Acid Sequence | MC4-R Ki (nM) |
|---|---|---|---|
| 53 | 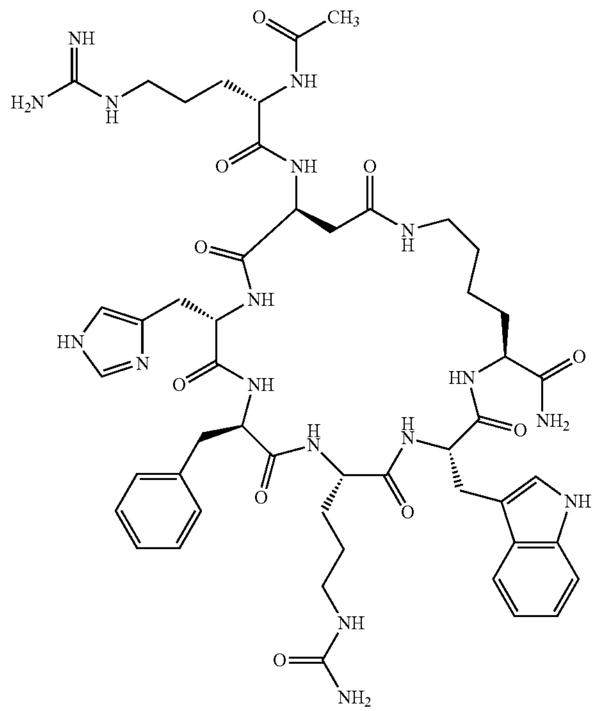 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(N)=O)NC(=O)[C@@H](Cc2ccccc2)NC(=O)[C@H](Cc2c[nH]cn2)NC1=O] | Ac-Arg-cyclo(Asp-His-D-Phe-Cit-Trp-Lys)-OH | 214* |
| 54 | 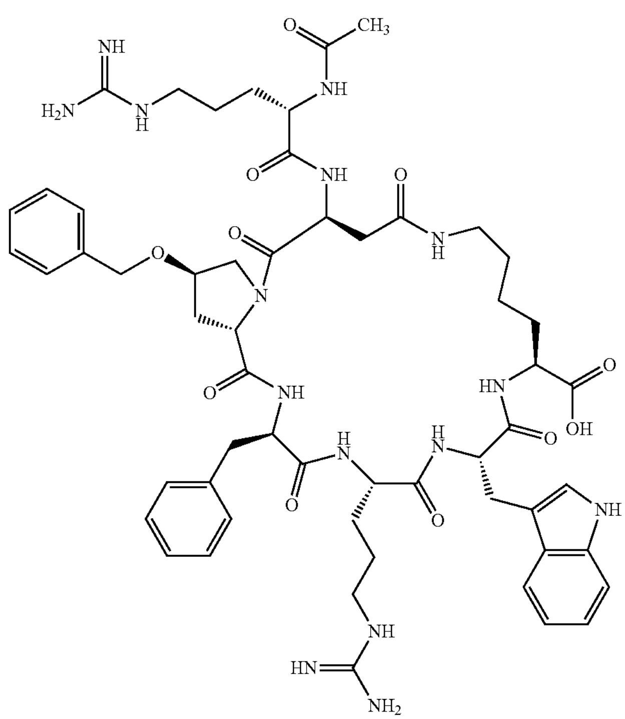 [SMILES: CC(=O)N[C@@H](CCCNC(=N)N)C(=O)N[C@H]1CC(=O)NCCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@@H]2C[C@@H](OCc3ccccc3)CN2C1=O] | Ac-Arg-cyclo(Asp-Hyp(Bzl)-D-Phe-Arg-Trp-Lys)-OH | 3 |

-continued

| No. | Structure | Amino Acid Sequence | MC4-R Ki (nM) |
|---|---|---|---|
| 55 | 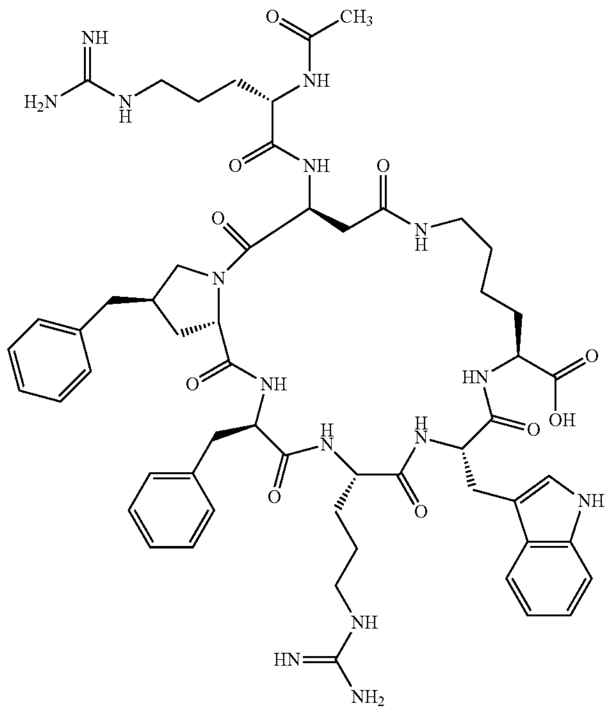 [SMILES: CC(=O)N[C@@H](CCCNC(=N)N)C(=O)N[C@H]1CC(=O)NCCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@@H]2C[C@@H](Cc3ccccc3)CN2C1=O] | Ac-Arg-cyclo(Asp-Pro(Bn)-D-Phe-Arg-Trp-Lys)-OH | 12 |
| 56 | 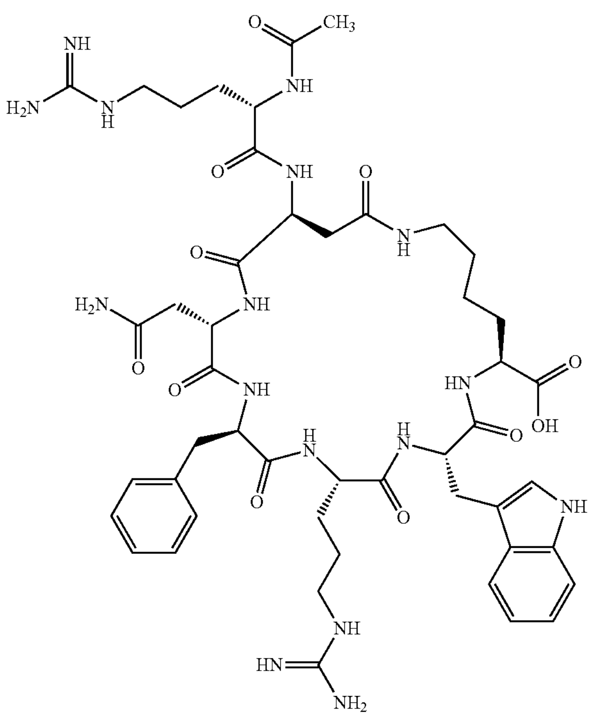 [SMILES: CC(=O)N[C@@H](CCCNC(=N)N)C(=O)N[C@H]1CC(=O)NCCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O] | Ac-Arg-cyclo(Asp-Asn-D-Phe-Arg-Trp-Lys)-OH | 100 |

| No. | Structure | Amino Acid Sequence | MC4-R Ki (nM) |
|---|---|---|---|
| 57 | 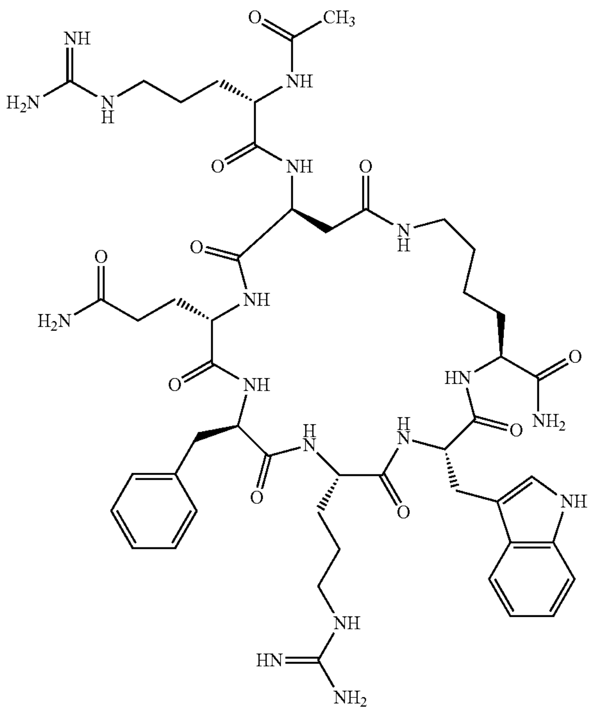 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-Arg-cyclo(Asp-Gln-D-Phe-Arg-Trp-Lys)-OH | 115 |
| 58 | 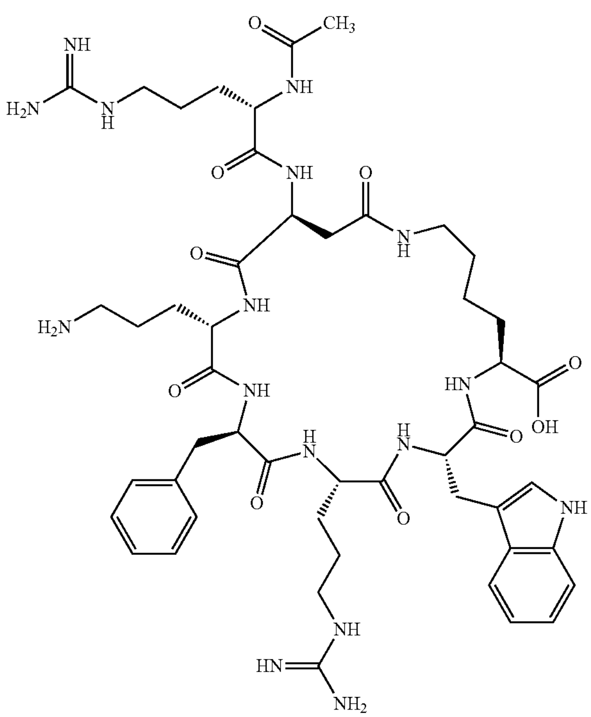 [SMILES: CC(=O)N[C@@H](CCCNC(=N)N)C(=O)N[C@H]1CC(=O)NCCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCCN)NC1=O] | Ac-Arg-cyclo(Asp-Orn-D-Phe-Arg-Trp-Lys)-OH | 23 |

| No. | Structure | Amino Acid Sequence | MC4-R Ki (nM) |
|---|---|---|---|
| 59 | 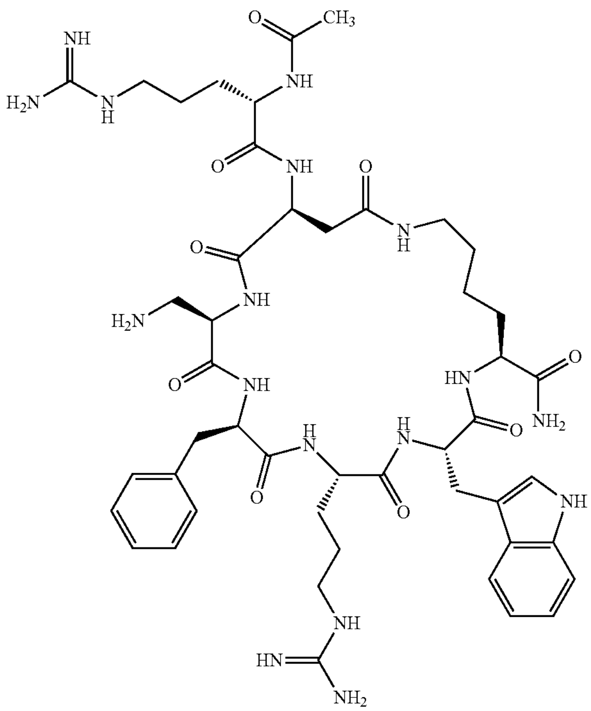 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H](CN)NC1=O] | Ac-Arg-cyclo(Asp-Dap-D-Phe-Arg-Trp-Lys)-NH$_2$ | ND |
| 60 | 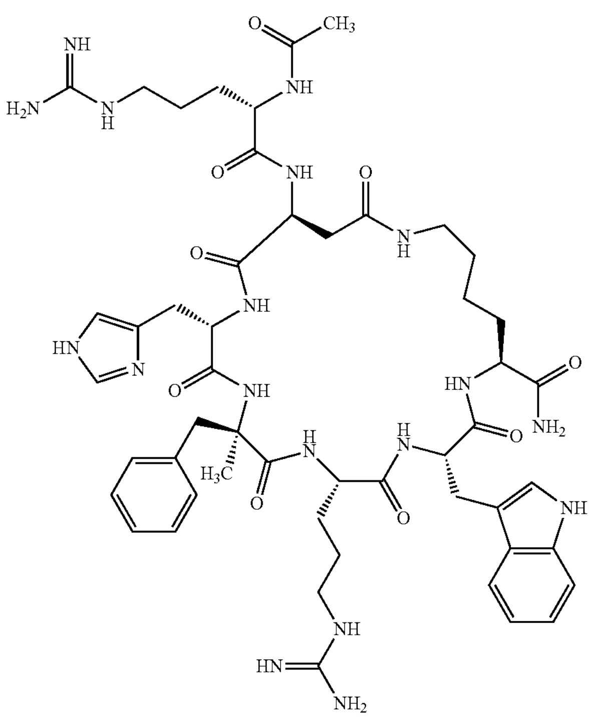 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@](C)(Cc2ccccc2)NC(=O)[C@H](Cc2c[nH]cn2)NC1=O] | Ac-Arg-cyclo(Asp-His-D-(alpha-Me)Phe-Arg-Trp-Lys)-NH$_2$ | 47* |

-continued

| No. | Structure | Amino Acid Sequence | MC4-R Ki (nM) |
|---|---|---|---|
| 61 | 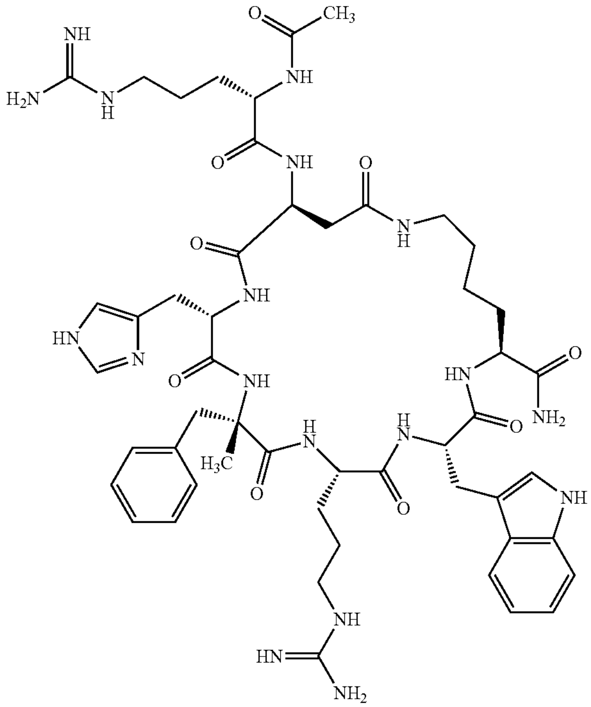 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@](C)(Cc2ccccc2)NC(=O)[C@H](Cc2c[nH]cn2)NC1=O] | Ac-Arg-cyclo(Asp-His-(alpha-Me)-Phe-Arg-Trp-Lys)-NH₂ | ND |
| 62 | 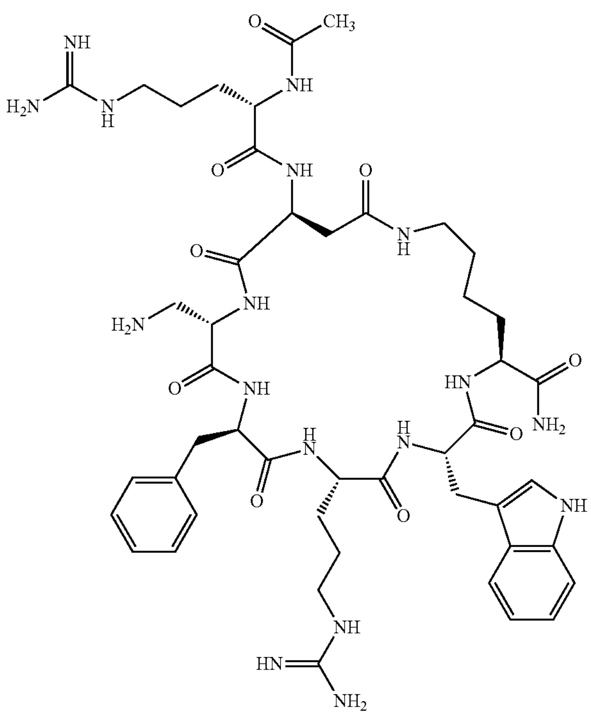 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CN)NC1=O] | Ac-Arg-cyclo(Asp-Dap-D-Phe-Arg-Trp-Lys)-NH₂ | 80* |

-continued

| No. | Structure | Amino Acid Sequence | MC4-R Ki (nM) |
|---|---|---|---|
| 63 | 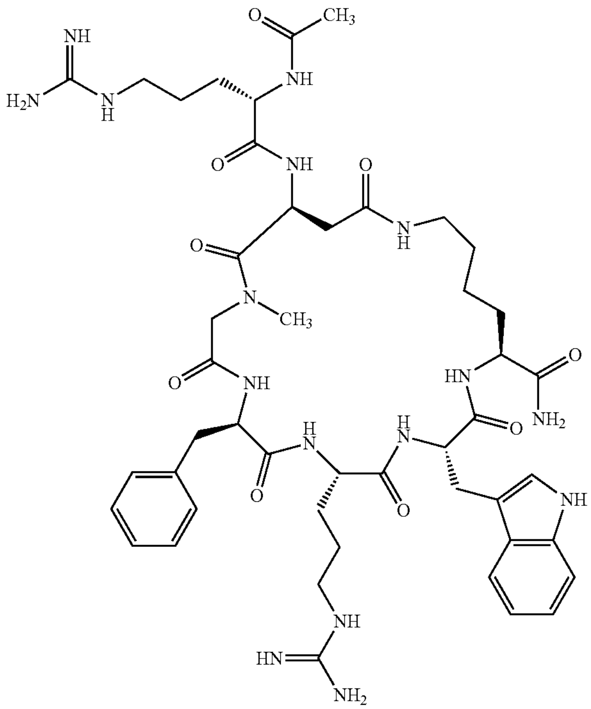 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)CN(C)C1=O] | Ac-Arg-cyclo(Asp-Sar-D-Phe-Arg-Trp-Lys)-NH₂ | 15 |
| 64 | 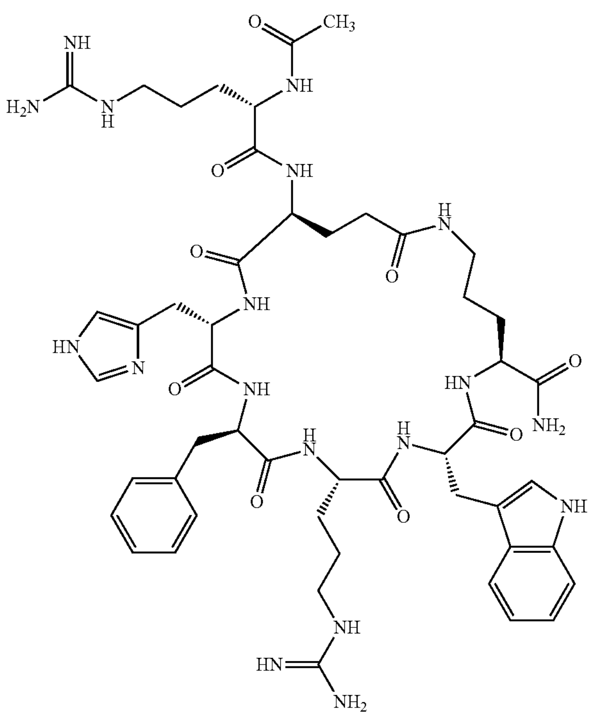 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-cyclo(Glu-His-D-Phe-Arg-Trp-Orn)-NH₂ | 1* |

| No. | Structure | Amino Acid Sequence | MC4-R Ki (nM) |
|---|---|---|---|
| 65 | 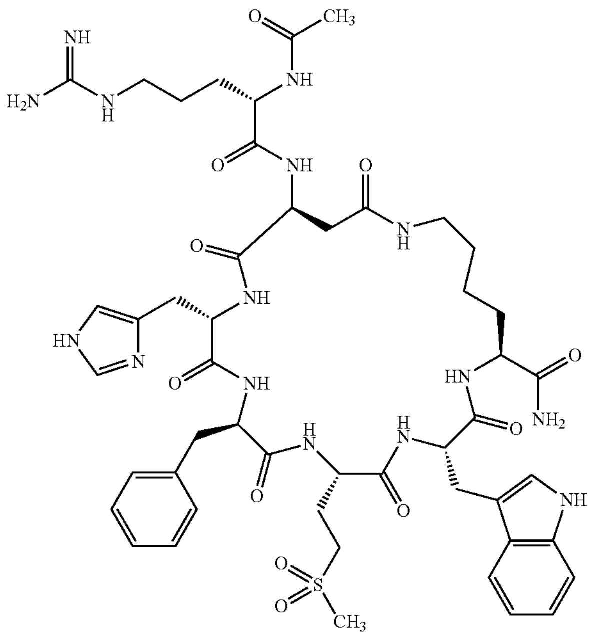 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCS(C)(=O)=O)NC(=O)[C@@H](Cc2ccccc2)NC(=O)[C@H](Cc2c[nH]cn2)NC1=O] | Ac-Arg-cyclo(Asp-His-D-Phe-Met(O$_2$)-Trp-Lys)-NH$_2$ | ND |
| 66 | 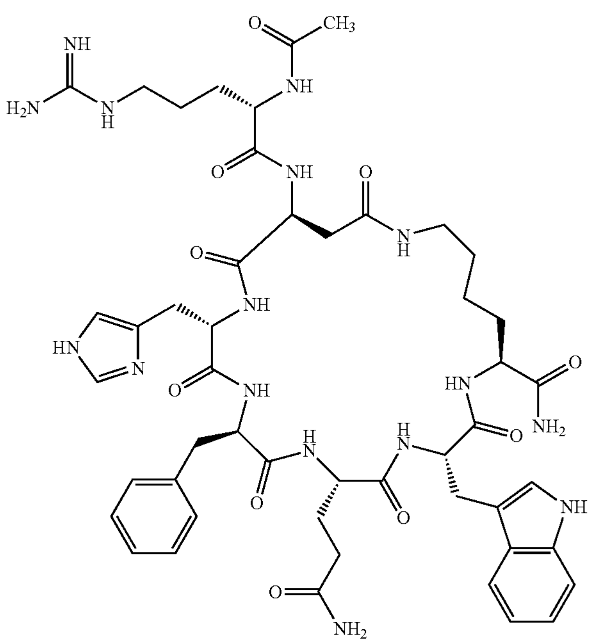 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCC(N)=O)NC(=O)[C@@H](Cc2ccccc2)NC(=O)[C@H](Cc2c[nH]cn2)NC1=O] | Ac-Arg-cyclo(Asp-His-D-Phe-Gln-Trp-Lys)-NH$_2$ | ND |

| No. | Structure | Amino Acid Sequence | MC4-R Ki (nM) |
|---|---|---|---|
| 67 | 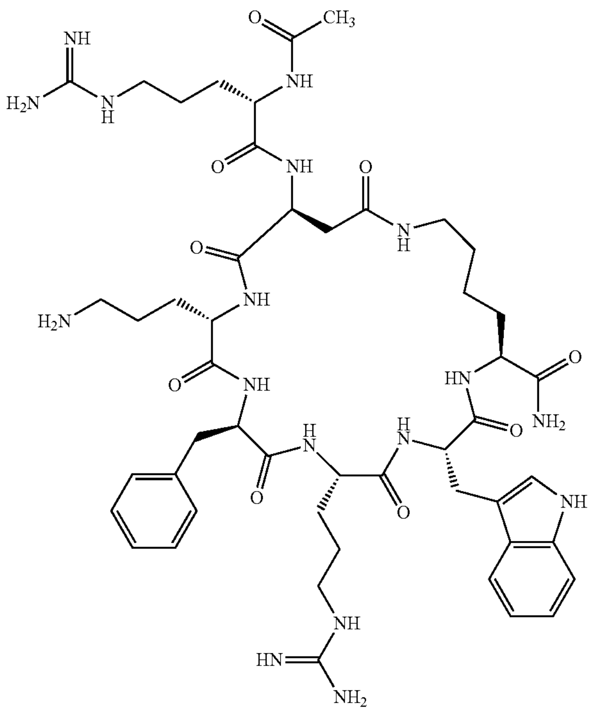 | Ac-Arg-cyclo(Asp-Orn-D-Phe-Arg-Trp-Lys)-NH$_2$ | 7* |
| 68 | 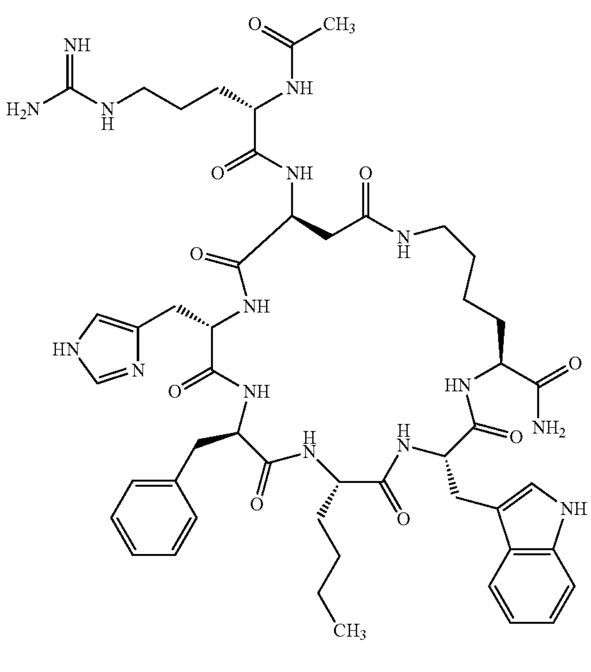 [SMILES: CCCC[C@@H]1NC(=O)[C@@H](Cc2ccccc2)NC(=O)[C@H](Cc2c[nH]cn2)NC(=O)[C@@H](NC(=O)[C@H](CCCNC(=N)N)NC(C)=O)CC(=O)NCCCC[C@@H](C(N)=O)NC(=O)[C@H](Cc2c[nH]c3ccccc23)NC1=O] | Ac-Arg-cyclo(Asp-His-D-Phe-D-Nle-Trp-Lys)-NH$_2$ | ND |

| No. | Structure | Amino Acid Sequence | MC4-R Ki (nM) |
|---|---|---|---|
| 69 | 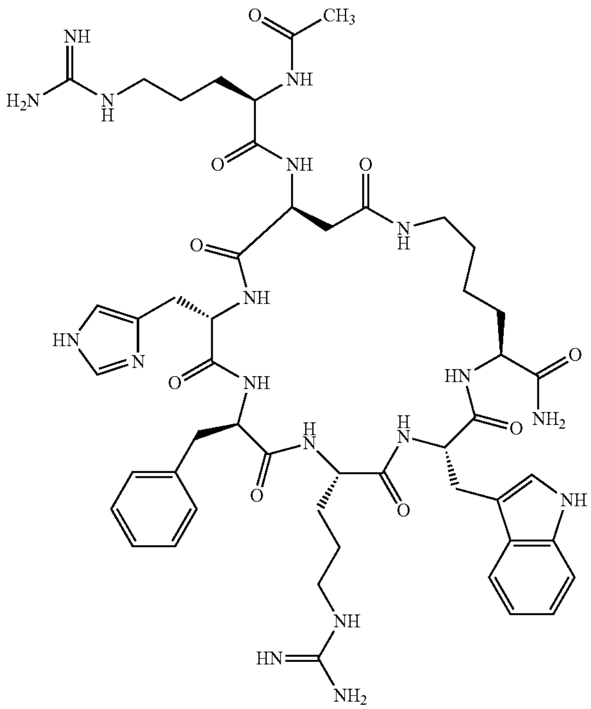 [SMILES: CC(=O)N[C@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-D-Arg-cyclo(Asp-His-D-Phe-Arg-Trp-Lys)-NH₂ | 8* |
| 70 | 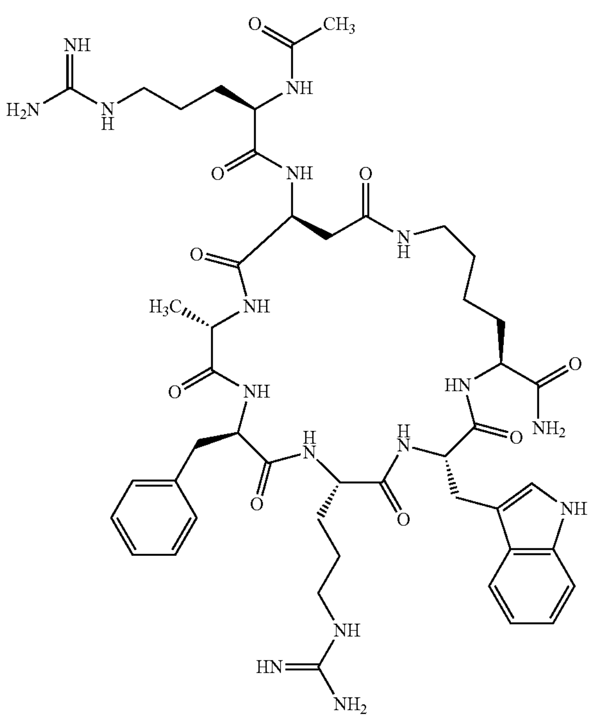 [SMILES: CC(=O)N[C@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](C)NC1=O] | Ac-D-Arg-cyclo(Asp-Ala-D-Phe-Arg-Trp-Lys)-NH₂ | 46* |

| No. | Structure | Amino Acid Sequence | MC4-R Ki (nM) |
|---|---|---|---|
| 71 | 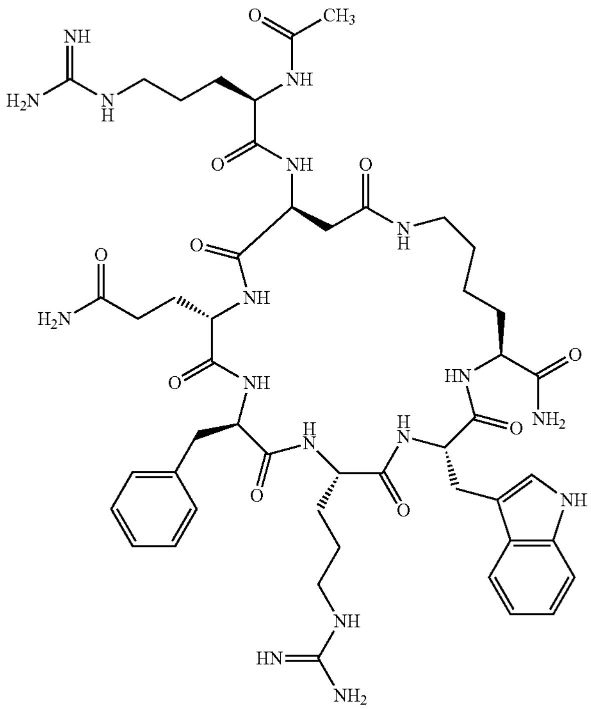 [SMILES: CC(=O)N[C@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-D-Arg-cyclo(Asp-Gln-D-Phe-Arg-Trp-Lys)-NH$_2$ | 45 |
| 72 | 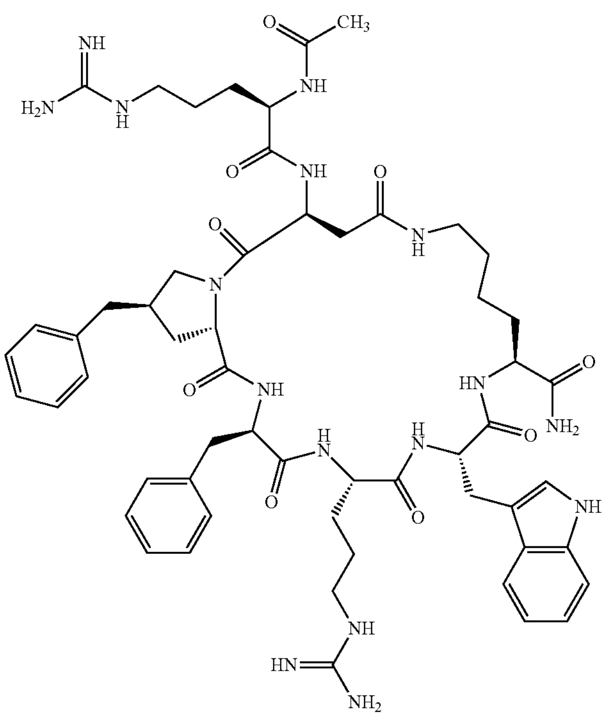 [SMILES: CC(=O)N[C@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]2C[C@@H](Cc3ccccc3)CN2C1=O] | Ac-D-Arg-cyclo(Asp-Pro(4R-Bzl)-D-Phe-Arg-Trp-Lys)-NH$_2$ | 2* |

-continued

| No. | Structure | Amino Acid Sequence | MC4-R Ki (nM) |
|---|---|---|---|
| 73 | 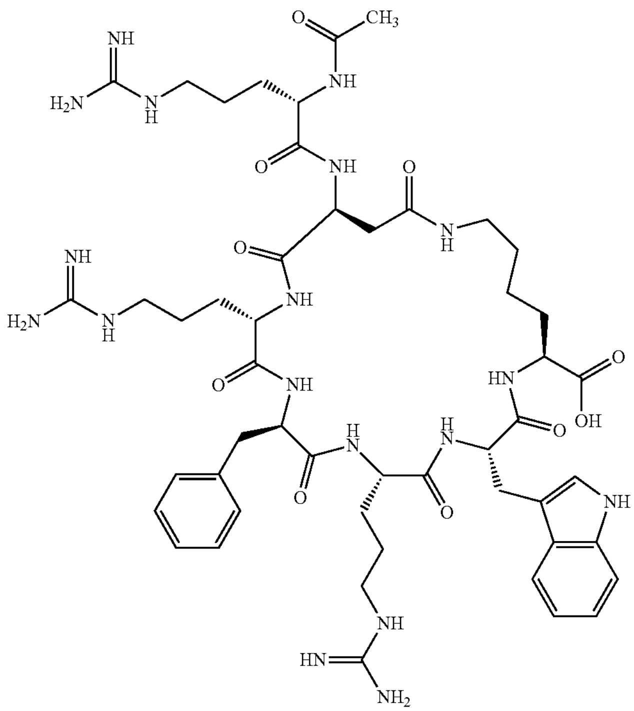 | Ac-Arg-cyclo(Asp-Arg-D-Phe-Arg-Trp-Lys)-OH | 60* |
| 74 | 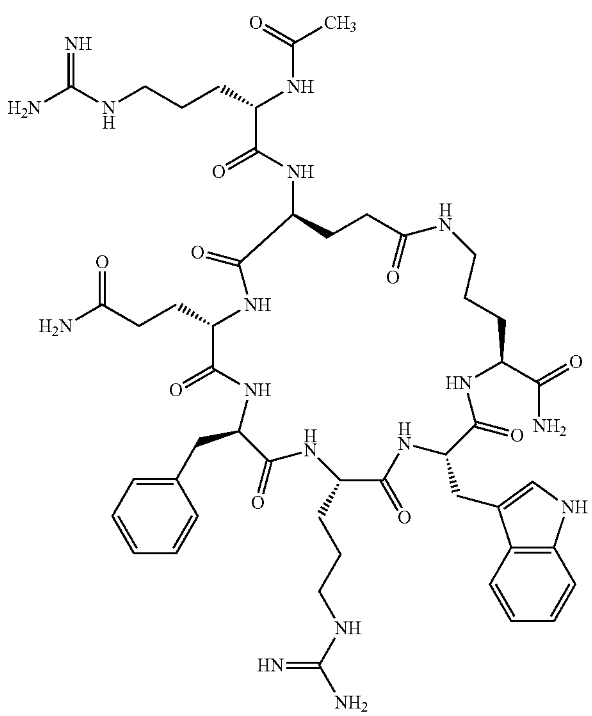 | Ac-Arg-cyclo(Glu-Gln-D-Phe-Arg-Trp-Orn)-NH₂ | 3 |

-continued

| No. | Structure | Amino Acid Sequence | MC4-R Ki (nM) |
|---|---|---|---|
| 75 | 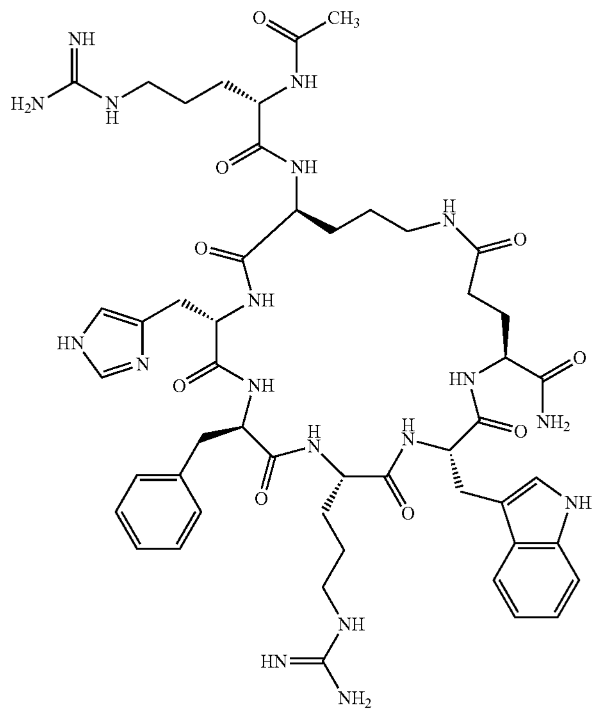 | Ac-Arg-cyclo(Orn-His-D-Phe-Arg-Trp-Glu)-NH₂ | 0.6 |
| 76 | 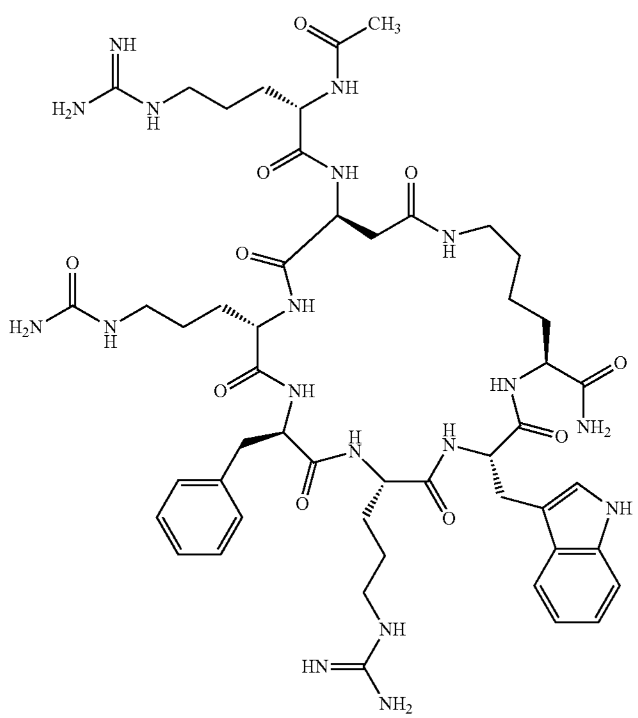 | Ac-Arg-cyclo(Asp-Arg-D-Phe-Arg-Trp-Lys)-NH₂ | 14 |

| No. | Structure | Amino Acid Sequence | MC4-R Ki (nM) |
|---|---|---|---|
| 77 | 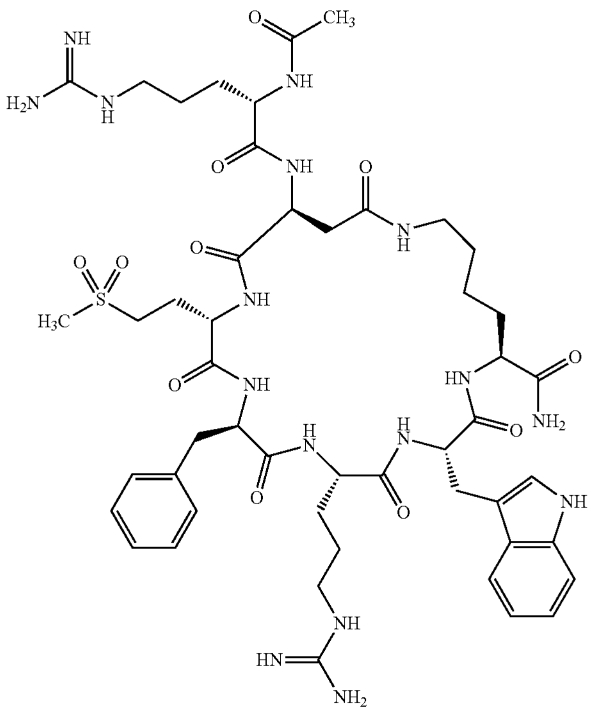 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCS(C)(=O)=O)NC1=O] | Ac-Arg-cyclo(Asp-Met-(O₂)-D-Phe-Arg-Trp-Lys)-NH₂ | 7 |
| 78 | 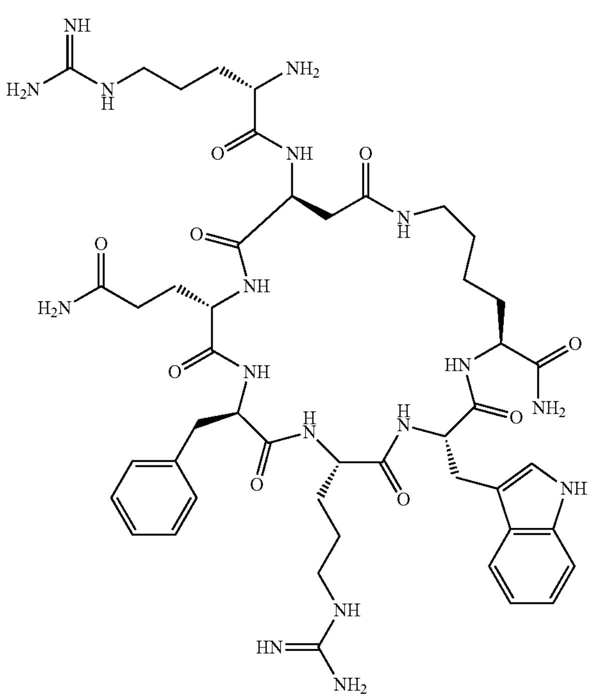 [SMILES: N=C(N)NCCC[C@@H]1NC(=O)[C@@H](Cc2ccccc2)NC(=O)[C@H](CCC(N)=O)NC(=O)[C@@H](NC(=O)[C@@H](N)CCCNC(=N)N)CC(=O)NCCCC[C@@H](C(N)=O)NC(=O)[C@H](Cc2c[nH]c3ccccc23)NC1=O] | Ac-Arg-cyclo(Asp-Gln-D-Phe-Arg-Trp-Lys)-NH₂ | 86* |

| No. | Structure | Amino Acid Sequence | MC4-R Ki (nM) |
|---|---|---|---|
| 79 | 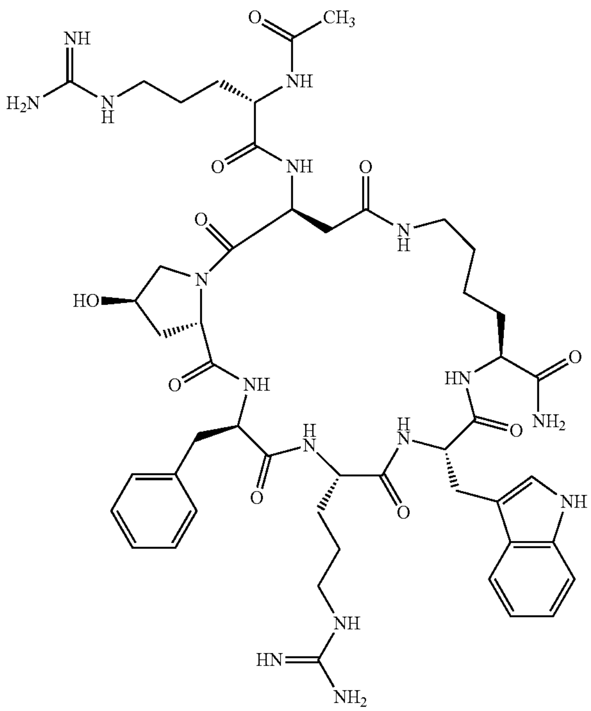 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]2C[C@@H](O)CN2C1=O] | Ac-Arg-cyclo(Asp-Hyp-D-Phe-Arg-Trp-Lys)-NH₂ | 4 |
| 80 | 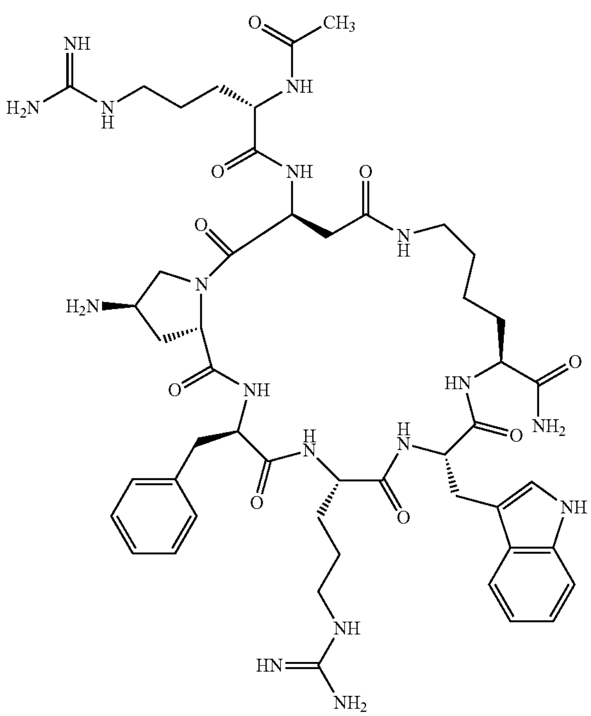 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]2C[C@@H](N)CN2C1=O] | Ac-Arg-cyclo(Asp-Pro(4R-NH₂)-D-Phe-Arg-Trp-Lys)-NH₂ | 5 |

-continued

| No. | Structure | Amino Acid Sequence | MC4-R Ki (nM) |
|---|---|---|---|
| 81 | 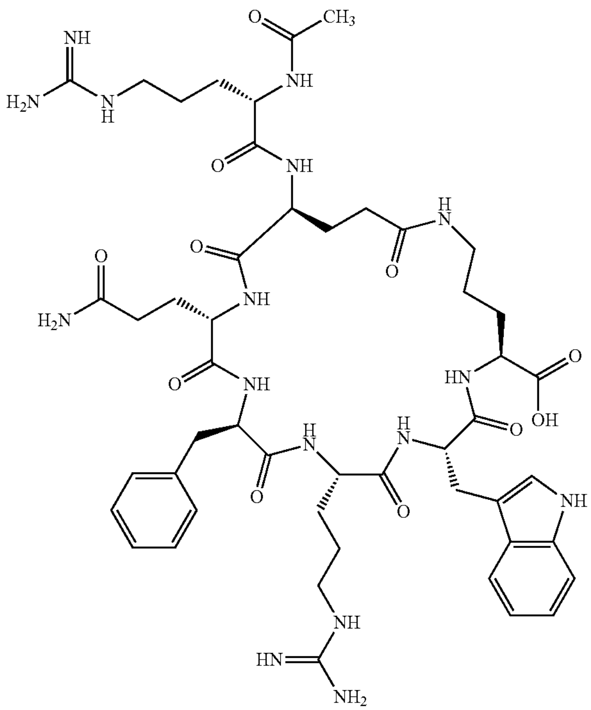 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-Arg-cyclo(Glu-Gln-D-Phe-Arg-Trp-Orn)-OH | 43 |
| 82 | 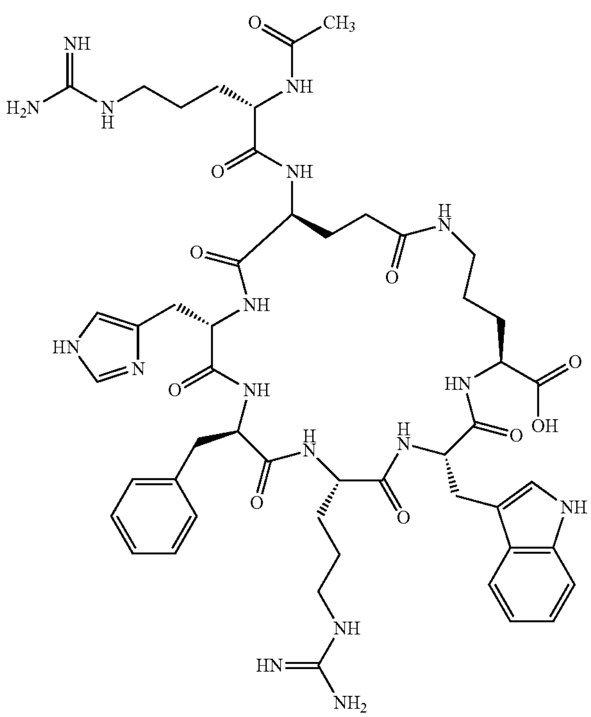 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-cyclo(Glu-His-D-Phe-Arg-Trp-Orn)-OH | 4 |

-continued

| No. | Structure | Amino Acid Sequence | MC4-R Ki (nM) |
|---|---|---|---|
| 83 | 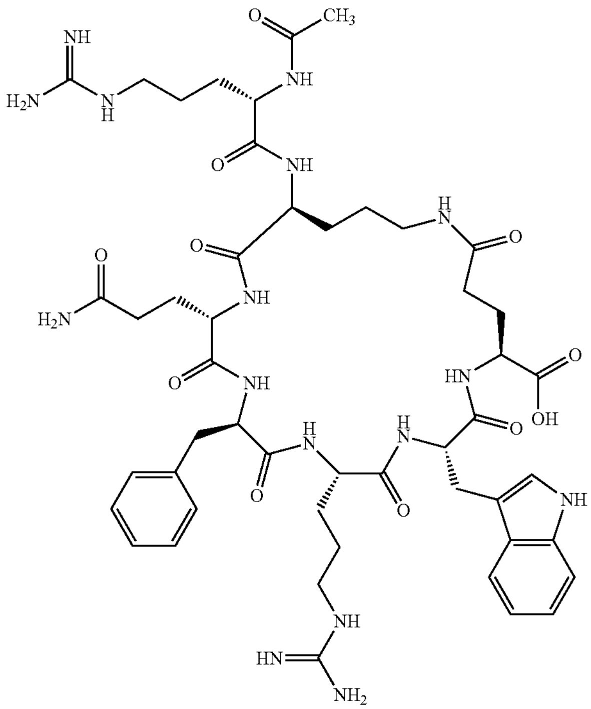 | Ac-Arg-cyclo(Orn-Gln-D-Phe-Arg-Trp-Glu)-OH | ND |
| 84 | 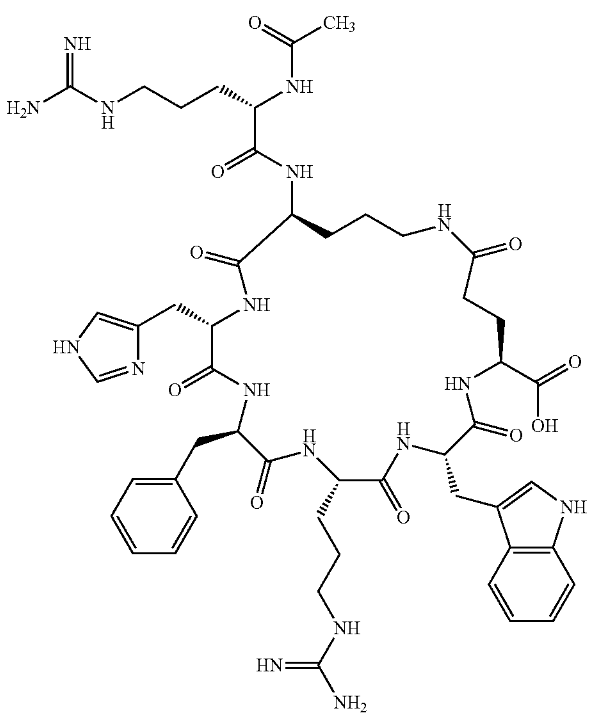 [SMILES: CC(=O)N[C@@H](CCCNC(=N)N)C(=O)N[C@H]1CCCNC(=O)CC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-cyclo(Orn-His-D-Phe-Arg-Trp-Glu)-OH | 12* |

| No. | Structure | Amino Acid Sequence | MC4-R Ki (nM) |
|---|---|---|---|
| 85 | 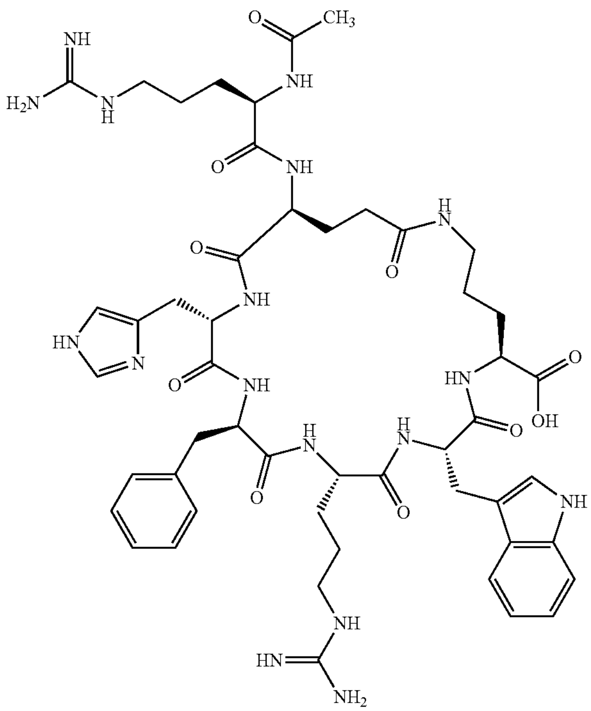 [SMILES: CC(=O)N[C@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-D-Arg-cyclo(Glu-His-D-Phe-Arg-Trp-Orn)-OH | 40* |
| 86 | 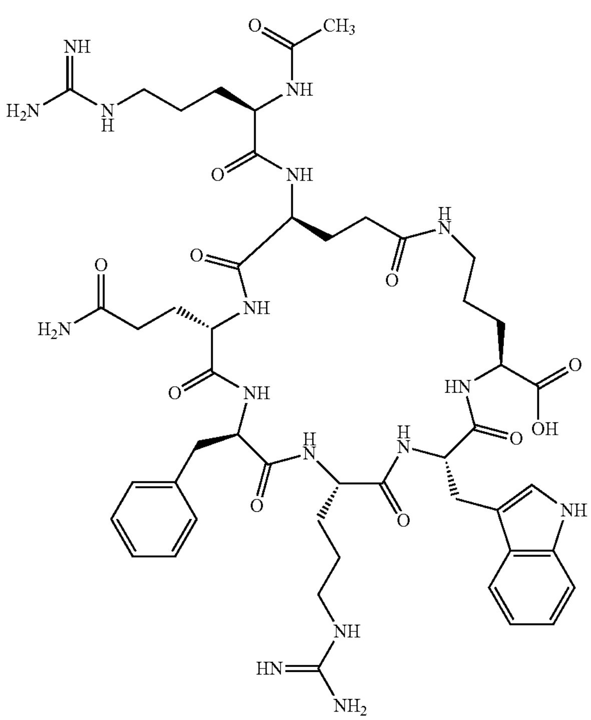 [SMILES: CC(=O)N[C@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-D-Arg-cyclo(Glu-Gln-D-Phe-Arg-Trp-Orn)-OH | 66* |

-continued
| No. | Structure | Amino Acid Sequence | MC4-R Ki (nM) |
|---|---|---|---|
| 87 | 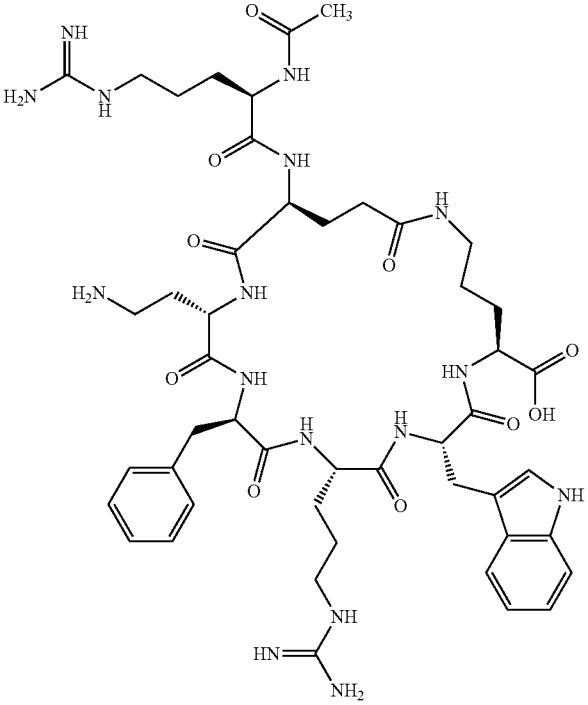 [SMILES: CC(=O)N[C@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-D-Arg-cyclo(Glu-Dab-D-Phe-Arg-Trp-Orn)-OH | 171* |
| 88 | 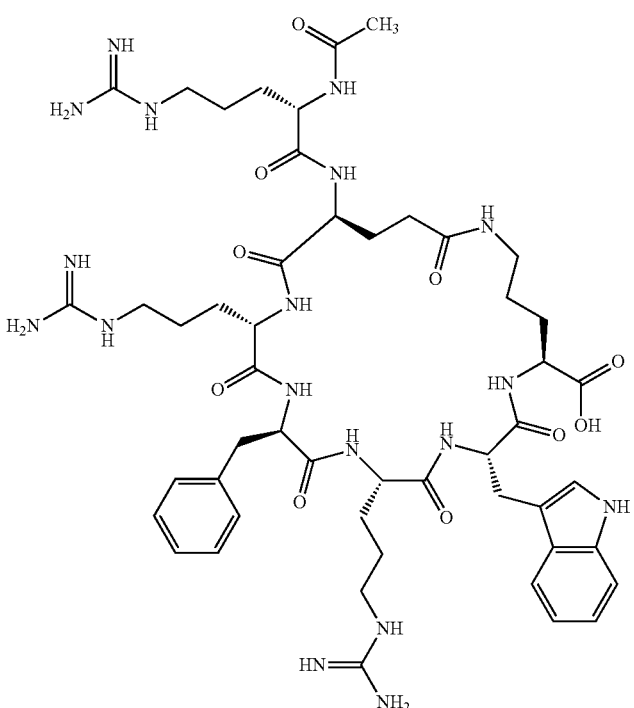 | Ac-Arg-cyclo(Glu-Arg-D-Phe-Arg-Trp-Orn)-OH | 37* |

| No. | Structure | Amino Acid Sequence | MC4-R Ki (nM) |
|---|---|---|---|
| 89 | 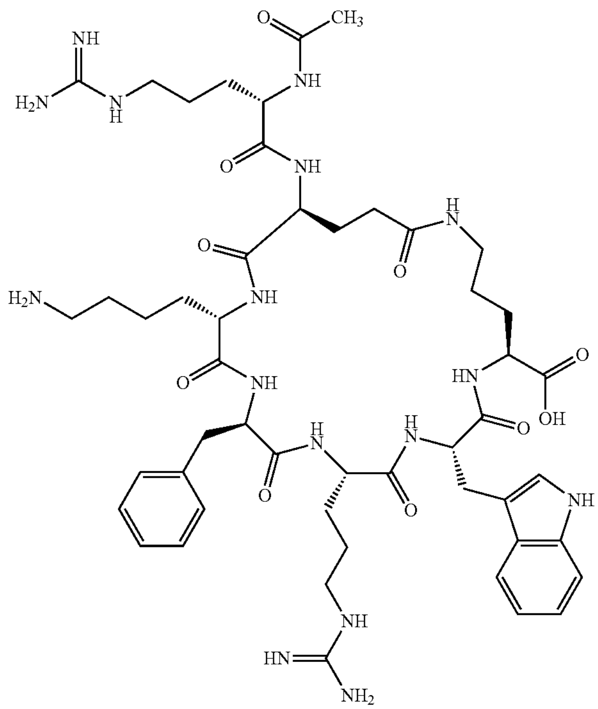 | Ac-Arg-cyclo(Glu-Lys-D-Phe-Arg-Trp-Orn)-OH | 113* |
| 90 | 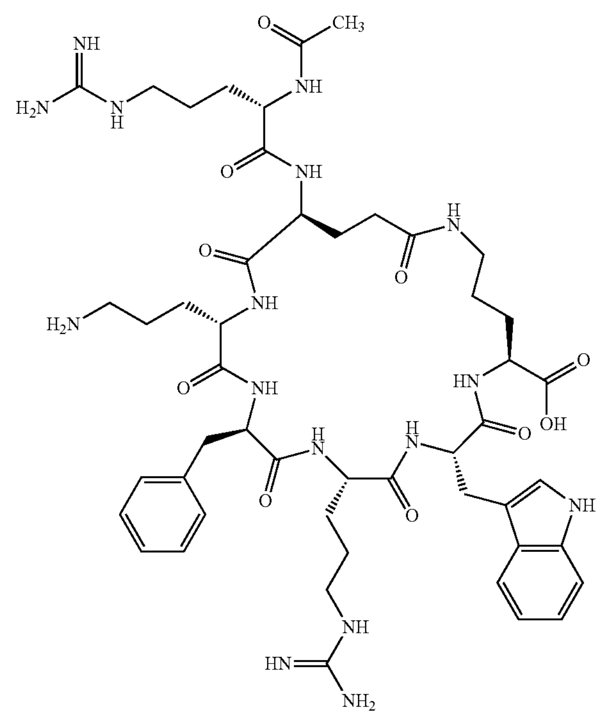 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCCN)NC1=O] | Ac-Arg-cyclo(Glu-Orn-D-Phe-Arg-Trp-Orn)-OH | 9 |

-continued

| No. | Structure | Amino Acid Sequence | MC4-R Ki (nM) |
|---|---|---|---|
| 91 | 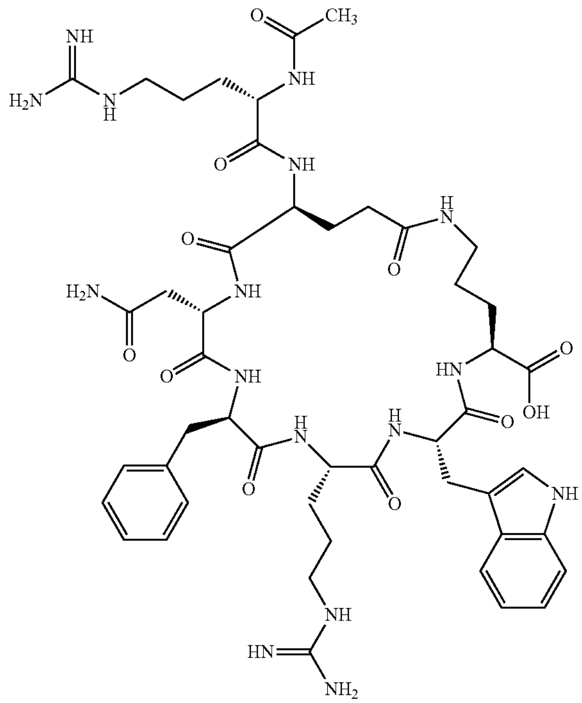 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O] | Ac-Arg-cyclo(Glu-Asn-D-Phe-Arg-Trp-Orn)-OH | 167 |
| 92 | 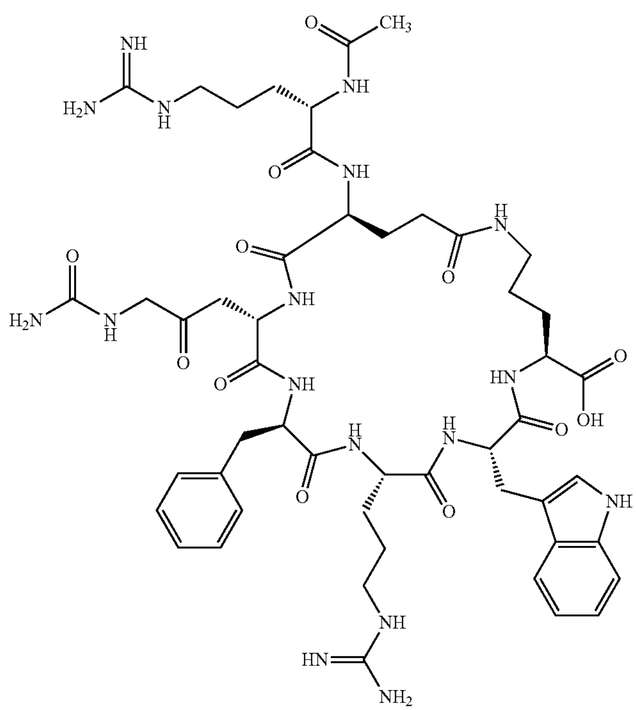 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CC(=O)CNC(N)=O)NC1=O] | Ac-Arg-cyclo(Glu-Cit-D-Phe-Arg-Trp-Orn)-OH | 184* |

-continued

| No. | Structure | Amino Acid Sequence | MC4-R Ki (nM) |
|---|---|---|---|
| 93 | 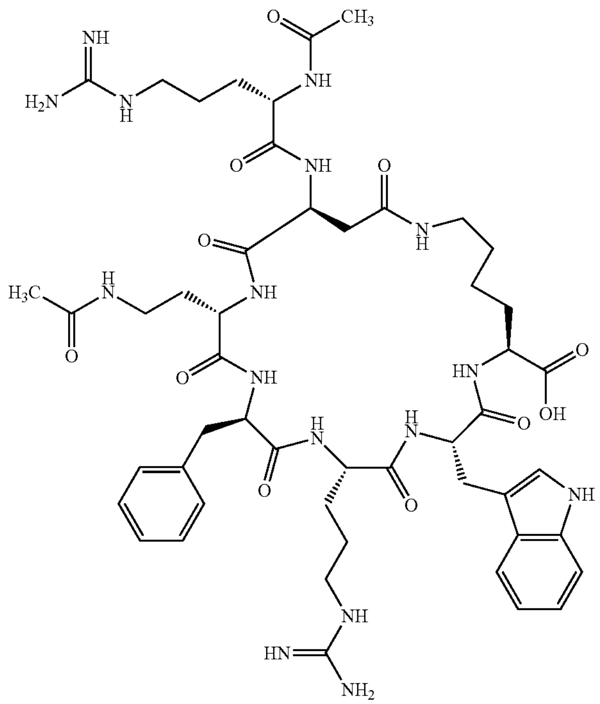 [SMILES: CC(=O)NCC[C@@H]1NC(=O)[C@@H](NC(=O)[C@H](CCCNC(=N)N)NC(C)=O)CC(=O)NCCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC1=O] | Ac-Arg-cyclo(Asp-Dab(Acetyl)-D-Phe-Arg-Trp-Lys)-NH$_2$ | 33 |
| 94 | 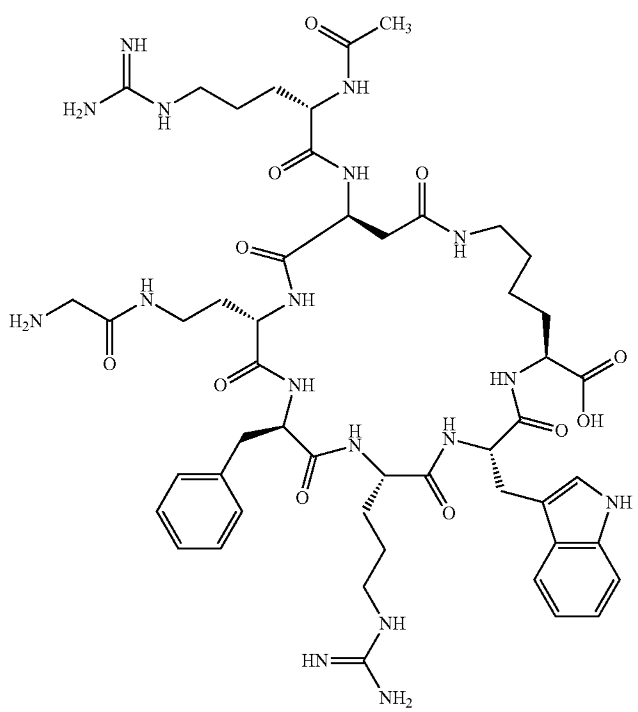 [SMILES: CC(=O)N[C@@H](CCCNC(=N)N)C(=O)N[C@H]1CC(=O)NCCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCNC(=O)CN)NC1=O] | Ac-Arg-cyclo(Asp-Dab(Glycly)-D-Phe-Arg-Trp-Lys)-NH$_2$ | 110* |

| No. | Structure | Amino Acid Sequence | MC4-R Ki (nM) |
|---|---|---|---|
| 95 | 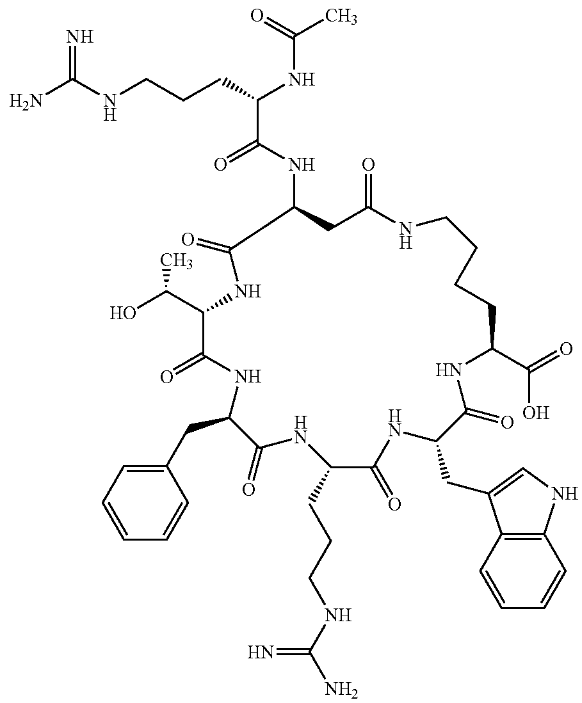 [SMILES: CC(=O)N[C@@H](CCCNC(=N)N)C(=O)N[C@H]1CC(=O)NCCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H]([C@@H](C)O)NC1=O] | Ac-Arg-cyclo(Asp-Thr-D-Phe-Arg-Trp-Lys)-NH2 | ND |
| 96 | 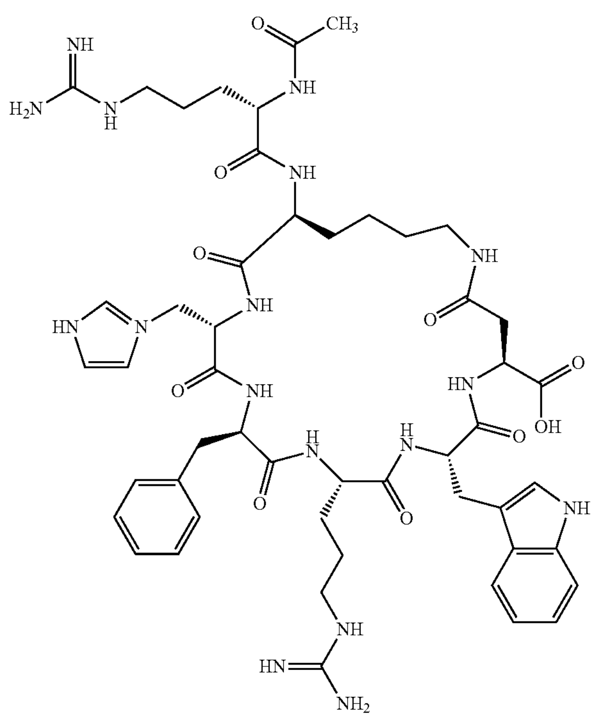 | Ac-Arg-cyclo(Lys-His-D-Phe-Arg-Trp-Asp)-NH2 | 1* |

| No. | Structure | Amino Acid Sequence | MC4-R Ki (nM) |
|---|---|---|---|
| 97 | 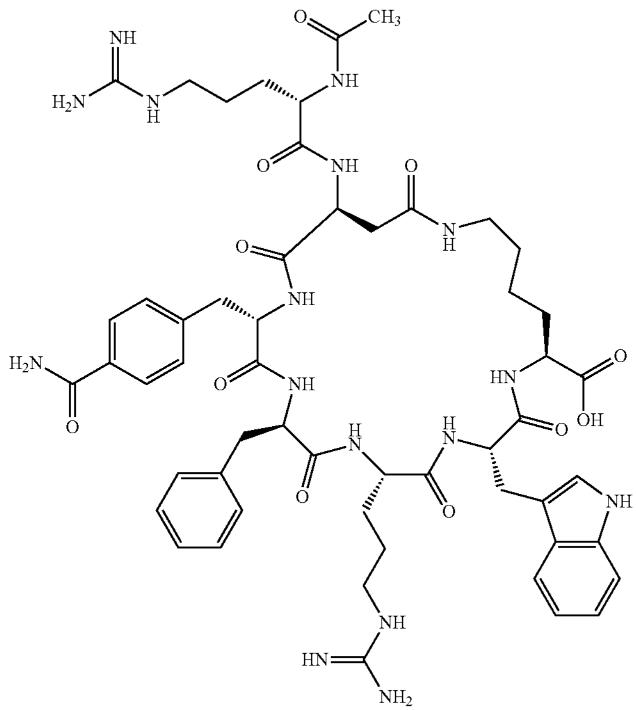 | Ac-Arg-cyclo(Asp-Phe(4-(C(=O)—NH$_2$))-D-Phe-Arg-Trp-Lys)-OH | ND |
| 98 | 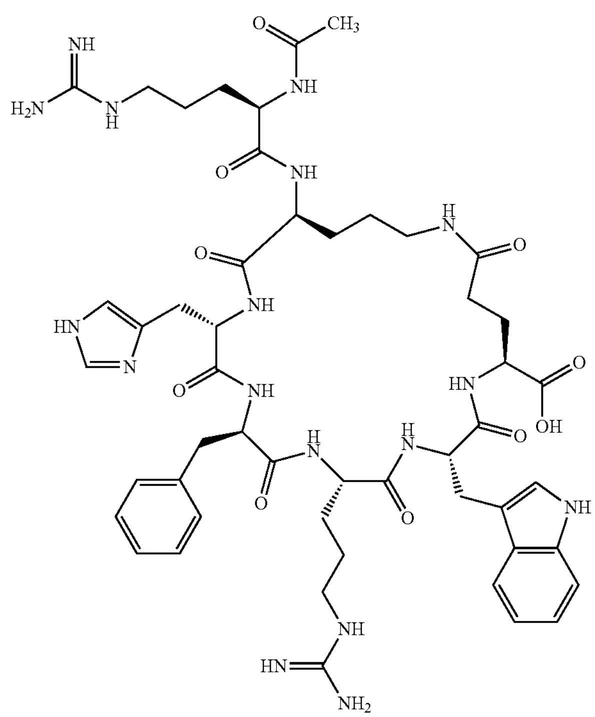 [SMILES: CC(=O)N[C@H](CCCNC(=N)N)C(=O)N[C@H]1CCCNC(=O)CC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-D-Arg-cyclo(Orn-His-D-Phe-Arg-Trp-Glu)-NH$_2$ | 4* |

-continued

| No. | Structure | Amino Acid Sequence | MC4-R Ki (nM) |
|---|---|---|---|
| 99 | 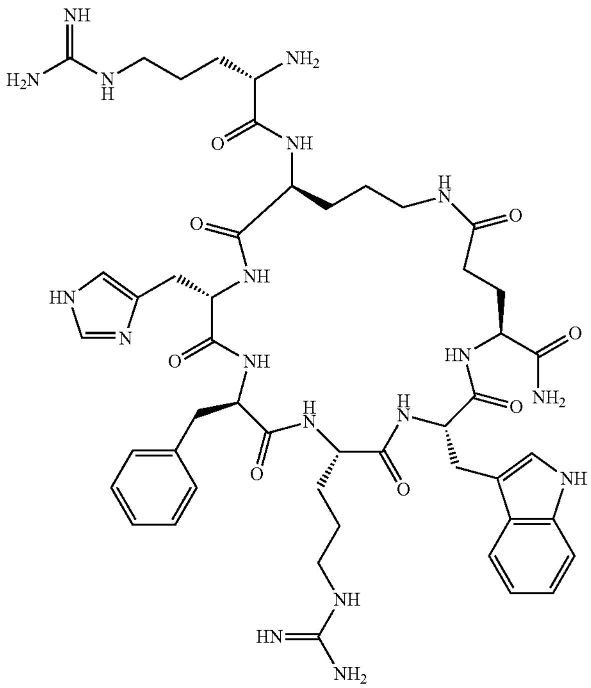 [SMILES: N=C(N)NCCC[C@@H]1NC(=O)[C@@H](Cc2ccccc2)NC(=O)[C@H](Cc2c[nH]cn2)NC(=O)[C@@H](NC(=O)[C@@H](N)CCCNC(=N)N)CCCNC(=O)CC[C@@H](C(N)=O)NC(=O)[C@H](Cc2c[nH]c3ccccc23)NC1=O] | Arg-cyclo(Orn-His-D-Phe-Arg-Trp-Glu)-NH$_2$ | 6 |
| 100 | 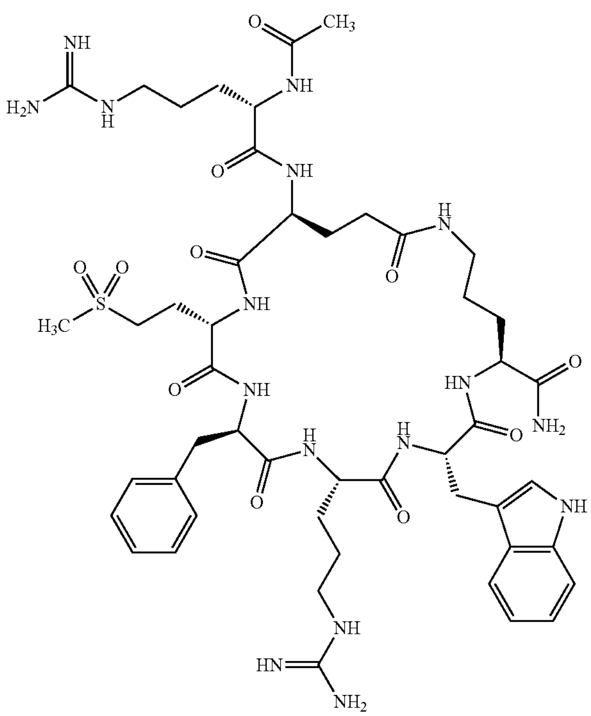 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCS(C)(=O)=O)NC1=O] | Ac-Arg-cyclo(Glu-Met(O$_2$)-D-Phe-Arg-Trp-Orn)-NH$_2$ | 8 |

-continued

| No. | Structure | Amino Acid Sequence | MC4-R Ki (nM) |
|---|---|---|---|
| 101 | 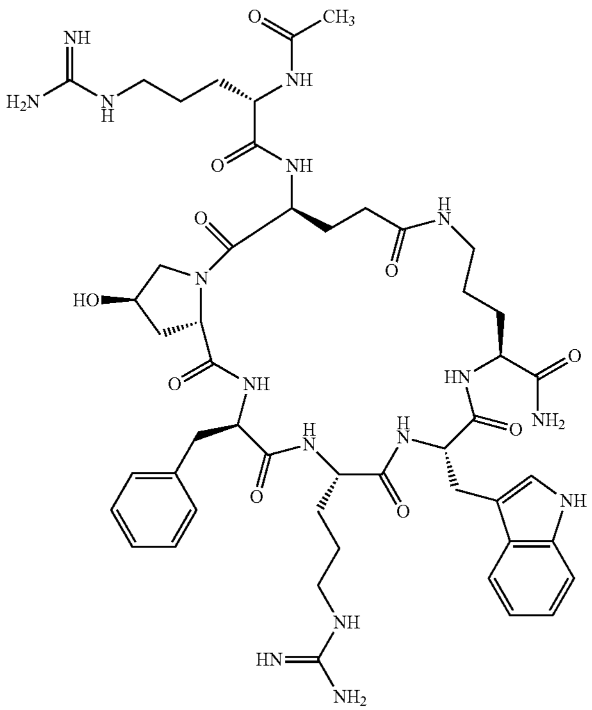 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]2C[C@@H](O)CN2C1=O] | Ac-Arg-cyclo(Glu-Hyp-D-Phe-Arg-Trp-Orn)-NH₂ | 3 |
| 102 | 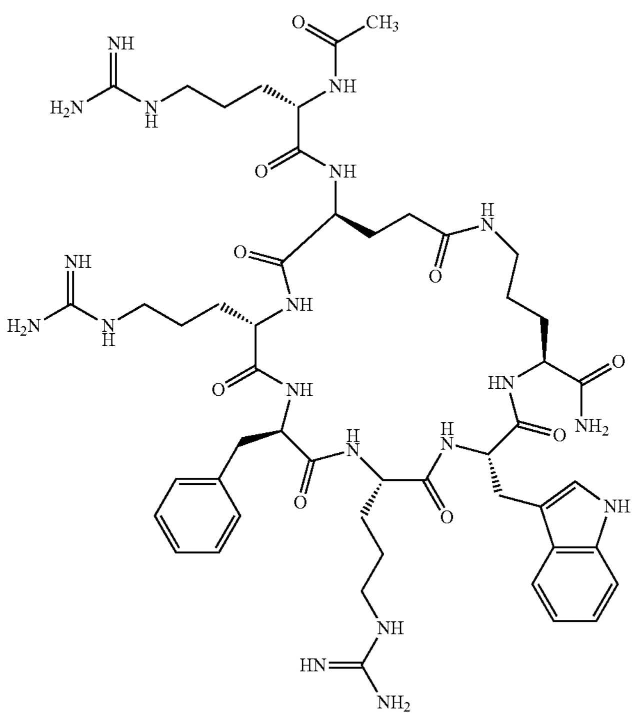 | Ac-Arg-cyclo(Glu-Arg-D-Phe-Arg-Trp-Orn)-NH₂ | 0.7 |

| No. | Structure | Amino Acid Sequence | MC4-R Ki (nM) |
|---|---|---|---|
| 103 | 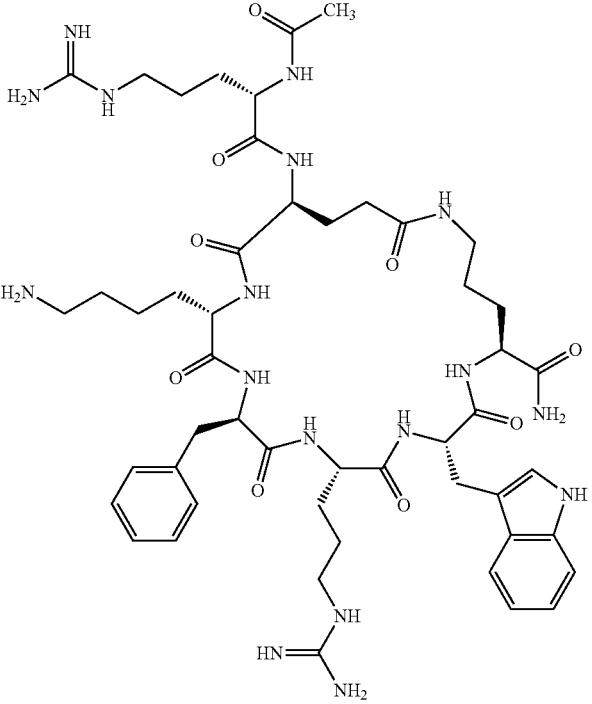 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCCCN)NC1=O] | Ac-Arg-cyclo(Glu-Lys-D-Phe-Arg-Trp-Orn)-NH$_2$ | 15 |
| 104 | 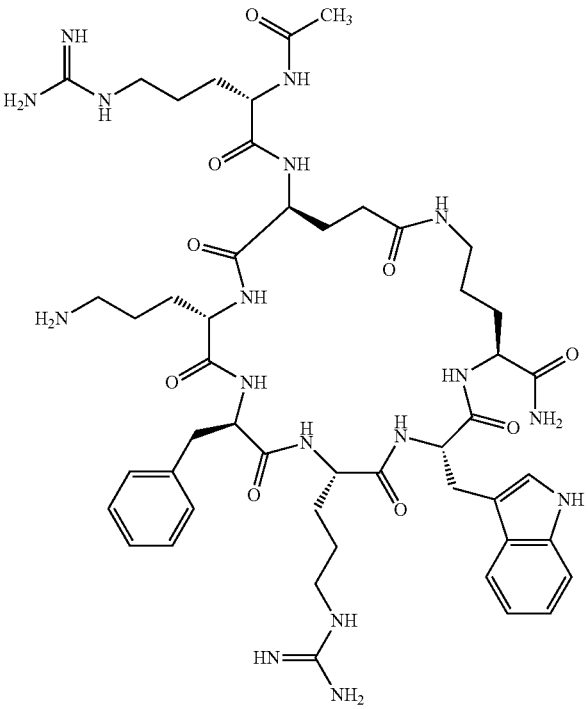 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCCN)NC1=O] | Ac-Arg-cyclo(Glu-Orn-D-Phe-Arg-Trp-Orn)-NH$_2$ | 9* |

| No. | Structure | Amino Acid Sequence | MC4-R Ki (nM) |
|---|---|---|---|
| 105 | 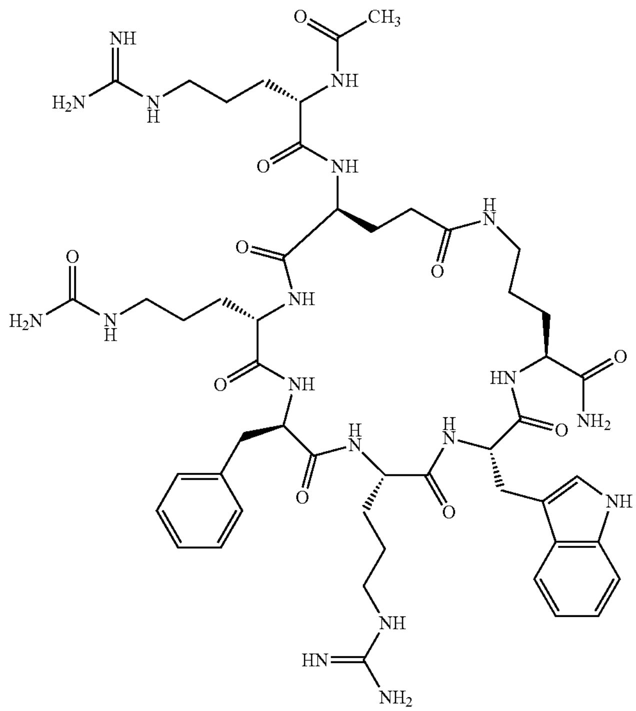 | Ac-Arg-cyclo(Glu-Cit-D-Phe-Arg-Trp-Orn)-NH₂ | 6 |
| 106 | 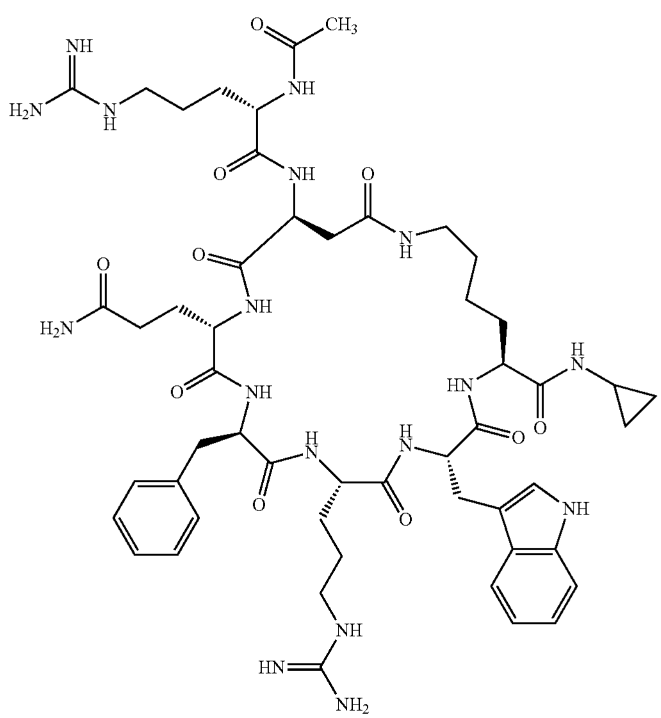 [SMILES: CC(=O)N[C@@H](CCCNC(=N)N)C(=O)N[C@H]1CC(=O)NCCCC[C@@H](C(=O)NC2CC2)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-Arg-cyclo(Asp-Gln-D-Phe-Arg-Trp-Lys)-NH-cyclopropyl | 64* |

| No. | Structure | Amino Acid Sequence | MC4-R Ki (nM) |
|---|---|---|---|
| 107 | 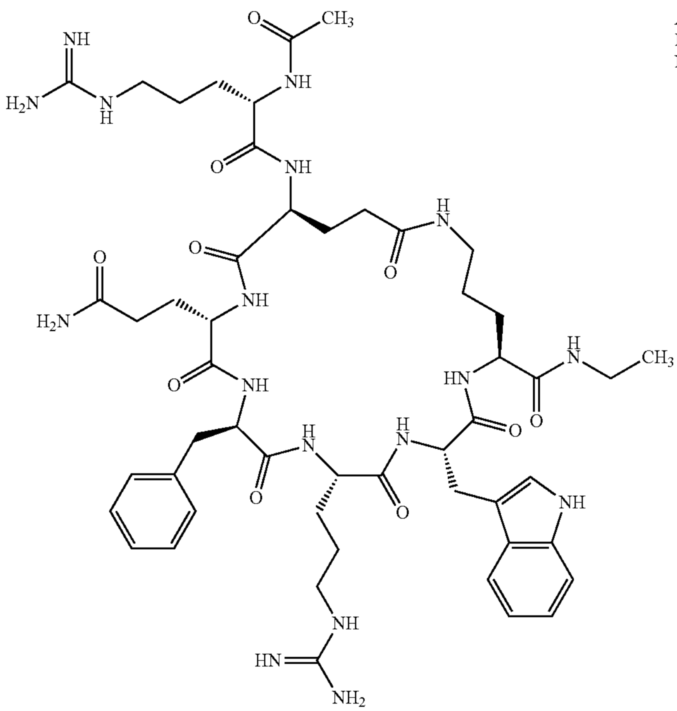 [SMILES: CCNC(=O)[C@@H]1CCCNC(=O)CC[C@H](NC(=O)[C@H](CCCNC(=N)N)NC(C)=O)C(=O)N[C@@H](CCC(N)=O)C(=O)N[C@H](Cc2ccccc2)C(=O)N[C@@H](CCCNC(=N)N)C(=O)N[C@@H](Cc2c[nH]c3ccccc23)C(=O)N1] | Ac-Arg-cyclo(Glu-Gln-D-Phe-Arg-Trp-Orn)-NH-Et | 34* |
| 108 | 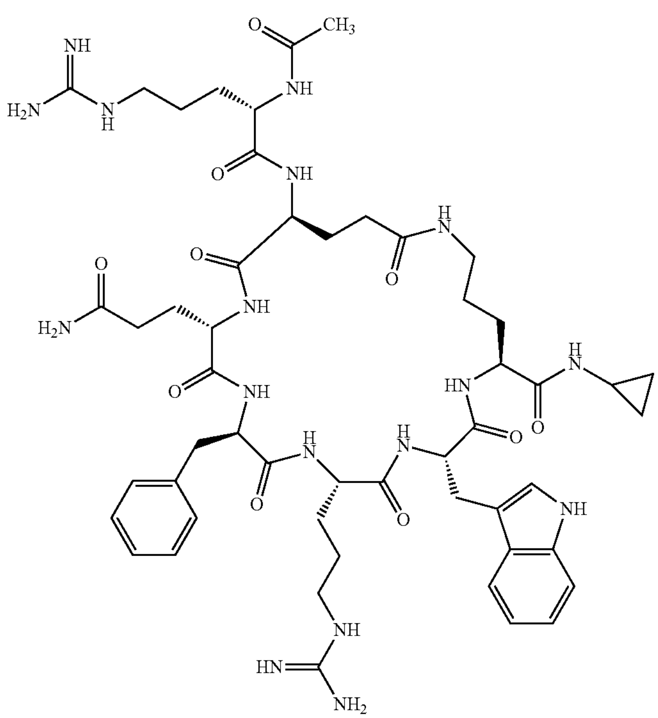 [SMILES: CC(=O)N[C@@H](CCCNC(=N)N)C(=O)N[C@H]1CCC(=O)NCCC[C@@H](C(=O)NC2CC2)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-Arg-cyclo(Glu-Gln-D-Phe-Arg-Trp-Orn)-NH-cyclopropyl | 26* |

| No. | Structure | Amino Acid Sequence | MC4-R Ki (nM) |
|---|---|---|---|
| 109 | 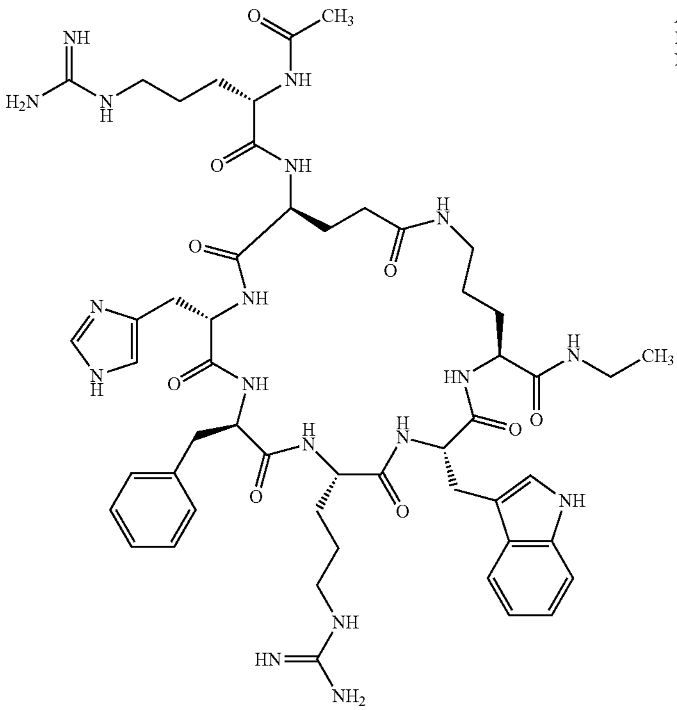 [SMILES: CCNC(=O)[C@@H]1CCCNC(=O)CC[C@H](NC(=O)[C@H](CCCNC(=N)N)NC(C)=O)C(=O)N[C@@H](Cc2c[nH]cn2)C(=O)N[C@H](Cc2ccccc2)C(=O)N[C@@H](CCCNC(=N)N)C(=O)N[C@@H](Cc2c[nH]c3ccccc23)C(=O)N1] | Ac-Arg-cyclo(Glu-His-D-Phe-Arg-Trp-Orn)-NH-Et | 6* |
| 110 | 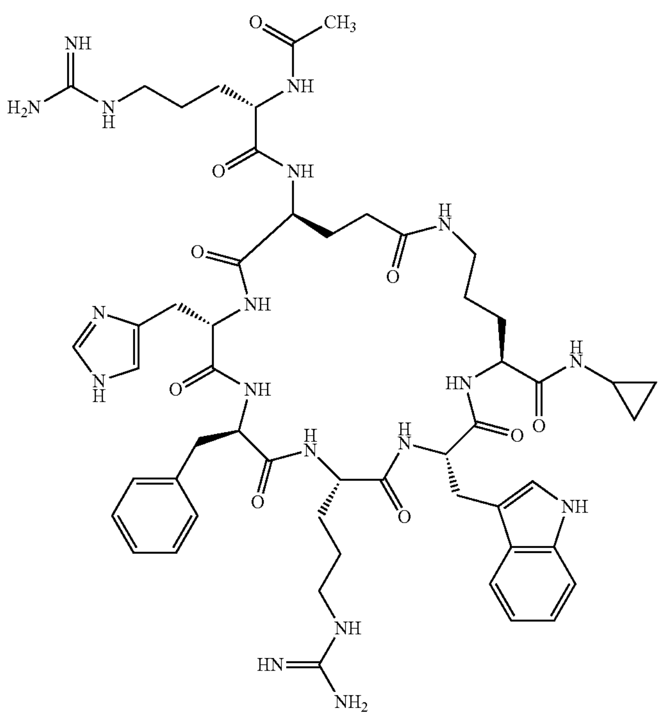 [SMILES: CC(=O)N[C@@H](CCCNC(=N)N)C(=O)N[C@H]1CCC(=O)NCCC[C@@H](C(=O)NC2CC2)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-cyclo(Glu-His-D-Phe-Arg-Trp-Orn)-NH-cyclopropyl | 1* |

| No. | Structure | Amino Acid Sequence | MC4-R Ki (nM) |
|---|---|---|---|
| 111 | 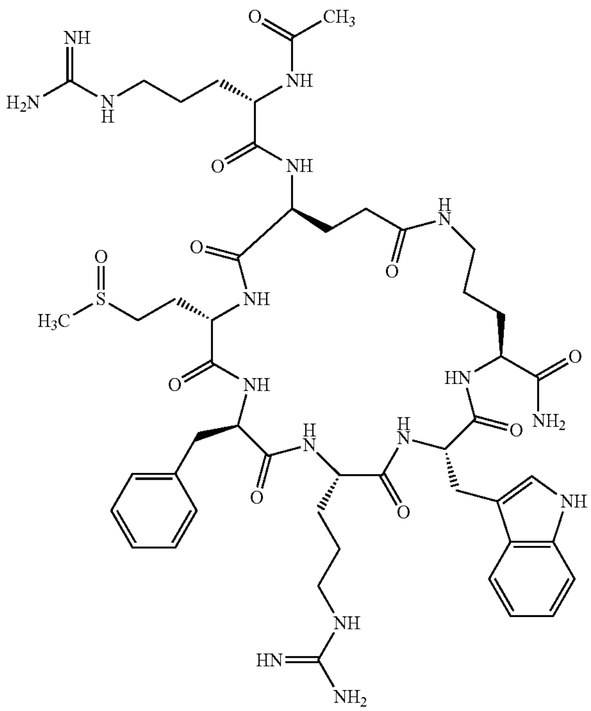 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCS(C)=O)NC1=O] | Ac-Arg-cyclo(Glu-Met(=O)-D-Phe-Arg-Trp-Orn)-NH₂ | 9 |
| 112 | 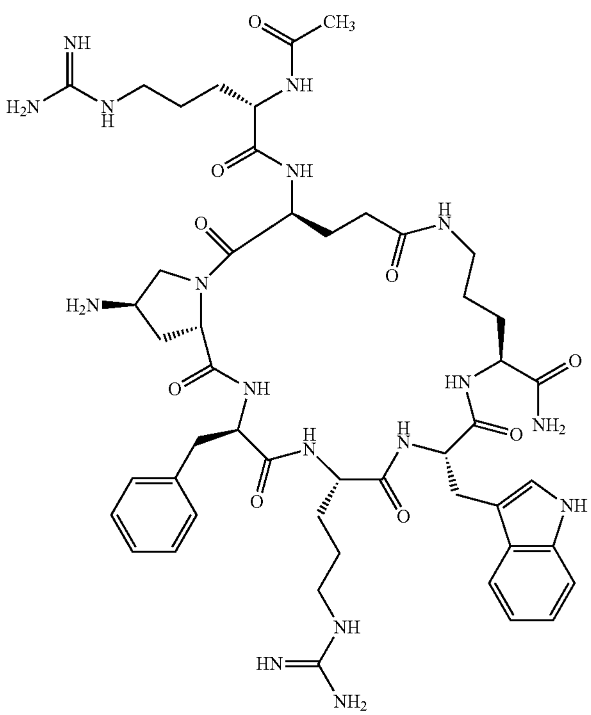 | Ac-Arg-Cyclo(Glu-Pro(4R—NH₂)-D-Phe-Arg-Trp-Orn)-NH₂ | 6 |

| No. | Structure | Amino Acid Sequence | MC4-R Ki (nM) |
|---|---|---|---|
| 113 | 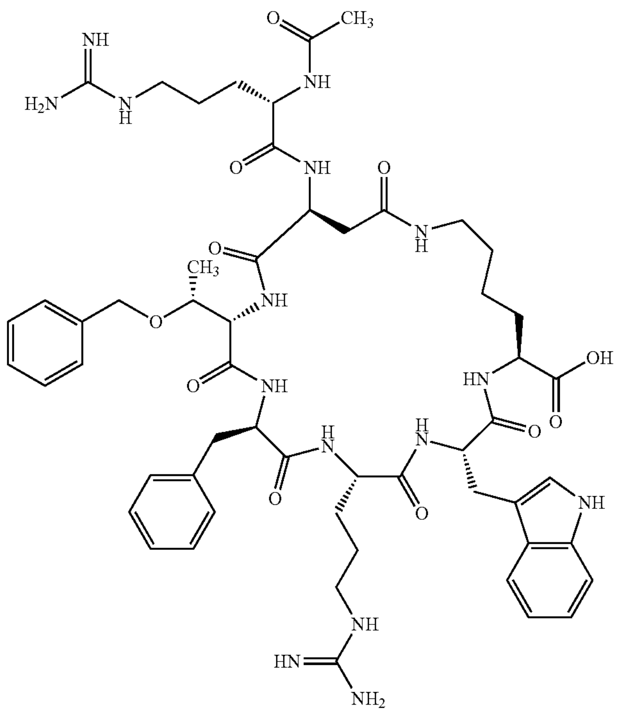 [SMILES: CC(=O)N[C@@H](CCCNC(=N)N)C(=O)N[C@H]1CC(=O)NCCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H]([C@@H](C)OCc2ccccc2)NC1=O] | Ac-Arg-cyclo(Asp-Thr(Bzl)-D-Phe-Arg-Trp-Lys)-OH | ND |
| 114 | 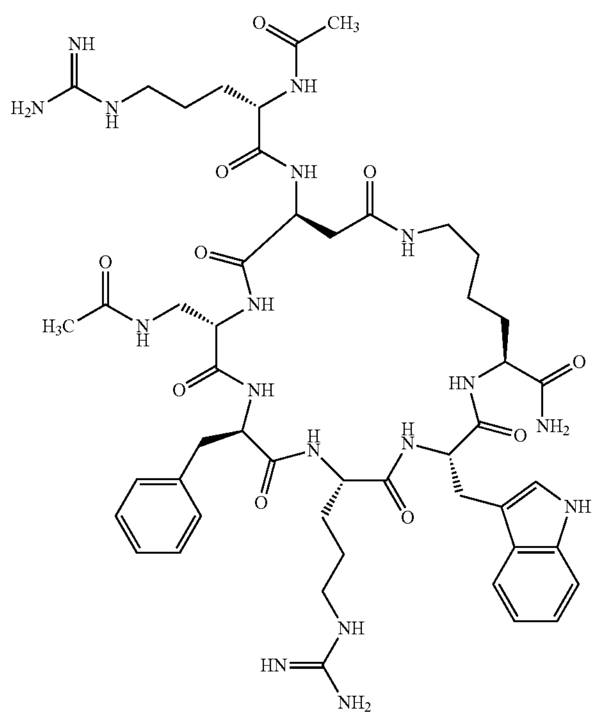 [SMILES: CC(=O)NC[C@@H]1NC(=O)[C@@H](NC(=O)[C@H](CCCNC(=N)N)NC(C)=O)CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC1=O] | Ac-Arg-cyclo(Asp-Dab(Acetyl)-D-Phe-Arg-Trp-Lys)-NH$_2$ | 88* |

| No. | Structure | Amino Acid Sequence | MC4-R Ki (nM) |
|---|---|---|---|
| 115 | 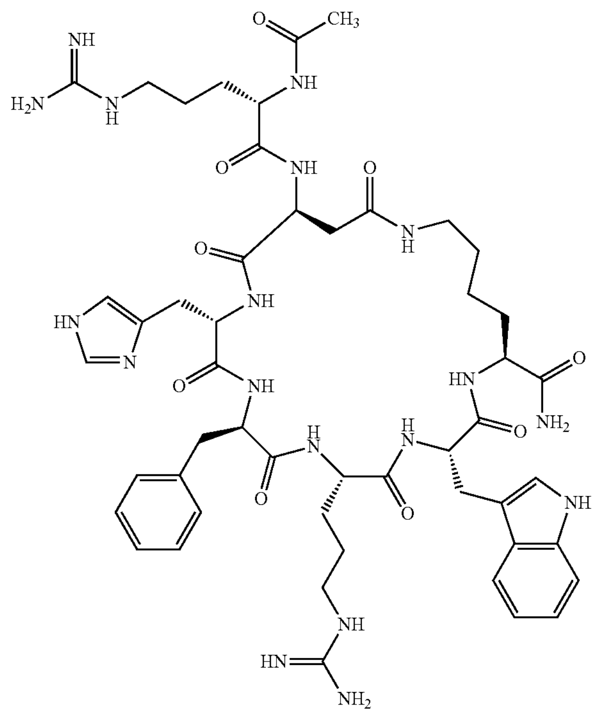 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-cyclo(Asp-His-D-Phe-Cit-Trp-Lys)-NH₂ | 87 |
| 116 | 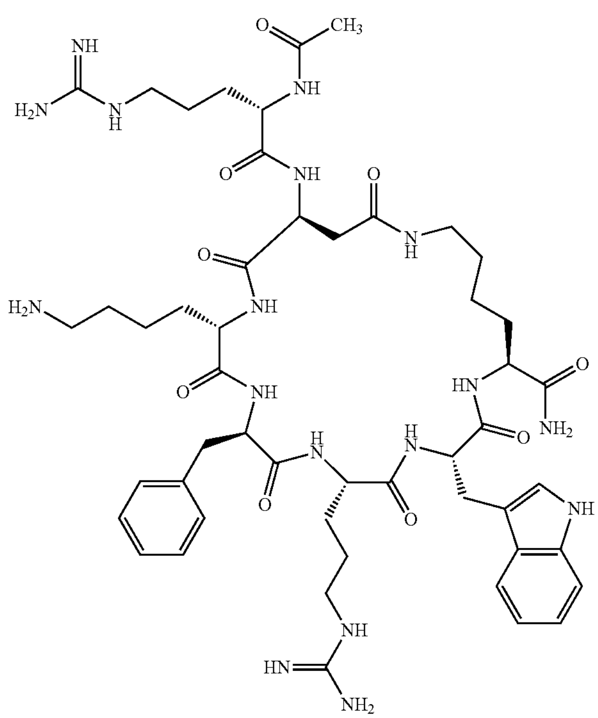 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCCCN)NC1=O] | Ac-Arg-cyclo(Asp-Lys-D-Phe-Cit-Trp-Lys)-NH₂ | 873 |

-continued
| No. | Structure | Amino Acid Sequence | MC4-R Ki (nM) |
|---|---|---|---|
| 117 | 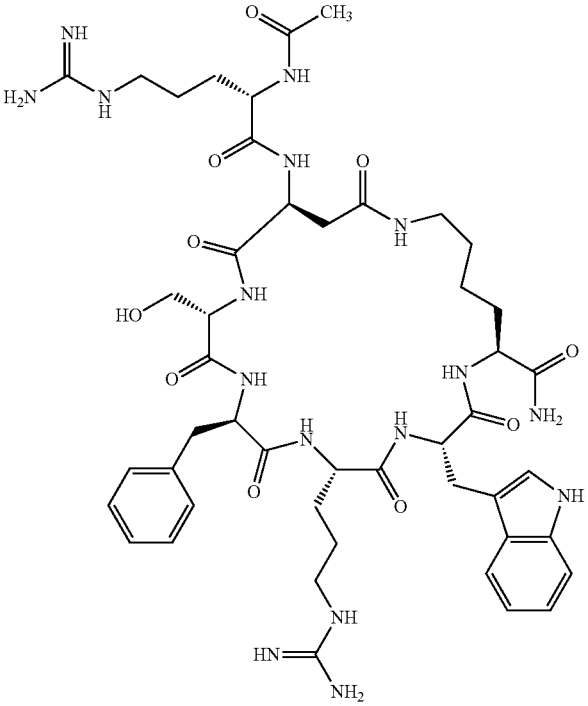 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CO)NC1=O] | Ac-Arg-cyclo(Asp-Ser-D-Phe-Cit-Trp-Lys)-NH₂ | 1446 |
| 118 | 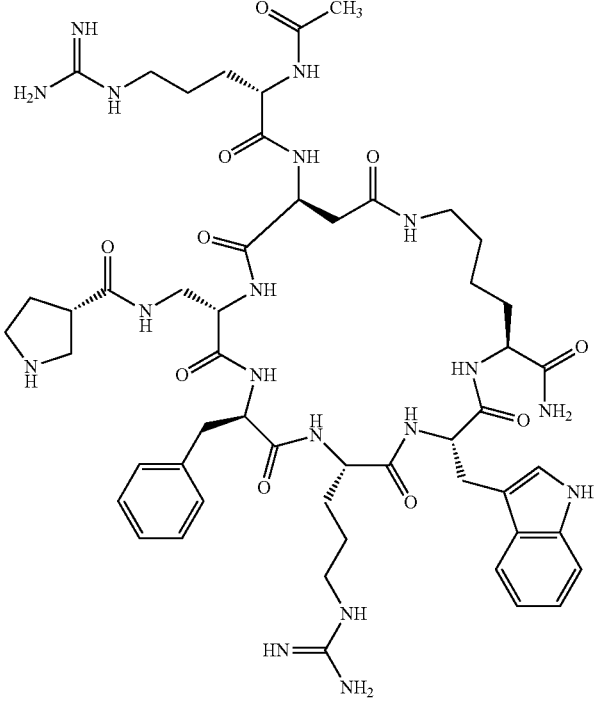 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CNC(=O)[C@H]2CCNC2)NC1=O] | Ac-Arg-cyclo(Asp-Dap(betaPro)-D-Ph-Arg-Trp-Lys)-NH₂ | 145* |

-continued

| No. | Structure | Amino Acid Sequence | MC4-R Ki (nM) |
|---|---|---|---|
| 119 | 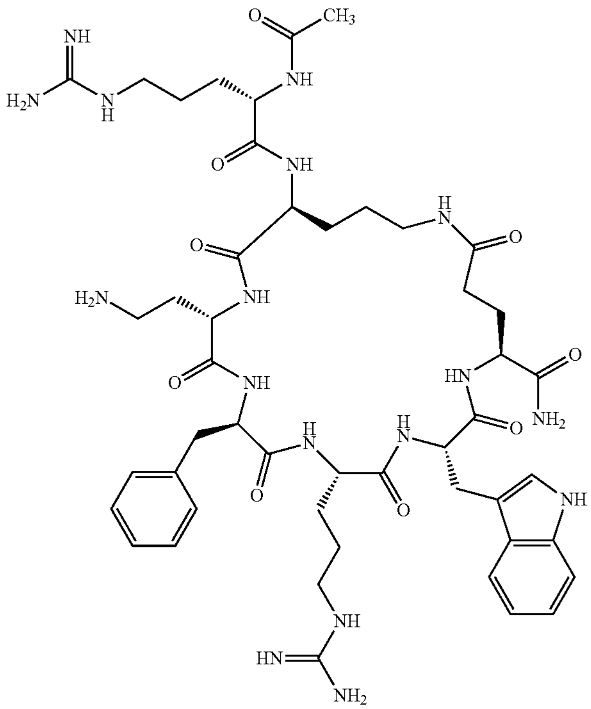 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Arg-cyclo(Orn-Dab-D-Phe-Arg-Trp-Glu)-NH$_2$ | 3* |
| 120 | 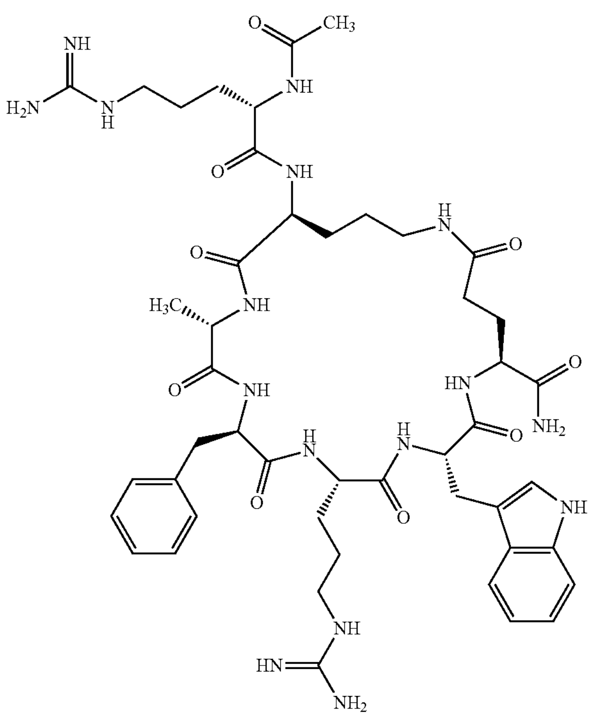 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](C)NC1=O] | Ac-Arg-cyclo(Orn-Ala-D-Phe-Arg-Trp-Glu)-NH$_2$ | 19* |

| No. | Structure | Amino Acid Sequence | MC4-R Ki (nM) |
|---|---|---|---|
| 121 | 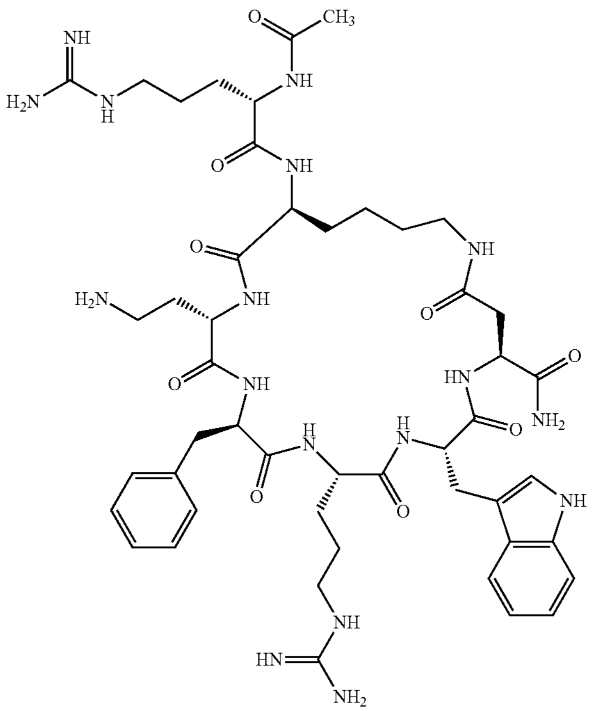 | Ac-Arg-cyclo(Lys-Dab-D-Phe-Arg-Trp-Asp)-NH$_2$ | 0.4 |
| 122 | 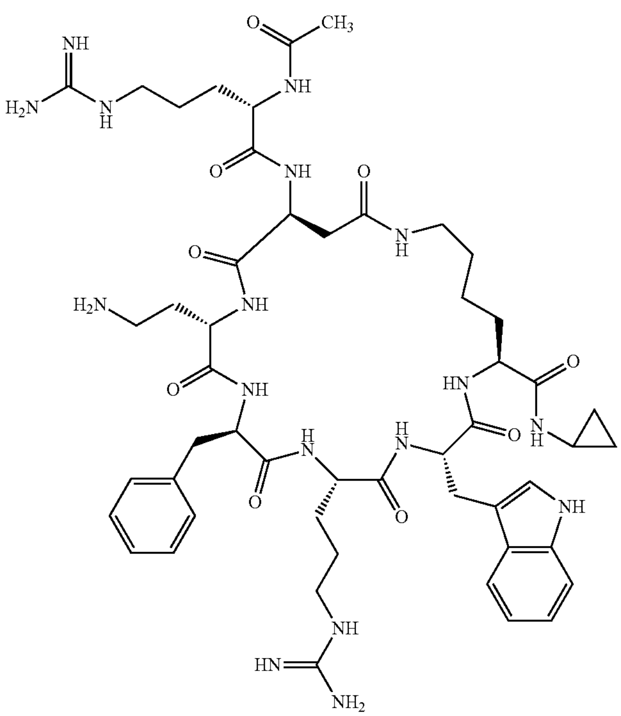 [SMILES: CC(=O)N[C@@H](CCCNC(=N)N)C(=O)N[C@H]1CC(=O)NCCCC[C@@H](C(=O)NC2CC2)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Arg-cyclo(Asp-Dab-D-Phe-Arg-Trp-Lys)-NH-cyclopropyl | 3 |

| No. | Structure | Amino Acid Sequence | MC4-R Ki (nM) |
|---|---|---|---|
| 123 | 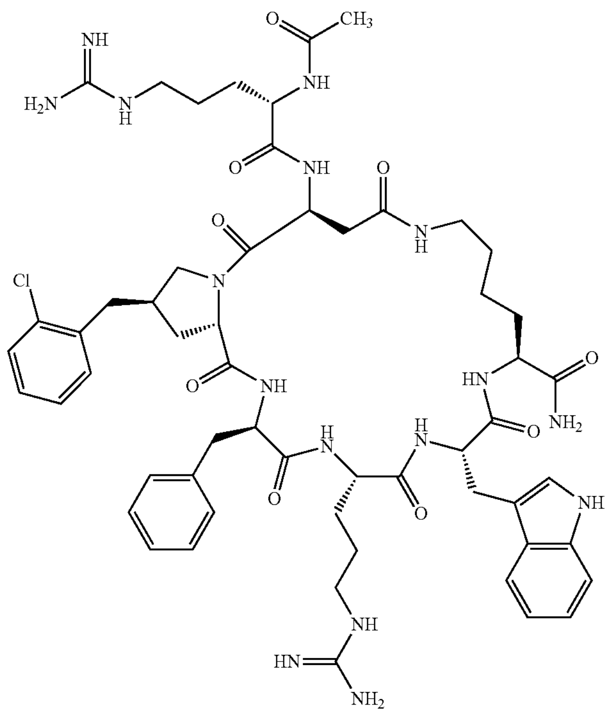 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]2C[C@@H](Cc3ccccc3Cl)CN2C1=O] | Ac-Arg-cyclo(Asp-Pro(4R-2-Cl-Bzl)-D-Phe-Arg-Trp-Lys)-NH$_2$ | 8* |
| 124 | 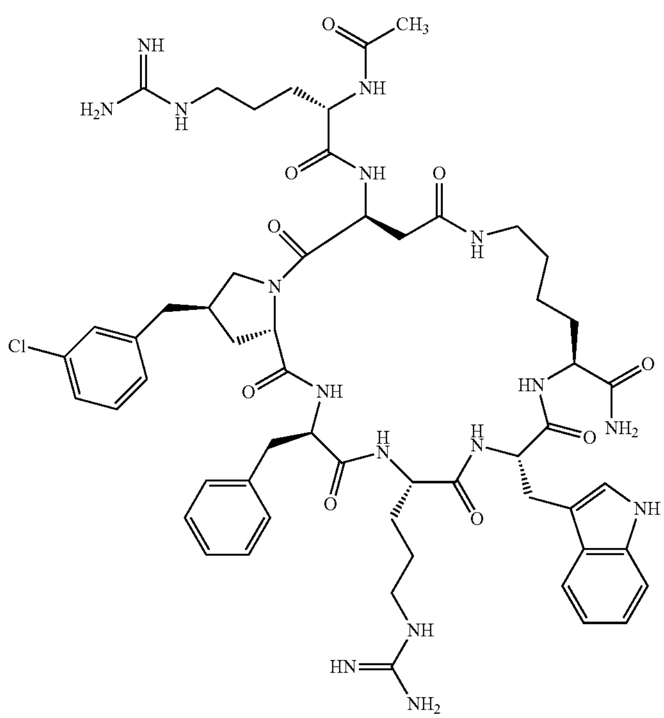 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]2C[C@@H](Cc3cccc(Cl)c3)CN2C1=O] | Ac-Arg-cyclo(Asp-Pro(4R-3-Cl-Bzl)-D-Phe-Arg-Trp-Lys)-NH$_2$ | 19* |

| No. | Structure | Amino Acid Sequence | MC4-R Ki (nM) |
|---|---|---|---|
| 125 | 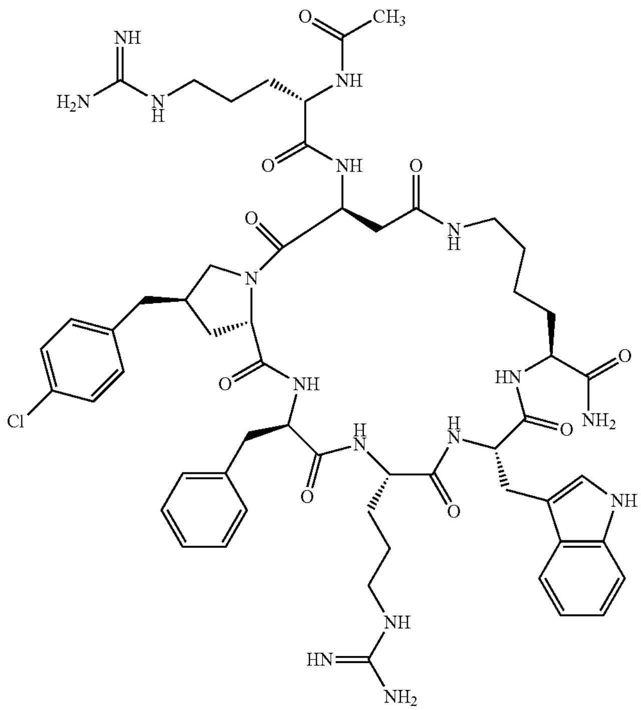 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]2C[C@@H](Cc3ccc(Cl)cc3)CN2C1=O] | Ac-Arg-cyclo(Asp-Pro(4R-4-Cl-Bzl)-D-Phe-Arg-Trp-Lys)-NH₂ | 24* |
| 126 | 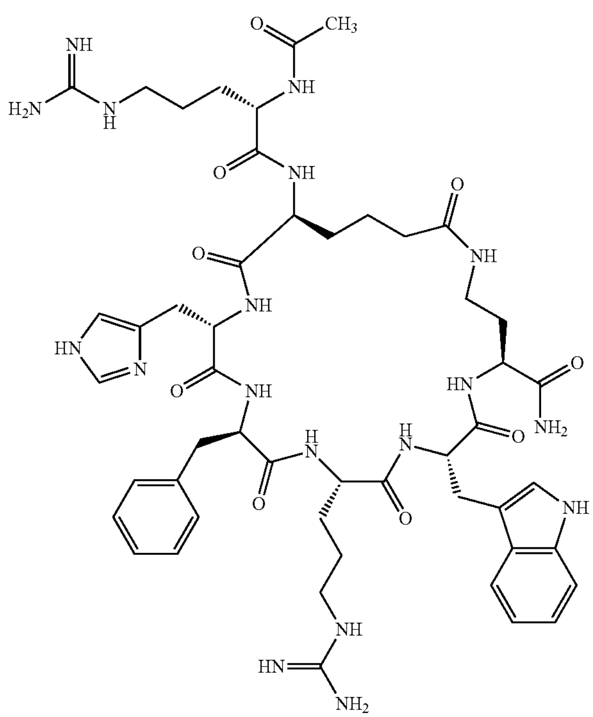 [SMILES: CC(=O)N[C@@H](CCCNC(=N)N)C(=O)N[C@H]1CCCC(=O)NCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-cyclo(hGlu-His-D-Phe-Arg-Trp-Dab)-NH₂ | 1* |

| No. | Structure | Amino Acid Sequence | MC4-R Ki (nM) |
|---|---|---|---|
| 127 | 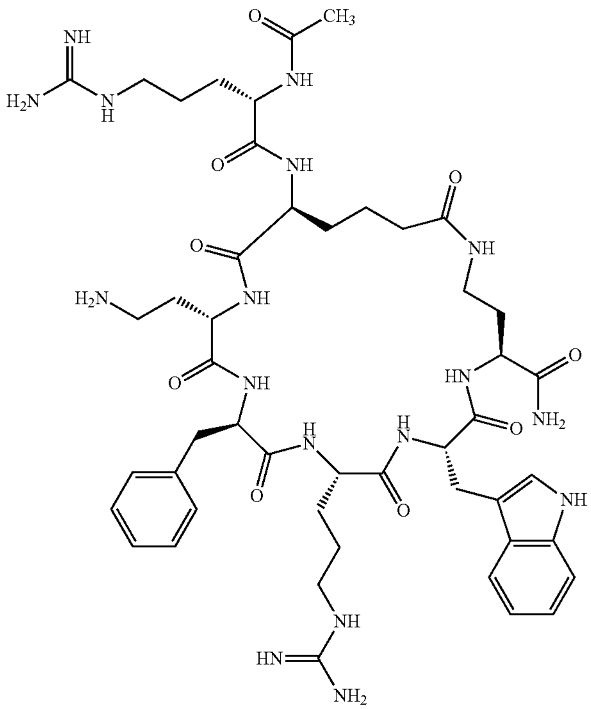 [SMILES: CC(=O)N[C@@H](CCCNC(=N)N)C(=O)N[C@H]1CCCC(=O)NCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Arg-cyclo(hGlu-Dab-D-Phe-Arg-Trp-Dab)-NH₂ | 2* |
| 128 | 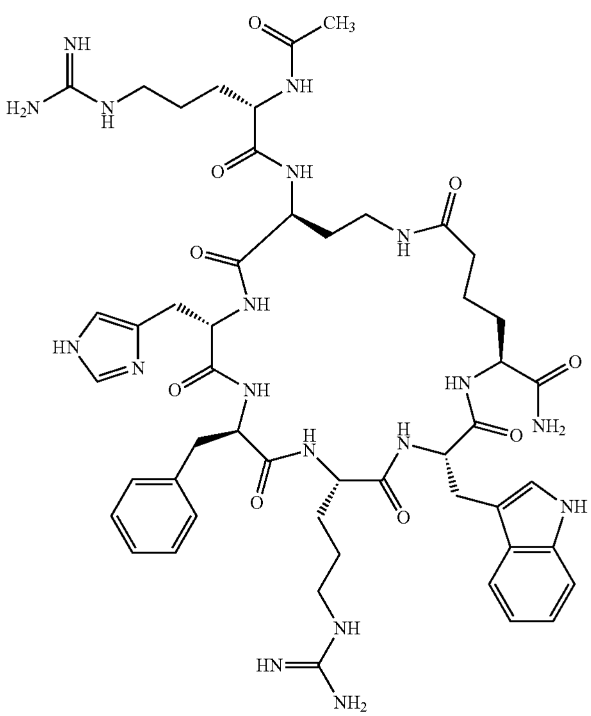 [SMILES: CC(=O)N[C@@H](CCCNC(=N)N)C(=O)N[C@H]1CCNC(=O)CCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-cyclo(Dab-His-D-Phe-Arg-Trp-hGlu)-NH₂ | 2* |

-continued

| No. | Structure | Amino Acid Sequence | MC4-R Ki (nM) |
|---|---|---|---|
| 129 | 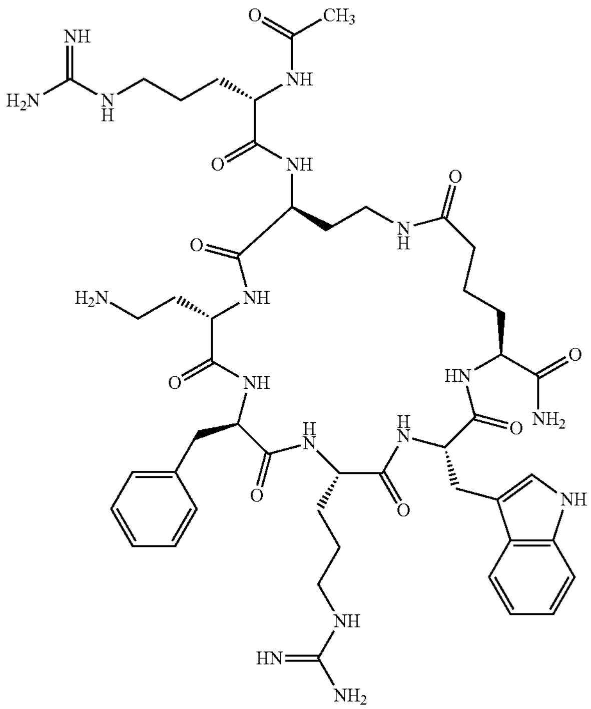 [SMILES: CC(=O)N[C@@H](CCCNC(=N)N)C(=O)N[C@H]1CCNC(=O)CCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Arg-cyclo(Dab-Dab-D-Phe-Arg-Trp-hGlu)-NH₂ | 4* |
| 130 | 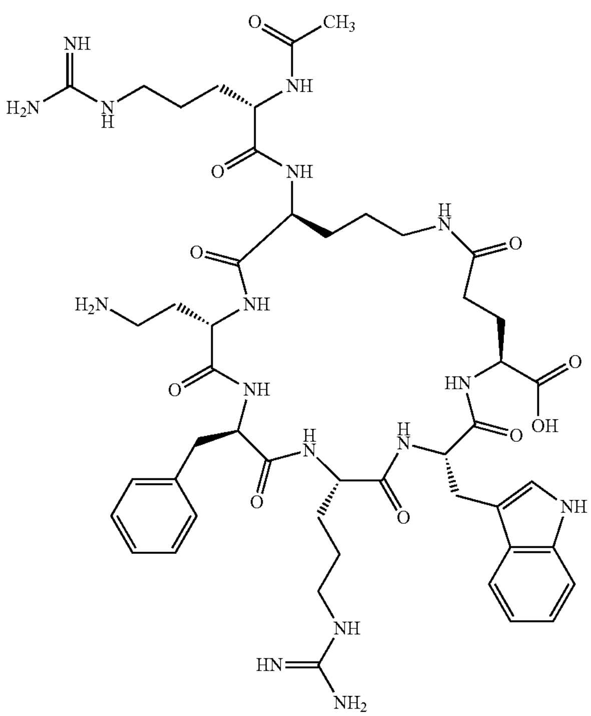 [SMILES: CC(=O)N[C@@H](CCCNC(=N)N)C(=O)N[C@H]1CCCNC(=O)CC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Arg-cyclo(Orn-Dab-D-Phe-Arg-Trp-Glu)-OH | 25 |

| No. | Structure | Amino Acid Sequence | MC4-R Ki (nM) |
|---|---|---|---|
| 131 | 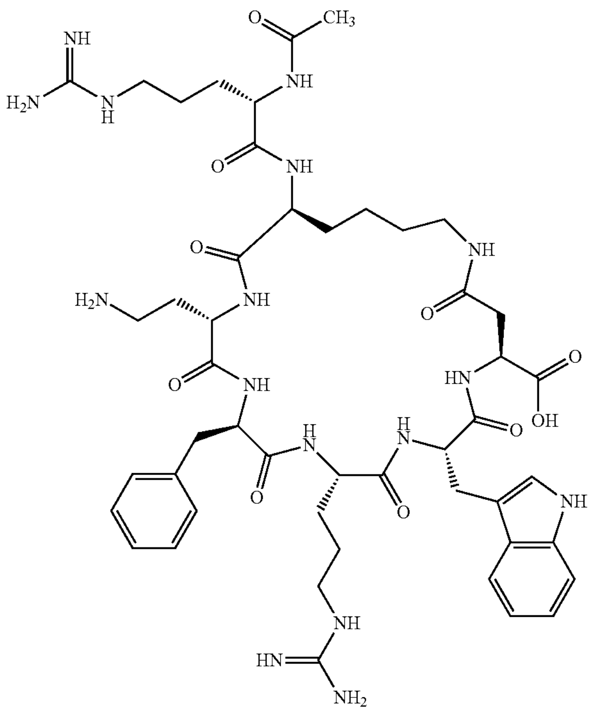 [SMILES: CC(=O)N[C@@H](CCCNC(=N)N)C(=O)N[C@H]1CCCCNC(=O)C[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Arg-cyclo(Lys-Dab-D-Phe-Arg-Trp-Asp)-OH | 35 |
| 132 | 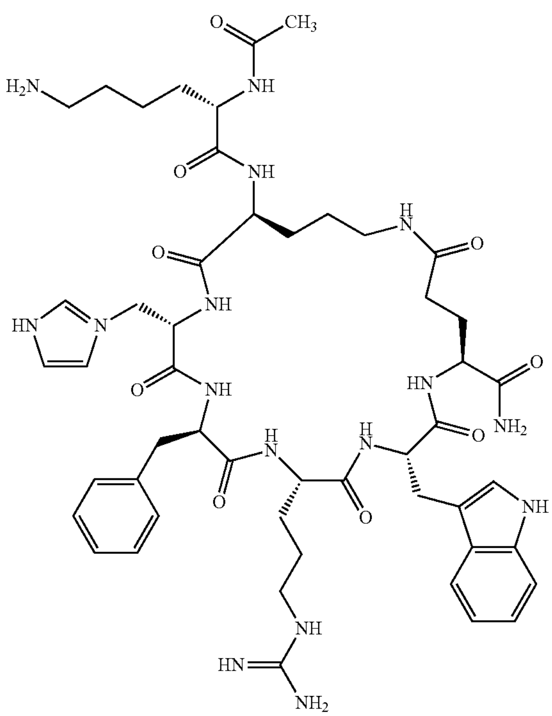 | Ac-Lys-cyclo(Orn-His-D-Phe-Arg-Trp-Glu)-NH$_2$ | 3* |

| No. | Structure | Amino Acid Sequence | MC4-R Ki (nM) |
|---|---|---|---|
| 133 | 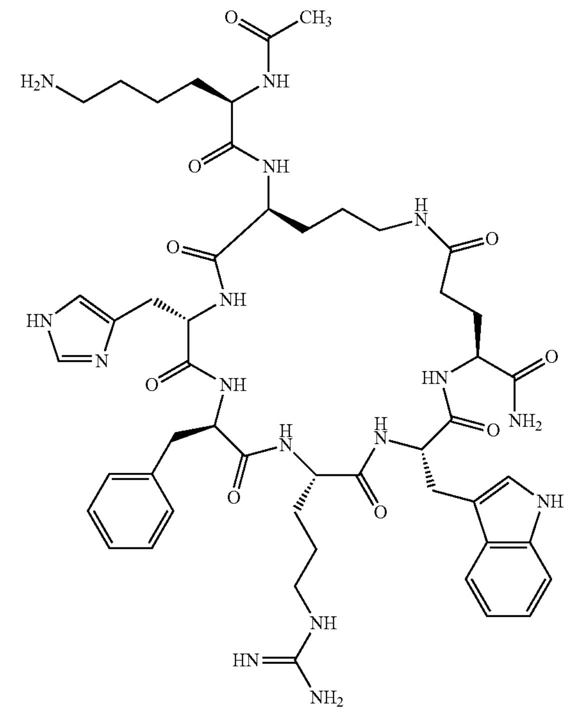 [SMILES: CC(=O)N[C@H](CCCCN)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-D-Lys-cyclo(Orn-His-D-Phe-Arg-Trp-Glu)-NH$_2$ | 8* |
| 134 | 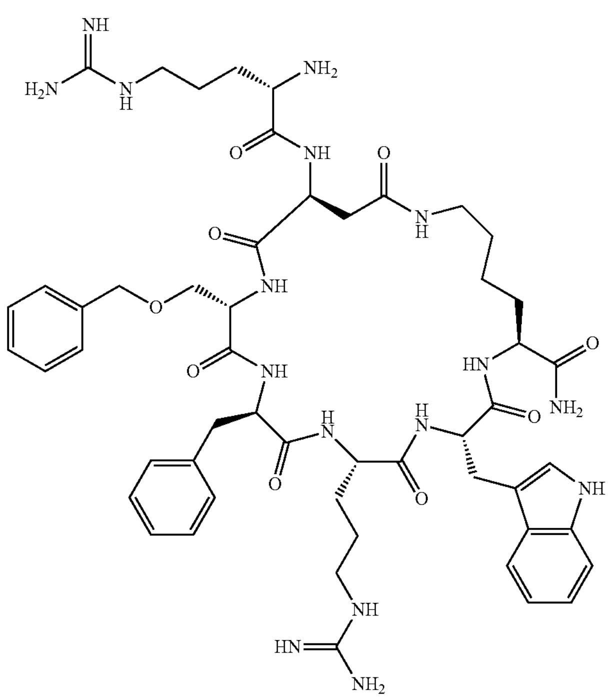 [SMILES: N=C(N)NCCC[C@@H]1NC(=O)[C@@H](Cc2ccccc2)NC(=O)[C@H](COCc2ccccc2)NC(=O)[C@@H](NC(=O)[C@@H](N)CCCNC(=N)N)CC(=O)NCCCC[C@@H](C(N)=O)NC(=O)[C@H](Cc2c[nH]c3ccccc23)NC1=O] | Arg-cyclo(Asp-Ser(Bzl)-D-Phe-Arg-Trp-Lys)-OH | 30 |

| No. | Structure | Amino Acid Sequence | MC4-R Ki (nM) |
|---|---|---|---|
| 135 | 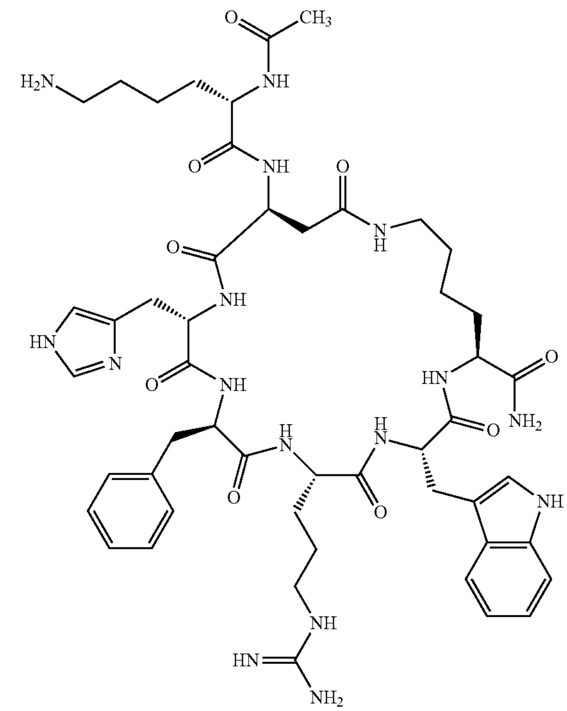 [SMILES: CC(=O)N[C@@H](CCCCN)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Lys-cyclo(Asp-His-D-Phe-Arg-Trp-Lys)-NH₂ | 9* |
| 136 | 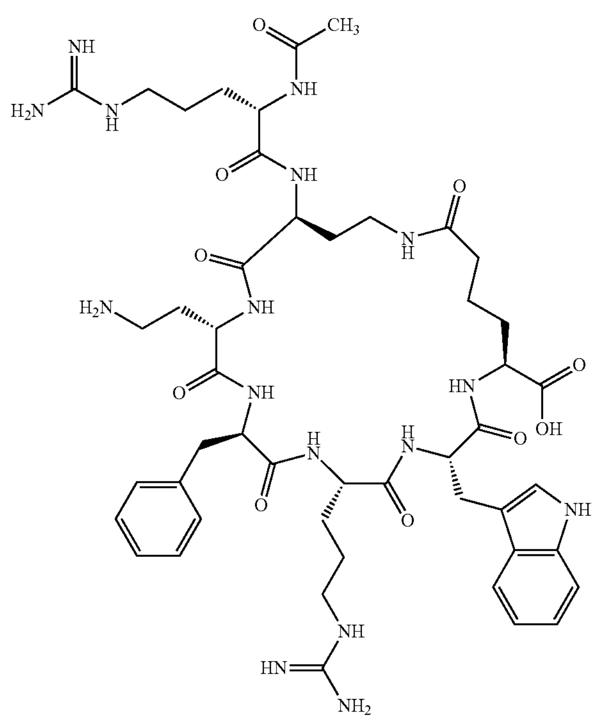 [SMILES: CC(=O)N[C@@H](CCCNC(=N)N)C(=O)N[C@H]1CCNC(=O)CCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Arg-cyclo(Dab-Dab-D-Phe-Arg-Trp-hGlu)-OH | 35 |

| No. | Structure | Amino Acid Sequence | MC4-R Ki (nM) |
|---|---|---|---|
| 137 | 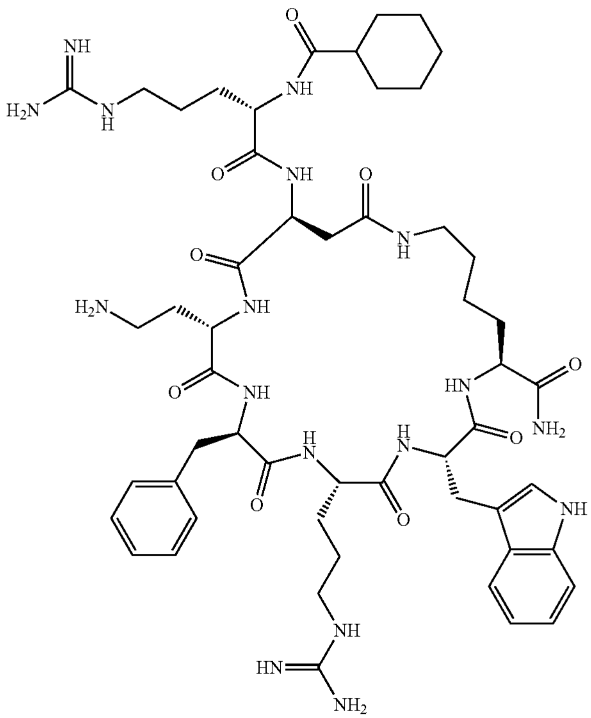 [SMILES: N=C(N)NCCC[C@H](NC(=O)C1CCCCC1)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Cyclohexanoyl-Arg-cyclo(Asp-Dab-D-Phe-Arg-Trp-Lys)-NH$_2$ | 0.4 |
| 138 | 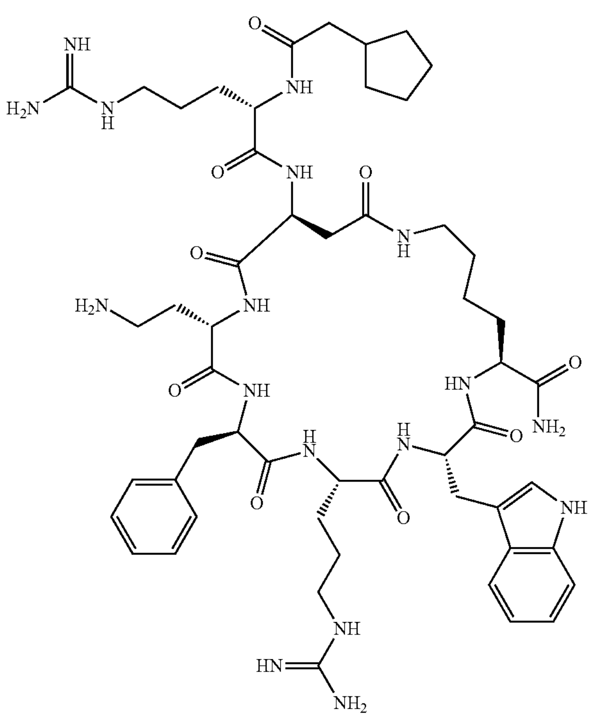 [SMILES: N=C(N)NCCC[C@H](NC(=O)CC1CCCC1)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Cyclopentylacetyl-Arg-cyclo(Asp-Dab-D-Phe-Arg-Trp-Lys)-NH$_2$ | 0.8 |

| No. | Structure | Amino Acid Sequence | MC4-R Ki (nM) |
|---|---|---|---|
| 139 | 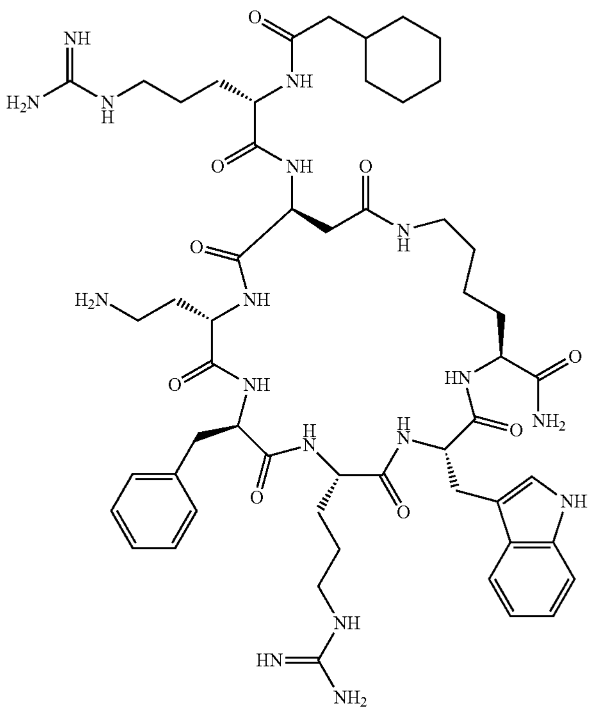 [SMILES: N=C(N)NCCC[C@H](NC(=O)CC1CCCCC1)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Cyclohexylacetyl-Arg-cyclo(Asp-Dab-D-Phe-Arg-Trp-Lys)-NH$_2$ | 1 |
| 140 | 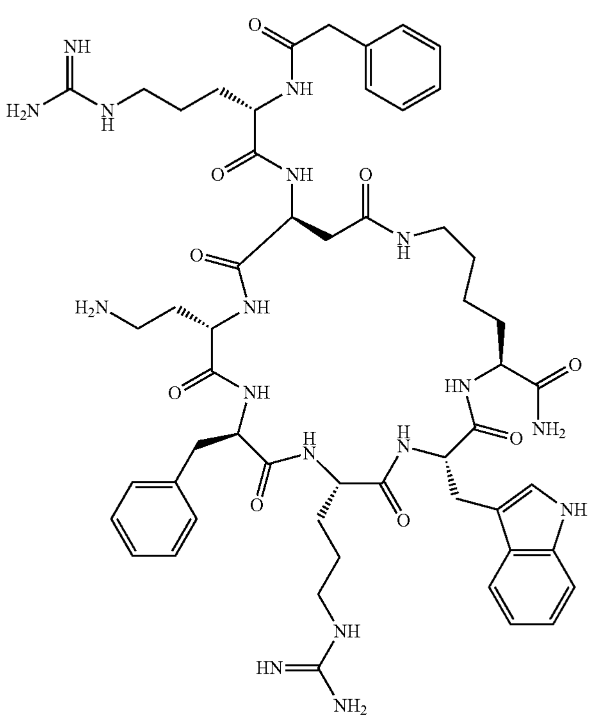 [SMILES: N=C(N)NCCC[C@H](NC(=O)Cc1ccccc1)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Phenylacetyl-Arg-cyclo(Asp-Dab-D-Phe-Arg-Trp-Lys)-NH$_2$ | 2 |

| No. | Structure | Amino Acid Sequence | MC4-R Ki (nM) |
|---|---|---|---|
| 141 | 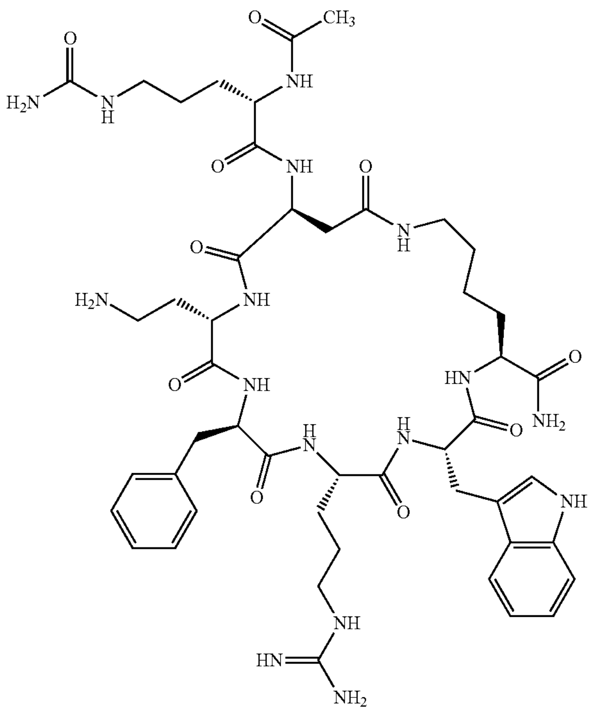 [SMILES: CC(=O)N[C@@H](CCCNC(N)=O)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Cit-cyclo(Asp-Dab-D-Phe-Arg-Trp-Lys)-NH₂ | 9 |
| 142 | 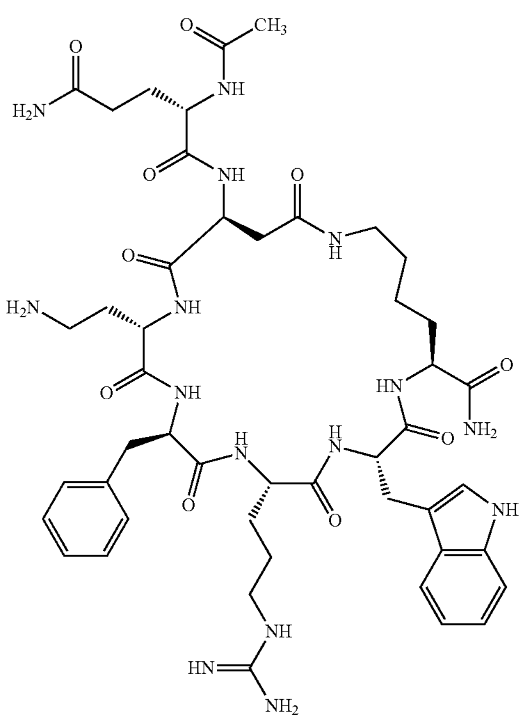 [SMILES: CC(=O)N[C@@H](CCC(N)=O)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Gln-cyclo(Asp-Dab-D-Phe-Arg-Trp-Lys)-NH₂ | 15 |

-continued

| No. | Structure | Amino Acid Sequence | MC4-R Ki (nM) |
|---|---|---|---|
| 143 | 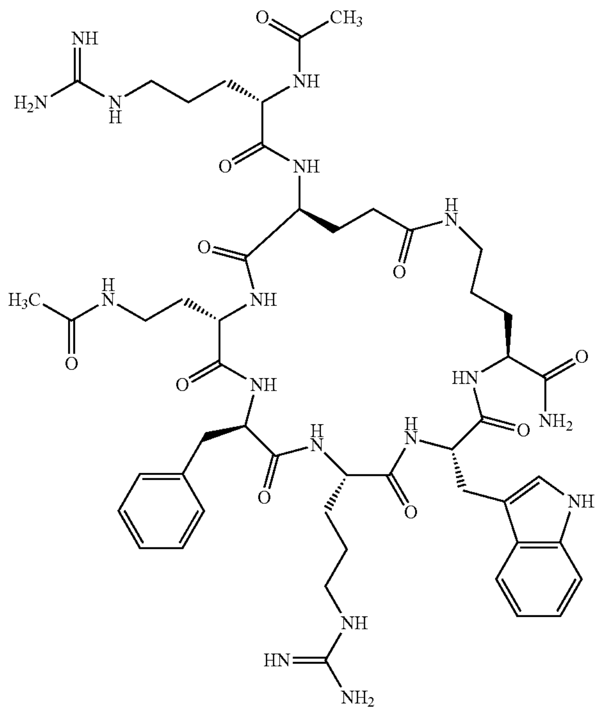 [SMILES: CC(=O)NCC[C@@H]1NC(=O)[C@@H](NC(=O)[C@H](CCCNC(=N)N)NC(C)=O)CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC1=O] | Ac-Arg-cyclo(Glu-Dab(Acetyl)-D-Phe-Arg-Trp-Orn)-NH₂ | 13 |
| 144 | 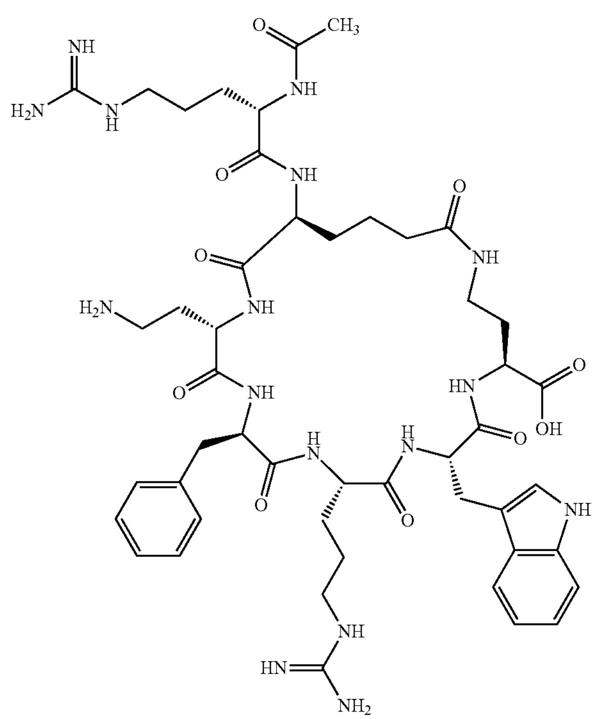 [SMILES: CC(=O)N[C@@H](CCCNC(=N)N)C(=O)N[C@H]1CCCC(=O)NCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O] | Ac-Arg-cyclo(hGlu-Dab-D-Phe-Arg-Trp-Dab)-OH | 45 |

| No. | Structure | Amino Acid Sequence | MC4-R Ki (nM) |
|---|---|---|---|
| 145 | 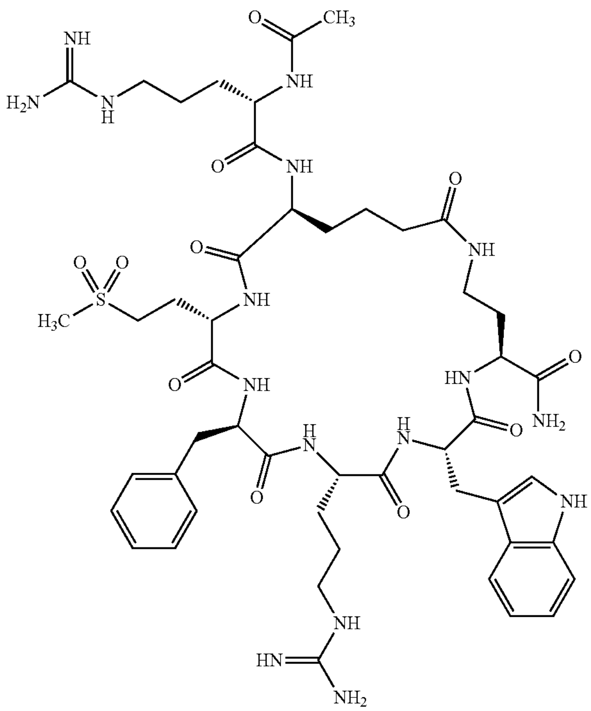 [SMILES: CC(=O)N[C@@H](CCCNC(=N)N)C(=O)N[C@H]1CCCC(=O)NCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCS(C)(=O)=O)NC1=O] | Ac-Arg-cyclo(hGlu-Met(O₂)-D-Phe-Arg-Trp-Dab)-NH₂ | 4 |
| 146 | 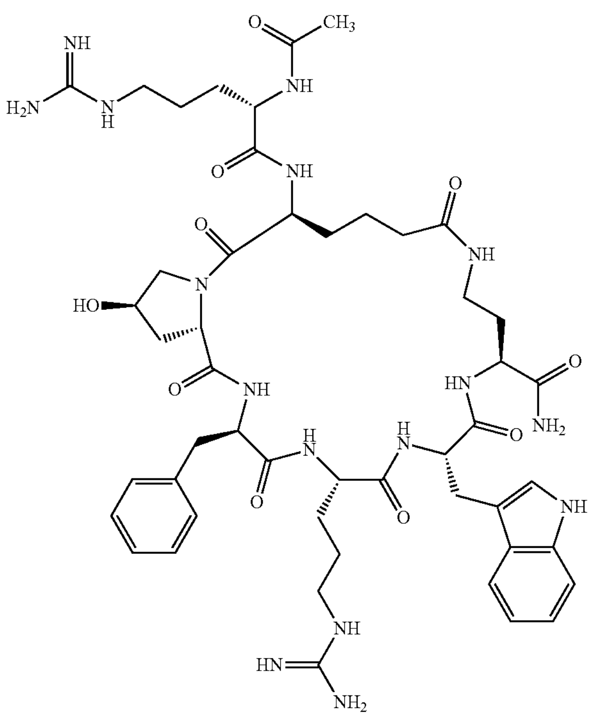 [SMILES: CC(=O)N[C@@H](CCCNC(=N)N)C(=O)N[C@H]1CCCC(=O)NCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@@H]2C[C@@H](O)CN2C1=O] | Ac-Arg-cyclo(hGlu-Hyp-D-Phe-Arg-Trp-Dab)-NH₂ | 3 |

-continued

| No. | Structure | Amino Acid Sequence | MC4-R Ki (nM) |
|---|---|---|---|
| 147 | 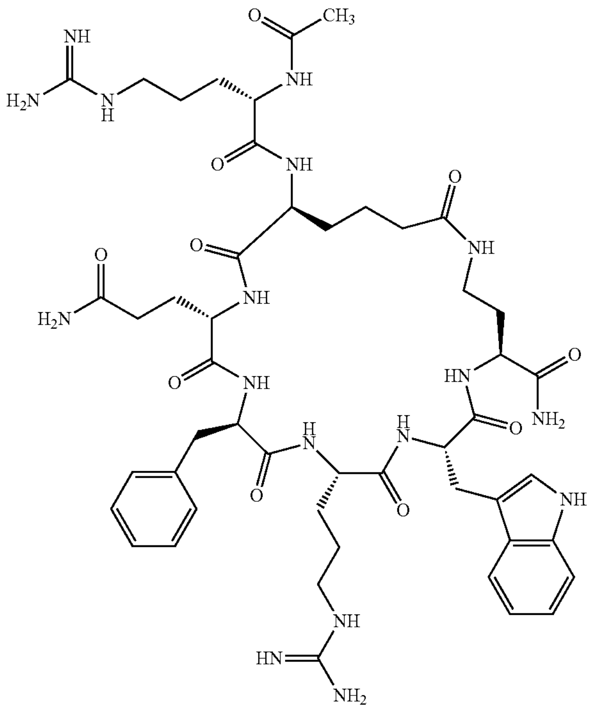 [SMILES: CC(=O)N[C@@H](CCCNC(=N)N)C(=O)N[C@H]1CCCC(=O)NCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-Arg-cyclo(hGlu-Gln-D-Phe-Arg-Trp-Dab)-NH$_2$ | 20 |
| 148 | 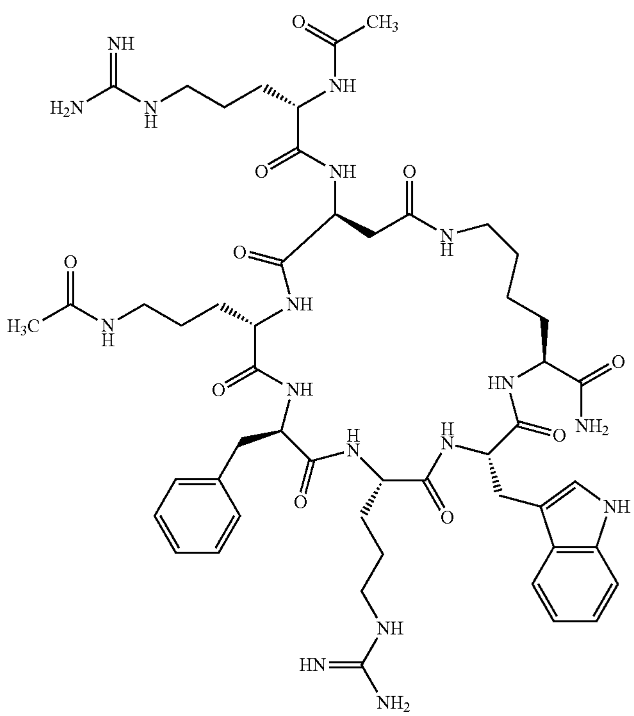 [SMILES: CC(=O)NCCC[C@@H]1NC(=O)[C@@H](NC(=O)[C@H](CCCNC(=N)N)NC(C)=O)CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC1=O] | Ac-Arg-cyclo(Asp-Orn(Acetyl)-D-Phe-Arg-Trp-Lys)-NH$_2$ | 573 |

| No. | Structure | Amino Acid Sequence | MC4-R Ki (nM) |
|---|---|---|---|
| 149 | 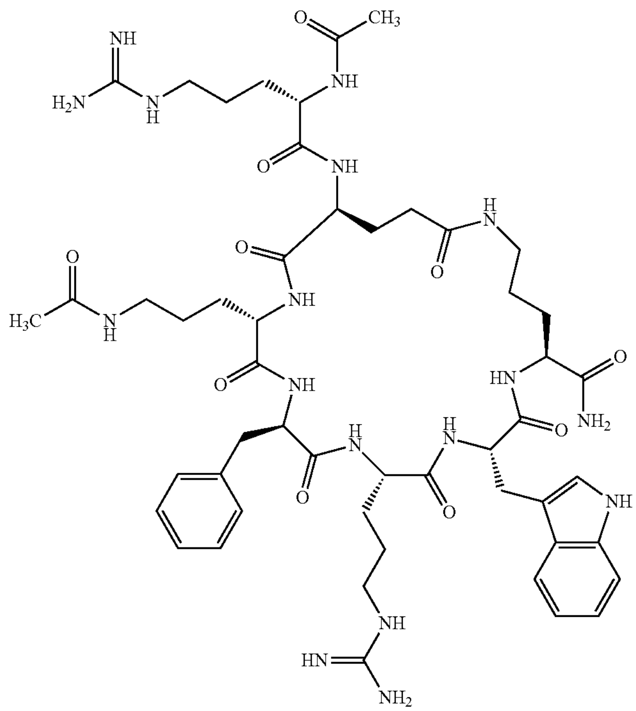 [SMILES: CC(=O)NCCC[C@@H]1NC(=O)[C@@H](NC(=O)[C@H](CCCNC(=N)N)NC(C)=O)CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC1=O] | Ac-Arg-cyclo(Glu-Orn(Acetyl)-D-Phe-Arg-Trp-Orn)-NH₂ | 7 |
| 150 | 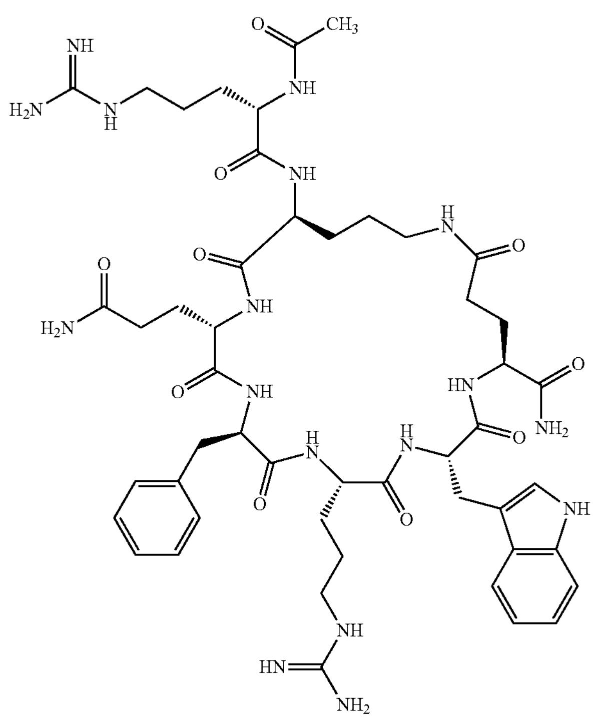 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-Arg-cyclo(Orn-Gln-D-Phe-Arg-Trp-Glu)-NH₂ | 5 |

| No. | Structure | Amino Acid Sequence | MC4-R Ki (nM) |
|---|---|---|---|
| 151 | 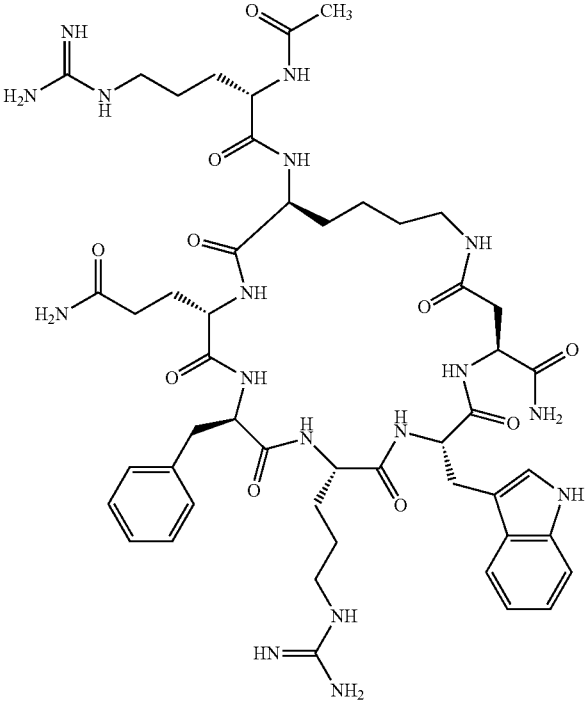 [SMILES: CC(=O)N[C@@H](CCCNC(=N)N)C(=O)N[C@H]1CCCCNC(=O)C[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-Arg-cyclo(Lys-Gln-D-Phe-Arg-Trp-Asp)-NH$_2$ | 4 |
| 152 | 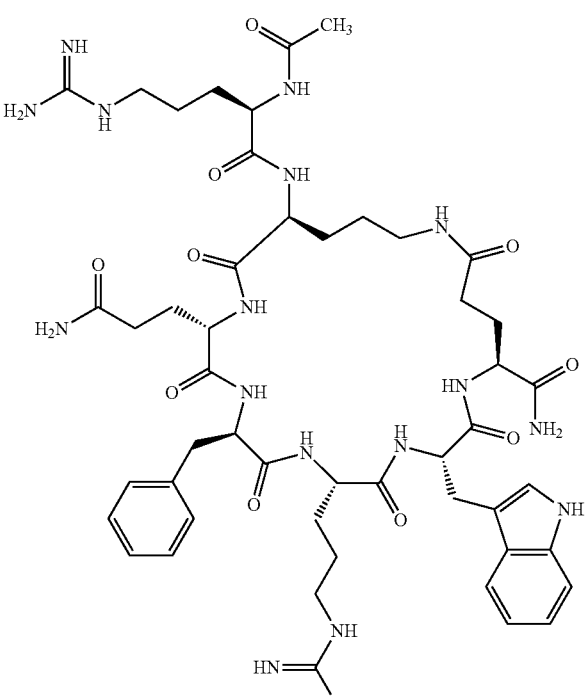 | Ac-D-Arg-cyclo(Orn-Gln-D-Phe-Arg-Trp-Glu)-NH$_2$ | 6 |

-continued

| No. | Structure | Amino Acid Sequence | MC4-R Ki (nM) |
|---|---|---|---|
| 153 | 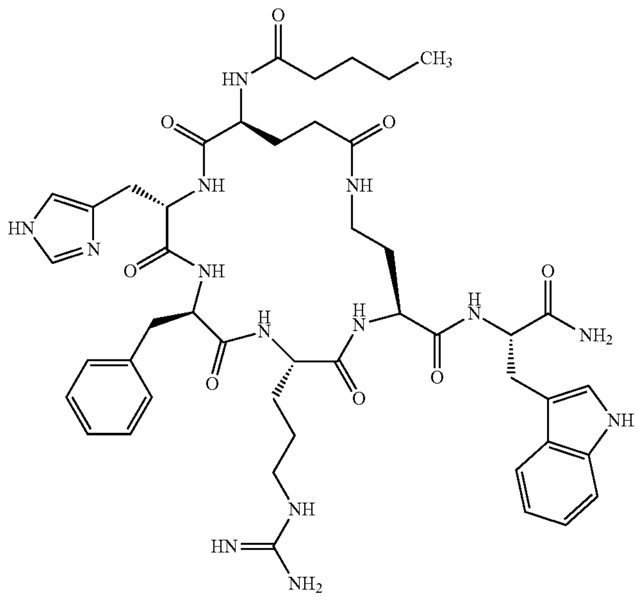 [SMILES: CCCCC(=O)N[C@H]1CCC(=O)NCC[C@@H](C(=O)N[C@@H](Cc2c[nH]c3ccccc23)C(N)=O)NC(=O)[C@H](CCCNC(=N)N)NC(=O)[C@@H](Cc2ccccc2)NC(=O)[C@H](Cc2c[nH]cn2)NC1=O] | n-C$_4$H$_9$—CO-cyclo(Glu-His-D-Phe-Arg-Dab)-Trp-NH$_2$ | 365 |
| 154 | 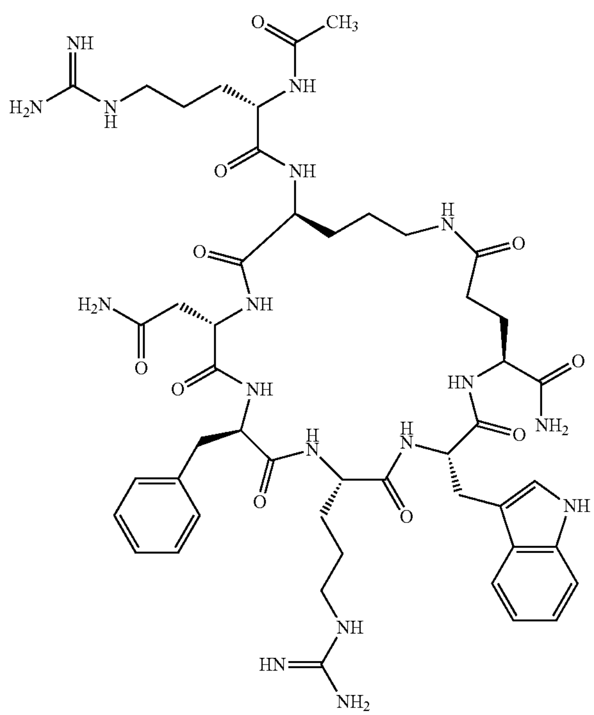 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O] | Ac-Arg-cyclo(Orn-Asn-D-Phe-Arg-Trp-Glu)-NH$_2$ | 13 |

| No. | Structure | Amino Acid Sequence | MC4-R Ki (nM) |
|---|---|---|---|
| 155 | 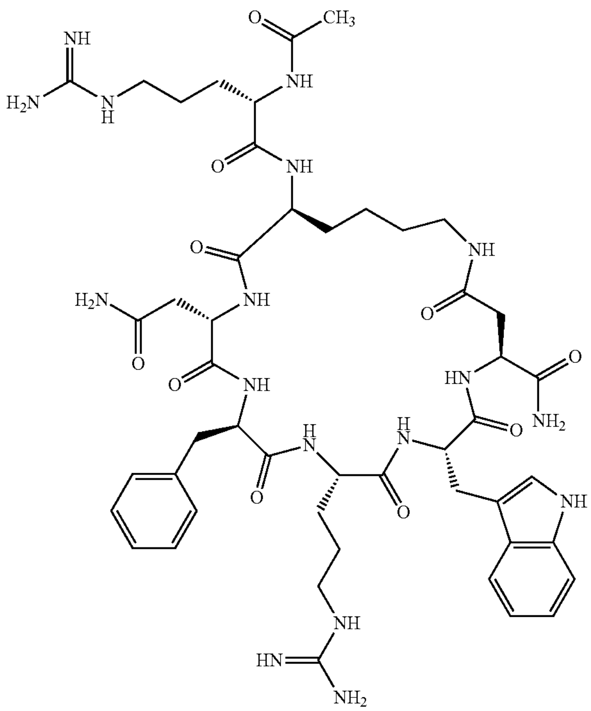 [SMILES: CC(=O)N[C@@H](CCCNC(=N)N)C(=O)N[C@H]1CCCCNC(=O)C[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O] | Ac-Arg-cyclo(Lys-Asn-D-Phe-Arg-Trp-Asp)-NH₂ | 5 |
| 156 | 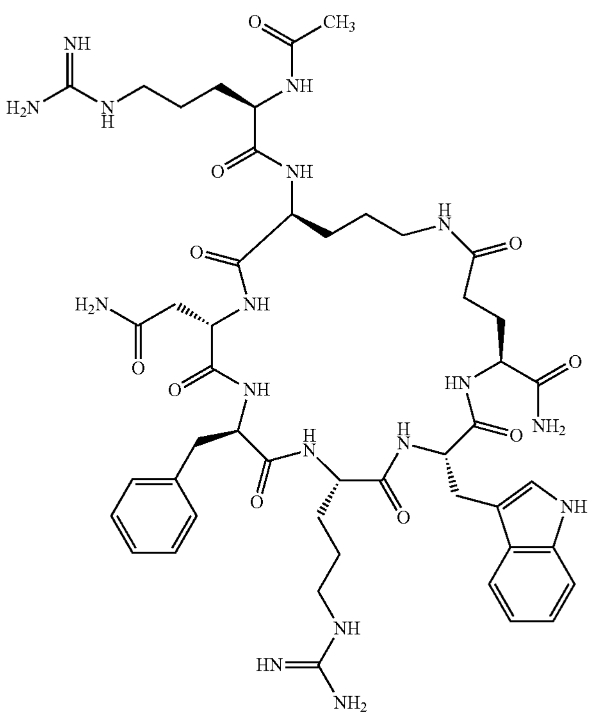 [SMILES: CC(=O)N[C@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O] | Ac-D-Arg-cyclo(Orn-Asn-D-Phe-Arg-Trp-Glu)-NH₂ | 28 |

-continued

| No. | Structure | Amino Acid Sequence | MC4-R Ki (nM) |
|---|---|---|---|
| 157 | 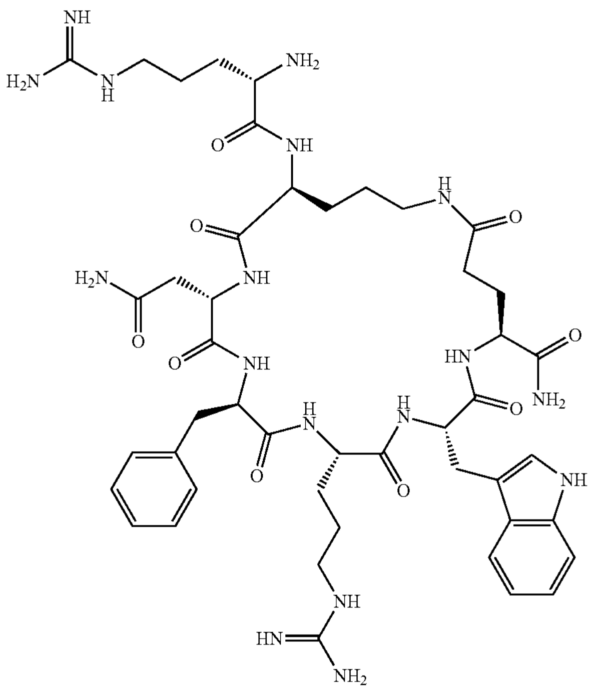 [SMILES: N=C(N)NCCC[C@@H]1NC(=O)[C@@H](Cc2ccccc2)NC(=O)[C@H](CC(N)=O)NC(=O)[C@@H](NC(=O)[C@@H](N)CCCNC(=N)N)CCCNC(=O)CC[C@@H](C(N)=O)NC(=O)[C@H](Cc2c[nH]c3ccccc23)NC1=O] | Arg-cyclo(Orn-Asn-D-Phe-Arg-Trp-Glu)-NH$_2$ | 42 |
| 158 | 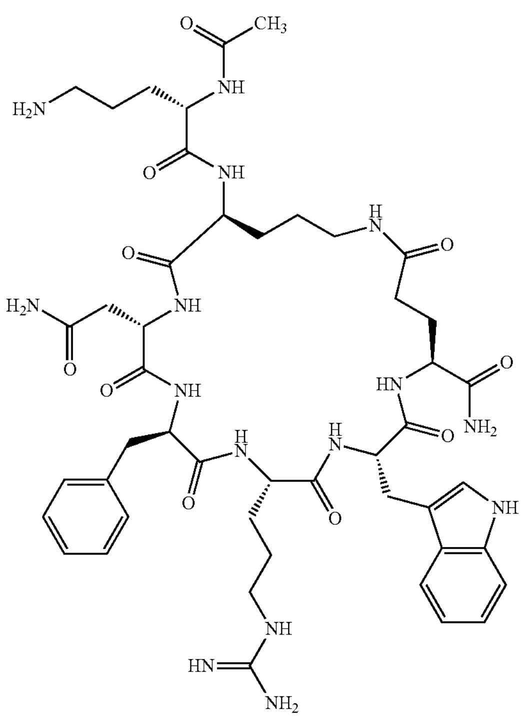 [SMILES: CC(=O)N[C@@H](CCCN)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O] | Ac-Orn-cyclo(Orn-Asn-D-Phe-Arg-Trp-Glu)-NH$_2$ | 50 |

| No. | Structure | Amino Acid Sequence | MC4-R Ki (nM) |
|---|---|---|---|
| 159 | 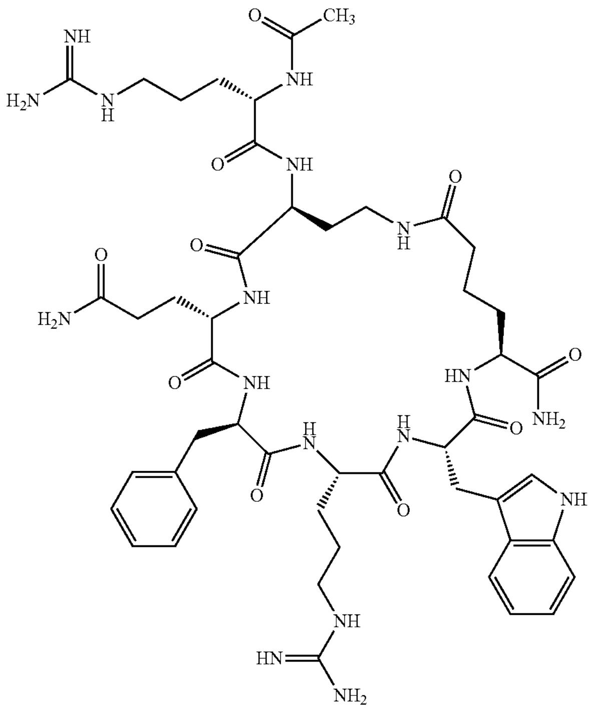 [SMILES: CC(=O)N[C@@H](CCCNC(=N)N)C(=O)N[C@H]1CCNC(=O)CCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCC(N)=O)NC1=O] | Ac-Arg-cyclo(Dab-Gln-D-Phe-Arg-Trp-hGlu)-NH$_2$ | 4 |
| 160 | 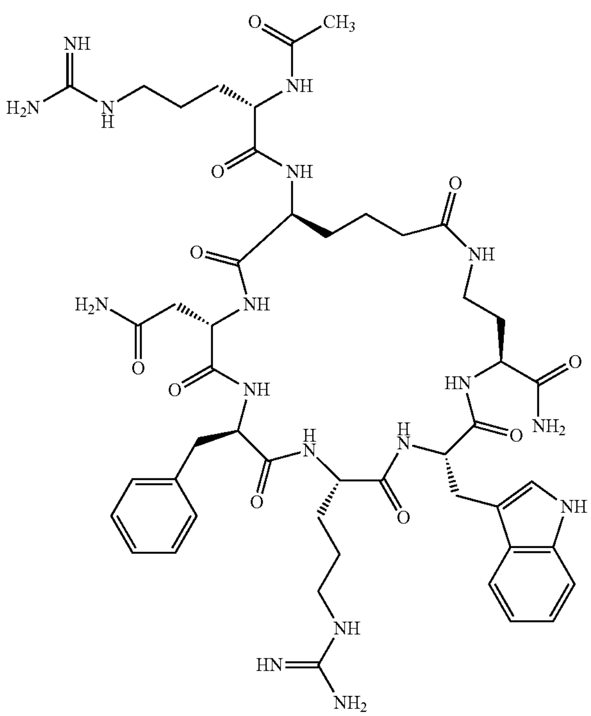 [SMILES: CC(=O)N[C@@H](CCCNC(=N)N)C(=O)N[C@H]1CCCC(=O)NCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O] | Ac-Arg-cyclo(hGlu-Asn-D-Phe-Arg-Trp-Dab)-NH$_2$ | 8 |

| No. | Structure | Amino Acid Sequence | MC4-R Ki (nM) |
|---|---|---|---|
| 161 | 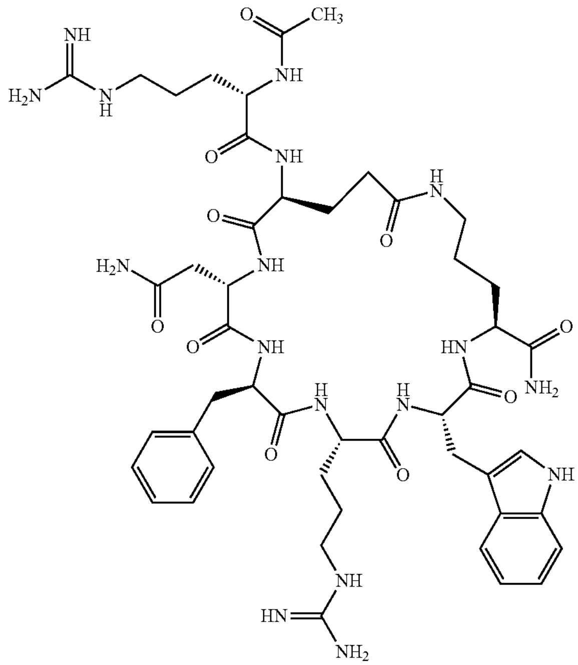 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O] | Ac-Arg-cyclo(Glu-Asn-D-Phe-Arg-Trp-Orn)-NH$_2$ | 6 |
| 162 | 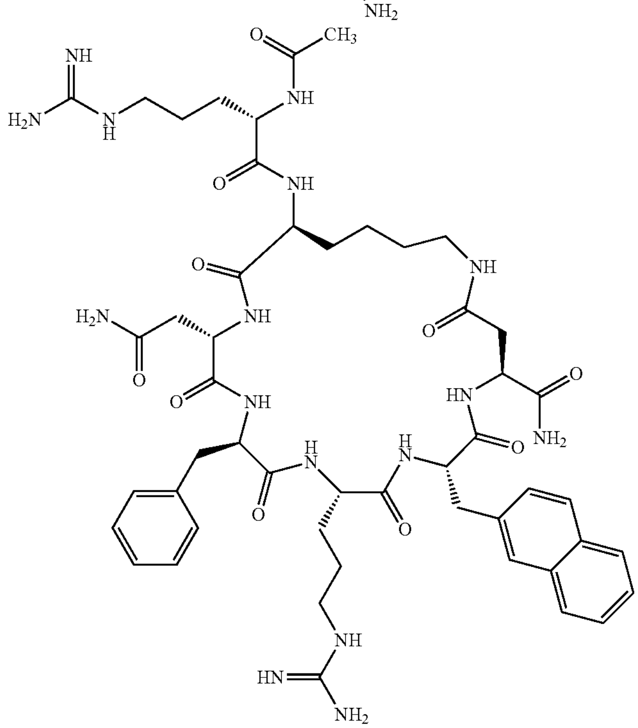 | Ac-Arg-cyclo(Lys-Asn-D-Phe-Arg-Nal 2-Asp)-NH$_2$ | 5 |

9.2 The peptides of Nos. 126 through 129 were tested in functional assays. The peptide No. 126 was determined to be an agonist at MC4-R, with intrinsic activity of 101% at MC4-R where NDP-α-MSH is 100%, and with an EC$_{50}$ of 0.047 nM (average of three studies). The peptide No. 127 was determined to be an agonist at MC4-R, with intrinsic activity of 98% at MC4-R where NDP-α-MSH is 100%, and with an EC$_{50}$ of 0.06 nM (average of two studies). The peptide No. 128 was determined to be an agonist at MC4-R, with intrinsic activity of 95% at MC4-R where NDP-α-MSH is 100%, and with an EC$_{50}$ of 0.073 nM (average of three studies). The peptide No. 129 was determined to be an agonist at MC4-R, with intrinsic activity of 96% at MC4-R where NDP-α-MSH is 100%, and with an EC$_{50}$ of 0.065 nM (average of two studies). Thus for the four peptides in the series, EC$_{50}$ values were on the order of one and one-half-fold to two-fold less that the Ki values.

9.3 Peptide No. 1 was evaluated for binding against MC1-R, MC3-R and MC4-R in competitive studies using Eu-labeled NDP-α-MSH, and was found to have a Ki value of 4 nM at MC4-R (average of six studies), a Ki value of 4 nM for MC1-R (average of four studies) and a Ki value of 103 nM for MC3-R (average of five studies). In competitive studies using [I$^{125}$]-NDP-α-MSH, peptide No. 1 was found to have a Ki value of 2 nM at MC4-R (one study), 25 nM at MC3-R (one study) and 3 nM at MC1-R (one study). In functional studies, Peptide No. 1 was determined to be an agonist, with intrinsic activity of 91% at MC4-R where NDP-α-MSH is 100%, and with an EC$_{50}$ of 1 nM (average of three studies).

In rat feeding studies, using bremelanotide (a non-specific MC4-R agonist of the formula Ac-Nle-cyclo(Asp-His-D-Phe-Arg-Trp-Lys)-OH)) as a positive control, peptide No. 1 was found to reduce food intake and decrease the rate of change in body weight. Using the methods as described above, groups of 8 rats each rats received 1 mg/kg bremelanotide, 0.3 mg/kg of peptide No. 1, 1 mg/kg of peptide No. 1 or vehicle control. For the 0-2, 0-4, and 0-20 hour periods, the decrease in food consumption in rats receiving either 0.3 or 1 mg/kg of peptide No. 1 was statistically significant compared to control. The 0-20 hour percent change in body weight was also statistically significant compared to control for the group receiving 1 mg/kg of peptide No. 1.

In rat penile erection studies, again using bremelanotide as a positive control, peptide No. 1 was found to result in a statistically significant increase, compared to vehicle, in observed spontaneous erections when administered IV at doses of 0.3 or 1 mg/kg.

9.4 Peptide No. 16 was evaluated for binding against MC1-R, MC3-R and MC4-R in competitive studies using Eu-labeled NDP-α-MSH, and was found to have a Ki value of 25 nM at MC4-R (average of two studies), a Ki value of 323 nM for MC1-R (one study) and a Ki value of 1055 nM for MC3-R (one study). In functional studies, Peptide No. 16 was determined to be a partial agonist, with intrinsic activity of 42% at MC4-R where NDP-α-MSH is 100%, and with an EC$_{50}$ of 40 nM (average of five studies).

In rat feeding studies, using bremelanotide as a positive control, peptide No. 16 was found to reduce food intake and decrease the rate of change in body weight. Using the methods as described above, groups of 8 rats each rats received 1 mg/kg bremelanotide, 0.3 mg/kg of peptide No. 16, 1 mg/kg of peptide No. 16 or vehicle control. For the 0-2, 0-4, and 0-20 hour periods, the decrease in food consumption in rats receiving 1 mg/kg of peptide No. 16 was statistically significant compared to control, and for the 0-2 and 0-4 hour periods, the decrease in food consumption in rats receiving 0.3 mg/kg of peptide No. 16 was statistically significant compared to control. The 0-20 hour percent change in body weight was also statistically significant compared to control for the group receiving 1 mg/kg of peptide No. 16.

9.5 Peptide No. 32 was evaluated for binding against MC1-R and MC4-R in competitive studies using Eu-labeled NDP-α-MSH, and was found to have a Ki value of 24 nM at MC4-R (average of six studies) and a Ki value of 673 nM for MC1-R (average of three studies). In competitive studies using [I$^{125}$]-NDP-α-MSH, peptide No. 32 was found to have a Ki value of 13 nM at MC4-R (two studies), 340 nM at MC3-R (one study) and 133 nM at MC1-R (two studies). In functional studies, Peptide No. 32 was determined to be an agonist, with intrinsic activity of 98% at MC4-R where NDP-α-MSH is 100%, and with an EC$_{50}$ of 17 nM (average of eight studies).

In rat penile erection studies, again using bremelanotide as a positive control, but with subcutaneous administration of peptide No. 32, peptide No. 32 was observed to result in an increase in observed spontaneous erections when administered at doses of 1, 3 or 10 mg/kg, but less than observed spontaneous erections observed with 1.0 mg/kg bremelanotide administered IV.

9.6 Certain peptides were tested for binding selectivity (Ki) to MC1-R and MC4-R, and also for functional selectivity (EC$_{50}$ and intrinsic activity, referred to as "E$_{max}$" below) to both MC1-R and MC4-R, with the results as shown below:

| Peptide No. | hMC4-R (Ki) (nM) | hMC1-R (Ki) (nM) | hMC4-R EC$_{50}$ (nM) | hMC4-R E$_{max}$ (%) | hMC1-R EC$_{50}$ (nM) | hMC1-R E$_{max}$ (%) |
|---|---|---|---|---|---|---|
| 71 | 45 | 3350 | 2 | 89 | 60 | 88 |
| 150 | 5 | 130 | 0.3 | 87 | 9 | 89 |
| 152 | 6 | 120 | 0.5 | 89 | 18 | 85 |
| 154 | 13 | 688 | 0.625 | 87 | 25 | 87 |
| 155 | 5 | 240 | 0.189 | 97 | 14 | 91 |
| 156 | 28 | 840 | 2 | 89 | 80 | 81 |
| 159 | 4 | 133 | 0.825 | 99 | 26 | 98 |
| 160 | 8 | 295 | 0.245 | 98 | 18 | 95 |
| 161 | 6 | 155 | 0.413 | 91 | 13 | 85 |
| 162 | 5 | 255 | 0.85 | 82 | 22 | 89 |

Thus while each of the foregoing peptides is an agonist at both MC1-R and MC4-R (defined as 70% or greater intrinsic activity), in all instances both binding selectivity and functional selectivity was at least twenty times more specific at MC4-R than at MC1-R.

Figure 2:
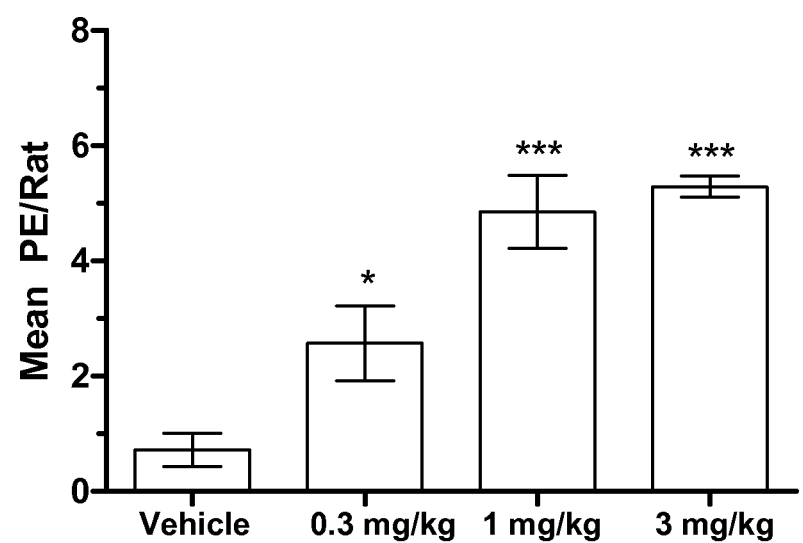
FIG. 2 is a bar graph of the mean number of penile erections per rat in a 60 minute observation period following administration of the indicated doses of peptide No. 155, with a vehicle control, where "*" indicates a p value of less than 0.05 and "***" indicates a p value of less than 0.01.

9.7 Peptide Nos. 154 and 155 were evaluated for the ability to induce penile erections in male Sprague-Dawley rats using the methodology generally described in Section 8.6. All injections were subcutaneous, with vehicle consisting of 3.2% mannitol/50 mM tris(hydroxymethyl)aminomethane buffer at pH 7.5 and active doses identical to buffer with the addition of the relevant concentration of peptide, with peptide No. 154 as the trifluoracetic acid salt and peptide No. 155 as the acetate salt. Each dose group contained six or seven animals, with video observation for sixty minutes following administration. Results for peptide No. 154 are shown in FIG. 1, and for peptide No. 155 in FIG. 2, with error bars representing the standard error of the mean. The results obtained demonstrate that peptide Nos. 154 and 155 robustly induce a penile erection in this animal model.

9.8 Peptide Nos. 154 and 155 were evaluated in pharmacokinetic studies, and in a rat model with subcutaneous injection of the formulation as in Section 9.7, each had a circulation half life of approximately 0.7 hours.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above are hereby incorporated by reference.

We claim:

1. A cyclic peptide having the structure of formula (III):

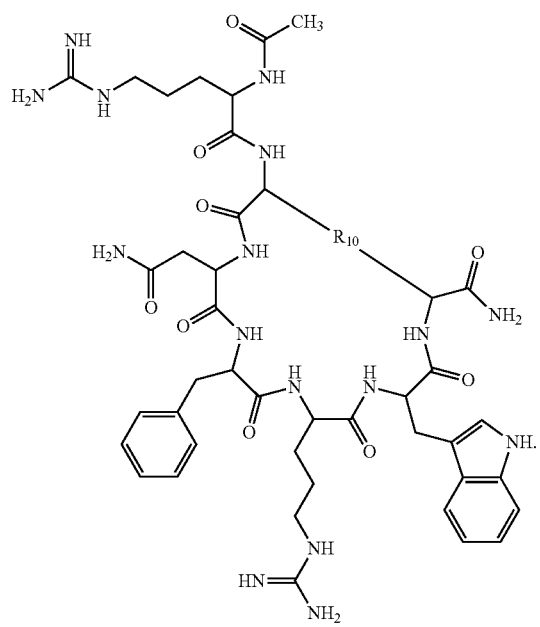

or a pharmaceutically acceptable salt thereof, wherein $R_{10}$ is $-(CH_2)_x-C(=O)-NH-(CH_2)_y-$, $-(CH_2)_x-NH-C(=O)-(CH_2)_y-$, $-(CH_2)_x-C(=O)-(CH_2)_z-C(=O)-(CH_2)_y-$, $-(CH_2)_x-C(=O)-NH-C(=O)-(CH_2)_y-$, or $-(CH_2)_x-NH-C(=O)-NH-(CH_2)_y-$:

x is 1 to 5;

y is 1 to 5; and z is in each instance independently 1 to 5.

2. The cyclic peptide of claim 1 wherein $R_{10}$ is $-(CH_2)_x-NH-C(=O)-(CH_2)_y-$ where x is 3 and y is 2.

3. The cyclic peptide of claim 1 which is a peptide of the structure:

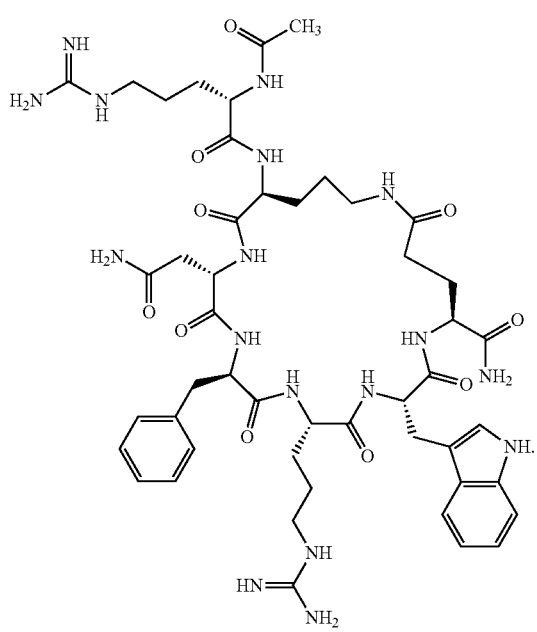 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O]

4. A pharmaceutical composition comprising a cyclic peptide of claim 1 and a pharmaceutically acceptable carrier.

5. A method for treatment of a melanocortin receptor-mediated disease, indication, condition or syndrome in a human or nonhuman mammal, comprising the step of administering the pharmaceutical composition of claim 4.

6. A method for treating a condition responsive to changes in melanocortin receptor function in a human or non-human mammal, comprising the step of administering the pharmaceutical composition of claim 4.

7. The cyclic peptide according to claim 3, which is an acetate salt.

8. The cyclic peptide according to claim 3, which is a trifluoroacetate salt.

9. A cyclic peptide which is
Ac-Arg-cyclo(Orn-Asn-D-Phe-Arg-Trp-Glu)-NH$_2$.

10. A pharmaceutical composition comprising the cyclic peptide according to claim 9 and a pharmaceutically acceptable carrier.

11. A method for treatment of a melanocortin receptor-mediated disease, indication, condition or syndrome in a human or non-human mammal, comprising the step of administering the pharmaceutical composition of claim 9.

12. A method for treating a condition responsive to changes in melanocortin receptor function in a human or non-human mammal, comprising the step of administering the pharmaceutical composition of claim 9.

* * * * *

UNITED STATES PATENT AND TRADEMARK OFFICE
CERTIFICATE OF CORRECTION

PATENT NO.       : 8,846,601 B2
APPLICATION NO.  : 13/311824
DATED            : September 30, 2014
INVENTOR(S)      : Yi-Qun Shi et al.

Page 1 of 1

It is certified that error appears in the above-identified patent and that said Letters Patent is hereby corrected as shown below:

In the Claims

Claim 5, Column 218, line 3, delete "nonhuman" and replace with --non-human--.
Claim 9, Column 218, line 15, delete "Ac-Arg-cyclo(Om-Asn-D-Phe-Arg-Trp-Glu)-$NH_2$." and replace with --Ac-Arg-cyclo(Orn-Asn-D-Phe-Arg-Trp-Glu)-$NH_2$.--.

Signed and Sealed this
Eighth Day of September, 2015

Michelle K. Lee
*Director of the United States Patent and Trademark Office*